United States Patent
Huitema et al.

(10) Patent No.: US 10,898,191 B2
(45) Date of Patent: Jan. 26, 2021

(54) FASTENER CARTRIDGE

(71) Applicant: Ethicon LLC, Guaynabo, PR (US)

(72) Inventors: Thomas W. Huitema, West Chester, OH (US); Douglas J. Siebenaler, Maineville, OH (US)

(73) Assignee: Ethicon LLC, Guaynabo, PR (US)

( * ) Notice: Subject to any disclaimer, the term of this patent is extended or adjusted under 35 U.S.C. 154(b) by 74 days.

(21) Appl. No.: 16/153,111

(22) Filed: Oct. 5, 2018

(65) Prior Publication Data

US 2019/0105042 A1    Apr. 11, 2019

Related U.S. Application Data

(63) Continuation of application No. 14/733,026, filed on Jun. 8, 2015, now Pat. No. 10,130,363, which is a
(Continued)

(51) Int. Cl.
*A61B 17/072* (2006.01)
*A61B 17/068* (2006.01)

(52) U.S. Cl.
CPC .... *A61B 17/07207* (2013.01); *A61B 17/0682* (2013.01); *A61B 2017/07214* (2013.01);
(Continued)

(58) Field of Classification Search
CPC ............ A61B 17/068; A61B 17/07214; A61B 17/00234; A61B 17/00491; A61B 17/064; A61B 90/92
(Continued)

(56) References Cited

U.S. PATENT DOCUMENTS 662,587 A    11/1900  Blake
951,393 A     3/1910  Hahn
(Continued)

FOREIGN PATENT DOCUMENTS

AU    2012200178 B2    7/2013
CN       2488482 Y     5/2002
(Continued)

OTHER PUBLICATIONS

Hoffman, "Hydrogels for Biomedical Applications," Advanced Drug Delivery Reviews, 54 (2002) pp. 3-12.
(Continued)

*Primary Examiner* — Nathaniel C Chukwurah

(57) ABSTRACT

A fastener cartridge comprising a cartridge body and unfired fasteners is disclosed. The cartridge body comprises fastener cavities and a deck comprising a variable height tissue compression surface. A longitudinal slot is defined through at least a portion of the variable height tissue compression surface. The fastener cavities comprise a first fastener cavity and a second fastener cavity. The first and second fastener cavities are defined in the variable height tissue compression surface on a first side of the longitudinal slot. The first fastener cavity is laterally offset from the second fastener cavity. The unfired fasteners comprise a first unfired fastener removable positioned in the first fastener cavity and a second unfired fastener removable positioned in the second fastener cavity. The first unfired fastener comprises a first height. The second unfired fastener comprises a second height that is different from the first height.

15 Claims, 20 Drawing Sheets

Related U.S. Application Data continuation of application No. 13/772,903, filed on Feb. 21, 2013, now Pat. No. 9,131,940, which is a continuation of application No. 12/893,461, filed on Sep. 29, 2010, now Pat. No. 8,733,613.

(52) U.S. Cl.
CPC ............... *A61B 2017/07271* (2013.01); *A61B 2017/07278* (2013.01)

(58) Field of Classification Search
USPC .......................................... 227/176.1–180.1
See application file for complete search history.

(56) References Cited

U.S. PATENT DOCUMENTS

| | | |
|---|---|---|
| 1,306,107 A | 6/1919 | Elliott |
| 2,132,295 A | 10/1938 | Hawkins |
| 2,161,632 A | 6/1939 | Nattenheimer |
| 2,211,117 A | 8/1940 | Hess |
| 2,526,902 A | 10/1950 | Rublee |
| 2,674,149 A | 4/1954 | Benson |
| 3,032,769 A | 5/1962 | Palmer |
| 3,079,606 A | 3/1963 | Bobrov et al. |
| 3,166,072 A | 1/1965 | Sullivan, Jr. |
| 3,357,296 A | 12/1967 | Lefever |
| 3,490,675 A | 1/1970 | Green et al. |
| 3,551,987 A | 1/1971 | Wilkinson |
| 3,744,495 A | 7/1973 | Johnson |
| 3,746,002 A | 7/1973 | Haller |
| 3,751,902 A | 8/1973 | Kingsbury et al. |
| 3,821,919 A | 7/1974 | Knohl |
| 3,841,474 A | 10/1974 | Maier |
| 3,885,491 A | 5/1975 | Curtis |
| 3,894,174 A | 7/1975 | Cartun |
| 3,981,051 A | 9/1976 | Brumlik |
| 4,060,089 A | 11/1977 | Noiles |
| 4,129,059 A | 12/1978 | Van Eck |
| 4,198,734 A | 4/1980 | Brumlik |
| 4,198,982 A | 4/1980 | Fortner et al. |
| 4,207,898 A | 6/1980 | Becht |
| 4,261,244 A | 4/1981 | Becht et al. |
| 4,275,813 A | 6/1981 | Noiles |
| 4,290,542 A | 9/1981 | Fedotov et al. |
| 4,305,539 A | 12/1981 | Korolkov et al. |
| 4,317,451 A | 3/1982 | Cerwin et al. |
| 4,321,002 A | 3/1982 | Froehlich |
| 4,340,331 A | 7/1982 | Savino |
| 4,379,457 A | 4/1983 | Gravener et al. |
| 4,382,326 A | 5/1983 | Rabuse |
| 4,397,311 A | 8/1983 | Kanshin et al. |
| 4,402,445 A | 9/1983 | Green |
| 4,409,057 A | 10/1983 | Molenda et al. |
| 4,428,376 A | 1/1984 | Mericle |
| 4,429,695 A | 2/1984 | Green |
| 4,434,796 A | 3/1984 | Karapetian et al. |
| 4,438,659 A | 3/1984 | Desplats |
| 4,467,805 A | 8/1984 | Fukuda |
| 4,485,816 A | 12/1984 | Krumme |
| 4,489,875 A | 12/1984 | Crawford et al. |
| 4,505,272 A | 3/1985 | Utyamyshev et al. |
| 4,505,273 A | 3/1985 | Braun et al. |
| 4,520,817 A | 6/1985 | Green |
| 4,526,174 A | 7/1985 | Froehlich |
| 4,548,202 A | 10/1985 | Duncan |
| 4,573,468 A | 3/1986 | Conta et al. |
| 4,573,469 A | 3/1986 | Golden et al. |
| 4,589,416 A | 5/1986 | Green |
| 4,604,786 A | 8/1986 | Howie, Jr. |
| 4,605,001 A | 8/1986 | Rothfuss et al. |
| 4,605,004 A | 8/1986 | Di Giovanni et al. |
| 4,607,638 A | 8/1986 | Crainich |
| 4,608,981 A | 9/1986 | Rothfuss et al. |
| 4,610,250 A | 9/1986 | Green |
| 4,610,383 A | 9/1986 | Rothfuss et al. |
| 4,612,933 A | 9/1986 | Brinkerhoff et al. |
| 4,619,262 A | 10/1986 | Taylor |
| 4,633,874 A | 1/1987 | Chow et al. |
| 4,634,419 A | 1/1987 | Kreizman et al. |
| 4,652,820 A | 3/1987 | Maresca |
| 4,655,222 A | 4/1987 | Florez et al. |
| 4,663,874 A | 5/1987 | Sano et al. |
| 4,667,674 A | 5/1987 | Korthoff et al. |
| 4,676,245 A | 6/1987 | Fukuda |
| 4,693,248 A | 9/1987 | Failla |
| 4,708,141 A | 11/1987 | Inoue et al. |
| 4,719,917 A | 1/1988 | Barrows et al. |
| 4,727,308 A | 2/1988 | Huljak et al. |
| 4,741,336 A | 5/1988 | Failla et al. |
| 4,747,820 A | 5/1988 | Hornlein et al. |
| 4,750,902 A | 6/1988 | Wuchinich et al. |
| 4,752,024 A | 6/1988 | Green et al. |
| 4,754,909 A | 7/1988 | Barker et al. |
| 4,767,044 A | 8/1988 | Green |
| 4,773,420 A | 9/1988 | Green |
| 4,777,780 A | 10/1988 | Holzwarth |
| 4,787,387 A | 11/1988 | Burbank, III et al. |
| 4,805,617 A | 2/1989 | Bedi et al. |
| 4,809,695 A | 3/1989 | Gwathmey et al. |
| 4,817,847 A | 4/1989 | Redtenbacher et al. |
| 4,827,911 A | 5/1989 | Broadwin et al. |
| 4,834,720 A | 5/1989 | Blinkhorn |
| 4,844,068 A | 7/1989 | Arata et al. |
| 4,865,030 A | 9/1989 | Polyak |
| 4,890,613 A | 1/1990 | Golden et al. |
| 4,893,622 A | 1/1990 | Green et al. |
| 4,896,678 A | 1/1990 | Ogawa |
| 4,903,697 A | 2/1990 | Resnick et al. |
| 4,930,674 A | 6/1990 | Barak |
| 4,931,047 A | 6/1990 | Broadwin et al. |
| 4,932,960 A | 6/1990 | Green et al. |
| 4,938,408 A | 7/1990 | Bedi et al. |
| 4,941,623 A | 7/1990 | Pruitt |
| 4,978,049 A | 12/1990 | Green |
| 4,978,333 A | 12/1990 | Broadwin et al. |
| 4,986,808 A | 1/1991 | Broadwin et al. |
| 5,002,553 A | 3/1991 | Shiber |
| 5,014,899 A | 5/1991 | Presty et al. |
| 5,015,227 A | 5/1991 | Broadwin et al. |
| 5,038,109 A | 8/1991 | Goble et al. |
| 5,040,715 A | 8/1991 | Green et al. |
| 5,074,454 A | 12/1991 | Peters |
| 5,088,997 A | 2/1992 | Delahuerga et al. |
| 5,104,397 A | 4/1992 | Vasconcelos et al. |
| 5,116,349 A | 5/1992 | Aranyi |
| 5,129,570 A | 7/1992 | Schulze et al. |
| 5,139,513 A | 8/1992 | Segato |
| 5,141,144 A | 8/1992 | Foslien et al. |
| 5,156,315 A | 10/1992 | Green et al. |
| 5,158,567 A | 10/1992 | Green |
| D330,699 S | 11/1992 | Gill |
| 5,163,598 A | 11/1992 | Peters et al. |
| 5,170,925 A | 12/1992 | Madden et al. |
| 5,171,253 A | 12/1992 | Klieman |
| 5,190,517 A | 3/1993 | Zieve et al. |
| 5,197,648 A | 3/1993 | Gingold |
| 5,205,459 A | 4/1993 | Brinkerhoff et al. |
| 5,221,281 A | 6/1993 | Klicek |
| 5,222,975 A | 6/1993 | Crainich |
| 5,222,976 A | 6/1993 | Yoon |
| 5,223,675 A | 6/1993 | Taft |
| 5,234,447 A | 8/1993 | Kaster et al. |
| 5,240,163 A | 8/1993 | Stein et al. |
| 5,242,457 A | 9/1993 | Akopov et al. |
| 5,246,443 A | 9/1993 | Mai |
| 5,258,009 A | 11/1993 | Conners |
| 5,258,012 A | 11/1993 | Luscombe et al. |
| 5,263,629 A | 11/1993 | Trumbull et al. |
| 5,263,973 A | 11/1993 | Cook |
| 5,275,608 A | 1/1994 | Forman et al. |
| 5,281,216 A | 1/1994 | Klicek |
| 5,282,829 A | 2/1994 | Hermes |
| 5,284,128 A | 2/1994 | Hart |
| 5,297,714 A | 3/1994 | Kramer |

(56) References Cited

U.S. PATENT DOCUMENTS

| | | |
|---|---|---|
| 5,304,204 A | 4/1994 | Bregen |
| 5,312,023 A | 5/1994 | Green et al. |
| 5,312,024 A | 5/1994 | Grant et al. |
| 5,312,329 A | 5/1994 | Beaty et al. |
| 5,333,772 A | 8/1994 | Rothfuss et al. |
| 5,336,229 A | 8/1994 | Noda |
| 5,336,232 A | 8/1994 | Green et al. |
| 5,342,395 A | 8/1994 | Jarrett et al. |
| 5,346,504 A | 9/1994 | Ortiz et al. |
| 5,350,388 A | 9/1994 | Epstein |
| 5,352,229 A | 10/1994 | Goble et al. |
| 5,352,238 A | 10/1994 | Green et al. |
| 5,358,506 A | 10/1994 | Green et al. |
| 5,358,510 A | 10/1994 | Luscombe et al. |
| 5,364,001 A | 11/1994 | Bryan |
| 5,364,003 A | 11/1994 | Williamson, IV |
| 5,366,134 A | 11/1994 | Green et al. |
| 5,370,645 A | 12/1994 | Klicek et al. |
| 5,372,596 A | 12/1994 | Klicek et al. |
| 5,374,277 A | 12/1994 | Hassler |
| 5,381,943 A | 1/1995 | Allen et al. |
| 5,382,247 A | 1/1995 | Cimino et al. |
| 5,383,882 A | 1/1995 | Buess et al. |
| 5,389,098 A | 2/1995 | Tsuruta et al. |
| 5,389,102 A | 2/1995 | Green et al. |
| 5,389,104 A | 2/1995 | Hahnen et al. |
| 5,392,979 A | 2/1995 | Green et al. |
| 5,395,030 A | 3/1995 | Kuramoto et al. |
| 5,395,033 A | 3/1995 | Byrne et al. |
| 5,395,384 A | 3/1995 | Duthoit et al. |
| 5,397,324 A | 3/1995 | Carroll et al. |
| 5,403,312 A | 4/1995 | Yates et al. |
| 5,405,072 A | 4/1995 | Zlock et al. |
| 5,405,344 A | 4/1995 | Williamson et al. |
| 5,413,272 A | 5/1995 | Green et al. |
| 5,413,573 A | 5/1995 | Koivukangas |
| 5,415,334 A | 5/1995 | Williamson et al. |
| 5,417,361 A | 5/1995 | Williamson, IV |
| 5,421,829 A | 6/1995 | Olichney et al. |
| 5,422,567 A | 6/1995 | Matsunaga |
| 5,423,471 A | 6/1995 | Mastri et al. |
| 5,423,809 A | 6/1995 | Klicek |
| 5,431,668 A | 7/1995 | Burbank, III et al. |
| 5,433,721 A | 7/1995 | Hooven et al. |
| 5,438,302 A | 8/1995 | Goble |
| 5,439,156 A | 8/1995 | Grant et al. |
| 5,441,191 A | 8/1995 | Linden |
| 5,441,193 A | 8/1995 | Gravener |
| 5,441,483 A | 8/1995 | Avitall |
| 5,445,644 A | 8/1995 | Pietrafitta et al. |
| 5,447,265 A | 9/1995 | Vidal et al. |
| 5,447,417 A | 9/1995 | Kuhl et al. |
| 5,449,355 A | 9/1995 | Rhum et al. |
| 5,452,836 A | 9/1995 | Huitema et al. |
| 5,452,837 A * | 9/1995 | Williamson, IV ............ A61B 17/07207 227/176.1 |
| 5,456,401 A | 10/1995 | Green et al. |
| 5,462,215 A | 10/1995 | Viola et al. |
| 5,465,819 A | 11/1995 | Weilant et al. |
| 5,465,895 A | 11/1995 | Knodel et al. |
| 5,465,896 A | 11/1995 | Allen et al. |
| 5,466,020 A | 11/1995 | Page et al. |
| 5,468,253 A | 11/1995 | Bezwada et al. |
| 5,470,009 A | 11/1995 | Rodak |
| 5,472,442 A | 12/1995 | Klicek |
| 5,474,057 A | 12/1995 | Makower et al. |
| 5,474,566 A | 12/1995 | Alesi et al. |
| 5,478,003 A | 12/1995 | Green et al. |
| 5,478,354 A | 12/1995 | Tovey et al. |
| 5,480,089 A | 1/1996 | Blewett |
| 5,482,197 A | 1/1996 | Green et al. |
| 5,484,398 A | 1/1996 | Stoddard |
| 5,485,947 A | 1/1996 | Olson et al. |
| 5,485,952 A | 1/1996 | Fontayne |
| 5,487,499 A | 1/1996 | Sorrentino et al. |
| 5,489,058 A | 2/1996 | Plyley et al. |
| 5,496,312 A | 3/1996 | Klicek |
| 5,496,317 A | 3/1996 | Goble et al. |
| 5,497,933 A | 3/1996 | DeFonzo et al. |
| 5,503,320 A | 4/1996 | Webster et al. |
| 5,503,638 A | 4/1996 | Cooper et al. |
| 5,505,363 A | 4/1996 | Green et al. |
| 5,507,426 A | 4/1996 | Young et al. |
| 5,509,596 A | 4/1996 | Green et al. |
| 5,509,916 A | 4/1996 | Taylor |
| 5,520,678 A | 5/1996 | Heckele et al. |
| 5,522,817 A | 6/1996 | Sander et al. |
| 5,529,235 A | 6/1996 | Boiarski et al. |
| 5,533,661 A | 7/1996 | Main et al. |
| 5,535,934 A | 7/1996 | Boiarski et al. |
| 5,540,375 A | 7/1996 | Bolanos et al. |
| 5,541,376 A | 7/1996 | Ladtkow et al. |
| 5,542,594 A | 8/1996 | McKean et al. |
| 5,549,621 A | 8/1996 | Bessler et al. |
| 5,551,622 A | 9/1996 | Yoon |
| 5,553,765 A | 9/1996 | Knodel et al. |
| 5,554,148 A | 9/1996 | Aebischer et al. |
| 5,560,530 A | 10/1996 | Bolanos et al. |
| 5,560,532 A | 10/1996 | DeFonzo et al. |
| 5,562,241 A | 10/1996 | Knodel et al. |
| 5,564,615 A | 10/1996 | Bishop et al. |
| 5,571,285 A | 11/1996 | Chow et al. |
| 5,573,543 A | 11/1996 | Akopov et al. |
| 5,575,803 A | 11/1996 | Cooper et al. |
| 5,577,654 A | 11/1996 | Bishop |
| 5,580,067 A | 12/1996 | Hamblin et al. |
| 5,582,611 A | 12/1996 | Tsuruta et al. |
| 5,586,711 A | 12/1996 | Plyley et al. |
| 5,588,579 A | 12/1996 | Schnut et al. |
| 5,588,580 A | 12/1996 | Paul et al. |
| 5,588,581 A | 12/1996 | Conlon et al. |
| 5,597,107 A | 1/1997 | Knodel et al. |
| 5,599,344 A | 2/1997 | Paterson |
| 5,601,224 A | 2/1997 | Bishop et al. |
| 5,603,443 A | 2/1997 | Clark et al. |
| 5,605,273 A | 2/1997 | Hamblin et al. |
| 5,607,094 A | 3/1997 | Clark et al. |
| 5,609,285 A | 3/1997 | Grant et al. |
| 5,609,601 A | 3/1997 | Kolesa et al. |
| 5,611,709 A | 3/1997 | McAnulty |
| 5,613,966 A | 3/1997 | Makower et al. |
| 5,615,820 A | 4/1997 | Viola |
| 5,618,303 A | 4/1997 | Marlow et al. |
| 5,619,992 A | 4/1997 | Guthrie et al. |
| 5,620,289 A | 4/1997 | Curry |
| 5,620,452 A | 4/1997 | Yoon |
| 5,628,446 A | 5/1997 | Geiste et al. |
| 5,628,743 A | 5/1997 | Cimino |
| 5,628,745 A | 5/1997 | Bek |
| 5,630,539 A | 5/1997 | Plyley et al. |
| 5,630,540 A | 5/1997 | Blewett |
| 5,632,432 A | 5/1997 | Schulze et al. |
| 5,632,433 A | 5/1997 | Grant et al. |
| 5,634,584 A | 6/1997 | Okorocha et al. |
| 5,636,780 A | 6/1997 | Green et al. |
| 5,639,008 A | 6/1997 | Gallagher et al. |
| 5,647,869 A | 7/1997 | Goble et al. |
| 5,649,937 A | 7/1997 | Bito et al. |
| 5,651,491 A | 7/1997 | Heaton et al. |
| 5,653,373 A | 8/1997 | Green et al. |
| 5,653,374 A | 8/1997 | Young et al. |
| 5,653,721 A | 8/1997 | Knodel et al. |
| 5,655,698 A | 8/1997 | Yoon |
| 5,657,921 A | 8/1997 | Young et al. |
| 5,658,300 A | 8/1997 | Bito et al. |
| 5,662,258 A | 9/1997 | Knodel et al. |
| 5,662,260 A | 9/1997 | Yoon |
| 5,662,662 A | 9/1997 | Bishop et al. |
| 5,667,517 A | 9/1997 | Hooven |
| 5,667,526 A | 9/1997 | Levin |
| 5,669,544 A | 9/1997 | Schulze et al. |
| 5,669,904 A | 9/1997 | Platt, Jr. et al. |
| 5,669,907 A | 9/1997 | Platt, Jr. et al. |

(56) References Cited

U.S. PATENT DOCUMENTS

| | | |
|---|---|---|
| 5,673,840 A | 10/1997 | Schulze et al. |
| 5,673,841 A | 10/1997 | Schulze et al. |
| 5,680,981 A | 10/1997 | Mililli et al. |
| 5,680,982 A | 10/1997 | Schulze et al. |
| 5,685,474 A | 11/1997 | Seeber |
| 5,690,269 A | 11/1997 | Bolanos et al. |
| 5,692,668 A | 12/1997 | Schulze et al. |
| 5,693,020 A | 12/1997 | Rauh |
| 5,693,051 A | 12/1997 | Schulze et al. |
| 5,695,494 A | 12/1997 | Becker |
| 5,695,524 A | 12/1997 | Kelley et al. |
| 5,697,543 A | 12/1997 | Burdorff |
| 5,702,387 A | 12/1997 | Arts et al. |
| 5,702,409 A | 12/1997 | Rayburn et al. |
| 5,704,534 A | 1/1998 | Huitema et al. |
| 5,709,680 A | 1/1998 | Yates et al. |
| 5,711,472 A | 1/1998 | Bryan |
| 5,713,505 A | 2/1998 | Huitema |
| 5,713,895 A | 2/1998 | Lontine et al. |
| 5,715,604 A | 2/1998 | Lanzoni |
| 5,715,987 A | 2/1998 | Kelley et al. |
| 5,718,360 A | 2/1998 | Green et al. |
| 5,720,744 A | 2/1998 | Eggleston et al. |
| 5,725,536 A | 3/1998 | Oberlin et al. |
| 5,725,554 A | 3/1998 | Simon et al. |
| 5,730,758 A | 3/1998 | Allgeyer |
| 5,732,871 A | 3/1998 | Clark et al. |
| 5,732,872 A | 3/1998 | Bolduc et al. |
| 5,735,874 A | 4/1998 | Measamer et al. |
| 5,743,456 A | 4/1998 | Jones et al. |
| 5,749,893 A | 5/1998 | Vidal et al. |
| 5,752,644 A | 5/1998 | Bolanos et al. |
| 5,752,965 A | 5/1998 | Francis et al. |
| 5,758,814 A | 6/1998 | Gallagher et al. |
| 5,762,256 A | 6/1998 | Mastri et al. |
| 5,766,188 A | 6/1998 | Igaki |
| 5,772,379 A | 6/1998 | Evensen |
| 5,772,659 A | 6/1998 | Becker et al. |
| 5,776,130 A | 7/1998 | Buysse et al. |
| 5,779,130 A | 7/1998 | Alesi et al. |
| 5,779,131 A | 7/1998 | Knodel et al. |
| 5,779,132 A | 7/1998 | Knodel et al. |
| 5,782,397 A | 7/1998 | Koukline |
| 5,782,748 A | 7/1998 | Palmer et al. |
| 5,785,232 A | 7/1998 | Vidal et al. |
| 5,797,536 A | 8/1998 | Smith et al. |
| 5,797,537 A | 8/1998 | Oberlin et al. |
| 5,797,538 A | 8/1998 | Heaton et al. |
| 5,799,857 A | 9/1998 | Robertson et al. |
| 5,800,379 A | 9/1998 | Edwards |
| 5,806,676 A | 9/1998 | Wasgien |
| 5,807,393 A | 9/1998 | Williamson, IV et al. |
| 5,810,855 A | 9/1998 | Rayburn et al. |
| 5,814,055 A | 9/1998 | Knodel et al. |
| 5,814,057 A | 9/1998 | Oi et al. |
| 5,820,009 A | 10/1998 | Melling et al. |
| 5,826,776 A | 10/1998 | Schulze et al. |
| 5,827,271 A | 10/1998 | Buysse et al. |
| 5,830,598 A | 11/1998 | Patterson |
| 5,833,695 A | 11/1998 | Yoon |
| 5,836,503 A | 11/1998 | Ehrenfels et al. |
| 5,839,639 A | 11/1998 | Sauer et al. |
| 5,843,021 A | 12/1998 | Edwards et al. |
| 5,843,096 A | 12/1998 | Igaki et al. |
| 5,855,311 A | 1/1999 | Hamblin et al. |
| 5,860,581 A | 1/1999 | Robertson et al. |
| 5,860,975 A | 1/1999 | Goble et al. |
| 5,865,361 A | 2/1999 | Milliman et al. |
| 5,871,135 A | 2/1999 | Williamson, IV et al. |
| 5,891,558 A | 4/1999 | Bell et al. |
| 5,893,506 A | 4/1999 | Powell |
| 5,897,552 A | 4/1999 | Edwards et al. |
| 5,901,895 A | 5/1999 | Heaton et al. |
| 5,902,312 A | 5/1999 | Frater et al. |
| 5,908,402 A | 6/1999 | Blythe |
| 5,911,353 A | 6/1999 | Bolanos et al. |
| 5,915,616 A | 6/1999 | Viola et al. |
| 5,937,951 A | 8/1999 | Izuchukwu et al. |
| 5,941,442 A | 8/1999 | Geiste et al. |
| 5,944,715 A | 8/1999 | Goble et al. |
| 5,947,984 A | 9/1999 | Whipple |
| 5,947,996 A | 9/1999 | Logeman |
| 5,951,552 A | 9/1999 | Long et al. |
| 5,954,259 A | 9/1999 | Viola et al. |
| 5,964,774 A | 10/1999 | McKean et al. |
| 5,984,949 A | 11/1999 | Levin |
| 6,004,319 A | 12/1999 | Goble et al. |
| 6,010,054 A | 1/2000 | Johnson et al. |
| 6,012,494 A | 1/2000 | Balazs |
| 6,013,076 A | 1/2000 | Goble et al. |
| 6,015,406 A | 1/2000 | Goble et al. |
| 6,027,501 A | 2/2000 | Goble et al. |
| 6,032,849 A | 3/2000 | Mastri et al. |
| 6,033,399 A | 3/2000 | Gines |
| 6,039,734 A | 3/2000 | Goble |
| 6,045,560 A | 4/2000 | McKean et al. |
| 6,050,172 A | 4/2000 | Corves et al. |
| 6,050,472 A | 4/2000 | Shibata |
| 6,050,996 A | 4/2000 | Schmaltz et al. |
| 6,053,390 A | 4/2000 | Green et al. |
| 6,053,922 A | 4/2000 | Krause et al. |
| RE36,720 E | 5/2000 | Green et al. |
| 6,063,097 A | 5/2000 | Oi et al. |
| 6,068,627 A | 5/2000 | Orszulak et al. |
| 6,074,401 A | 6/2000 | Gardiner et al. |
| 6,083,191 A | 7/2000 | Rose |
| 6,083,242 A | 7/2000 | Cook |
| 6,093,186 A | 7/2000 | Goble |
| 6,099,551 A | 8/2000 | Gabbay |
| 6,102,271 A | 8/2000 | Longo et al. |
| 6,117,158 A | 9/2000 | Measamer et al. |
| 6,119,913 A | 9/2000 | Adams et al. |
| 6,126,058 A | 10/2000 | Adams et al. |
| 6,149,660 A | 11/2000 | Laufer et al. |
| 6,156,056 A | 12/2000 | Kearns et al. |
| 6,162,208 A | 12/2000 | Hipps |
| 6,179,195 B1 | 1/2001 | Adams et al. |
| 6,187,003 B1 | 2/2001 | Buysse et al. |
| 6,193,129 B1 | 2/2001 | Bittner et al. |
| 6,197,042 B1 | 3/2001 | Ginn et al. |
| 6,200,330 B1 | 3/2001 | Benderev et al. |
| 6,202,914 B1 | 3/2001 | Geiste et al. |
| 6,210,403 B1 | 4/2001 | Klicek |
| 6,213,999 B1 | 4/2001 | Platt, Jr. et al. |
| 6,228,081 B1 | 5/2001 | Goble |
| 6,228,083 B1 | 5/2001 | Lands et al. |
| 6,241,139 B1 | 6/2001 | Milliman et al. |
| 6,241,140 B1 | 6/2001 | Adams et al. |
| 6,250,532 B1 | 6/2001 | Green et al. |
| 6,258,107 B1 | 7/2001 | Balazs et al. |
| 6,261,286 B1 | 7/2001 | Goble et al. |
| 6,264,086 B1 | 7/2001 | McGuckin, Jr. |
| 6,264,087 B1 | 7/2001 | Whitman |
| 6,273,897 B1 | 8/2001 | Dalessandro et al. |
| 6,277,114 B1 | 8/2001 | Bullivant et al. |
| 6,302,311 B1 | 10/2001 | Adams et al. |
| 6,315,184 B1 | 11/2001 | Whitman |
| 6,322,494 B1 | 11/2001 | Bullivant et al. |
| 6,325,799 B1 | 12/2001 | Goble |
| 6,325,805 B1 | 12/2001 | Ogilvie et al. |
| 6,325,810 B1 | 12/2001 | Hamilton et al. |
| 6,330,965 B1 | 12/2001 | Milliman et al. |
| 6,334,860 B1 | 1/2002 | Dorn |
| 6,334,861 B1 | 1/2002 | Chandler et al. |
| 6,336,926 B1 | 1/2002 | Goble |
| 6,343,731 B1 | 2/2002 | Adams et al. |
| 6,358,224 B1 | 3/2002 | Tims et al. |
| 6,383,201 B1 | 5/2002 | Dong |
| 6,387,113 B1 | 5/2002 | Hawkins et al. |
| 6,391,038 B2 | 5/2002 | Vargas et al. |
| 6,402,766 B2 | 6/2002 | Bowman et al. |
| H2037 H | 7/2002 | Yates et al. |
| 6,413,274 B1 | 7/2002 | Pedros |
| RE37,814 E | 8/2002 | Allgeyer |

(56) References Cited

U.S. PATENT DOCUMENTS

| | | |
|---|---|---|
| 6,436,110 B2 | 8/2002 | Bowman et al. |
| 6,443,973 B1 | 9/2002 | Whitman |
| 6,450,391 B1 | 9/2002 | Kayan et al. |
| 6,478,210 B2 | 11/2002 | Adams et al. |
| 6,485,503 B2 | 11/2002 | Jacobs et al. |
| 6,488,196 B1 | 12/2002 | Fenton, Jr. |
| 6,488,197 B1 | 12/2002 | Whitman |
| 6,488,659 B1 | 12/2002 | Rosenman |
| 6,491,201 B1 | 12/2002 | Whitman |
| 6,491,690 B1 | 12/2002 | Goble et al. |
| 6,503,257 B2 | 1/2003 | Grant et al. |
| 6,503,259 B2 | 1/2003 | Huxel et al. |
| 6,505,768 B2 | 1/2003 | Whitman |
| 6,517,528 B1 | 2/2003 | Pantages et al. |
| 6,517,565 B1 | 2/2003 | Whitman et al. |
| 6,517,566 B1 | 2/2003 | Hovland et al. |
| 6,533,157 B1 | 3/2003 | Whitman |
| 6,543,456 B1 | 4/2003 | Freeman |
| 6,551,333 B2 | 4/2003 | Kuhns et al. |
| 6,558,379 B1 | 5/2003 | Batchelor et al. |
| 6,569,085 B2 | 5/2003 | Kortenbach et al. |
| 6,578,751 B2 | 6/2003 | Hartwick |
| 6,585,144 B2 | 7/2003 | Adams et al. |
| 6,588,643 B2 | 7/2003 | Bolduc et al. |
| 6,589,118 B1 | 7/2003 | Soma et al. |
| 6,592,597 B2 | 7/2003 | Grant et al. |
| 6,601,749 B2 | 8/2003 | Sullivan et al. |
| 6,607,475 B2 | 8/2003 | Doyle et al. |
| 6,616,686 B2 | 9/2003 | Coleman et al. |
| 6,619,529 B2 | 9/2003 | Green et al. |
| 6,629,630 B2 | 10/2003 | Adams |
| 6,629,988 B2 | 10/2003 | Weadock |
| 6,638,285 B2 | 10/2003 | Gabbay |
| 6,638,297 B1 | 10/2003 | Huitema |
| 6,644,532 B2 | 11/2003 | Green et al. |
| 6,652,595 B1 | 11/2003 | Nicolo |
| 6,656,193 B2 | 12/2003 | Grant et al. |
| 6,669,073 B2 | 12/2003 | Milliman et al. |
| 6,670,806 B2 | 12/2003 | Wendt et al. |
| 6,671,185 B2 | 12/2003 | Duval |
| 6,676,660 B2 | 1/2004 | Wampler et al. |
| 6,681,978 B2 | 1/2004 | Geiste et al. |
| 6,681,979 B2 | 1/2004 | Whitman |
| 6,682,527 B2 | 1/2004 | Strul |
| 6,685,727 B2 | 2/2004 | Fisher et al. |
| 6,692,507 B2 | 2/2004 | Pugsley et al. |
| 6,695,198 B2 | 2/2004 | Adams et al. |
| 6,695,199 B2 | 2/2004 | Whitman |
| 6,698,643 B2 | 3/2004 | Whitman |
| 6,704,210 B1 | 3/2004 | Myers |
| 6,716,232 B1 | 4/2004 | Vidal et al. |
| 6,722,552 B2 | 4/2004 | Fenton, Jr. |
| 6,723,109 B2 | 4/2004 | Solingen |
| 6,736,854 B2 | 5/2004 | Vadurro et al. |
| 6,747,121 B2 | 6/2004 | Gogolewski |
| 6,749,560 B1 | 6/2004 | Konstorum et al. |
| 6,755,338 B2 | 6/2004 | Hahnen et al. |
| 6,761,685 B2 | 7/2004 | Adams et al. |
| 6,767,356 B2 | 7/2004 | Kanner et al. |
| 6,769,594 B2 | 8/2004 | Orban, III |
| 6,786,382 B1 | 9/2004 | Hoffman |
| 6,793,652 B1 | 9/2004 | Whitman et al. |
| 6,793,661 B2 | 9/2004 | Hamilton et al. |
| 6,805,273 B2 | 10/2004 | Bilotti et al. |
| 6,817,508 B1 | 11/2004 | Racenet et al. |
| 6,817,509 B2 | 11/2004 | Geiste et al. |
| 6,817,974 B2 | 11/2004 | Cooper et al. |
| 6,820,791 B2 | 11/2004 | Adams |
| 6,821,284 B2 | 11/2004 | Sturtz et al. |
| 6,827,246 B2 | 12/2004 | Sullivan et al. |
| 6,830,174 B2 | 12/2004 | Hillstead et al. |
| 6,835,336 B2 | 12/2004 | Watt |
| 6,837,846 B2 | 1/2005 | Jaffe et al. |
| 6,840,423 B2 | 1/2005 | Adams et al. |
| 6,843,403 B2 | 1/2005 | Whitman |
| 6,858,005 B2 | 2/2005 | Ohline et al. |
| RE38,708 E | 3/2005 | Bolanos et al. |
| 6,863,694 B1 | 3/2005 | Boyce et al. |
| 6,866,178 B2 | 3/2005 | Adams et al. |
| 6,874,669 B2 | 4/2005 | Adams et al. |
| 6,877,647 B2 | 4/2005 | Green et al. |
| 6,878,106 B2 | 4/2005 | Herrmann |
| 6,905,057 B2 | 6/2005 | Swayze et al. |
| 6,908,472 B2 | 6/2005 | Wiener et al. |
| 6,913,608 B2 | 7/2005 | Liddicoat et al. |
| 6,921,412 B1 | 7/2005 | Black et al. |
| 6,931,830 B2 | 8/2005 | Liao |
| 6,932,810 B2 | 8/2005 | Ryan |
| 6,939,358 B2 | 9/2005 | Palacios et al. |
| 6,945,444 B2 | 9/2005 | Gresham et al. |
| 6,953,138 B1 | 10/2005 | Dworak et al. |
| 6,953,139 B2 | 10/2005 | Milliman et al. |
| 6,958,035 B2 | 10/2005 | Friedman et al. |
| 6,959,851 B2 | 11/2005 | Heinrich |
| 6,959,852 B2 | 11/2005 | Shelton, IV et al. |
| 6,964,363 B2 | 11/2005 | Wales et al. |
| 6,969,395 B2 | 11/2005 | Eskuri |
| 6,974,462 B2 | 12/2005 | Sater |
| 6,978,921 B2 | 12/2005 | Shelton, IV et al. |
| 6,978,922 B2 | 12/2005 | Bilotti et al. |
| 6,981,628 B2 | 1/2006 | Wales |
| 6,981,978 B2 | 1/2006 | Gannoe |
| 6,984,231 B2 | 1/2006 | Goble et al. |
| 6,986,451 B1 | 1/2006 | Mastri et al. |
| 6,988,649 B2 | 1/2006 | Shelton, IV et al. |
| 6,988,650 B2 | 1/2006 | Schwemberger et al. |
| 6,990,796 B2 | 1/2006 | Schnipke et al. |
| 6,995,729 B2 | 2/2006 | Govari et al. |
| 7,000,818 B2 | 2/2006 | Shelton, IV et al. |
| 7,000,819 B2 | 2/2006 | Swayze et al. |
| 7,001,408 B2 | 2/2006 | Knodel et al. |
| 7,008,435 B2 | 3/2006 | Cummins |
| 7,018,357 B2 | 3/2006 | Emmons |
| 7,032,798 B2 | 4/2006 | Whitman et al. |
| 7,032,799 B2 | 4/2006 | Viola et al. |
| 7,037,344 B2 | 5/2006 | Kagan et al. |
| 7,041,868 B2 | 5/2006 | Greene et al. |
| 7,044,352 B2 | 5/2006 | Shelton, IV et al. |
| 7,044,353 B2 | 5/2006 | Mastri et al. |
| 7,052,494 B2 | 5/2006 | Goble et al. |
| 7,055,731 B2 | 6/2006 | Shelton, IV et al. |
| 7,056,330 B2 | 6/2006 | Gayton |
| 7,059,508 B2 | 6/2006 | Shelton, IV et al. |
| 7,063,712 B2 | 6/2006 | Vargas et al. |
| 7,066,944 B2 | 6/2006 | Laufer et al. |
| 7,070,083 B2 | 7/2006 | Jankowski |
| 7,080,769 B2 | 7/2006 | Vresh et al. |
| 7,083,075 B2 | 8/2006 | Swayze et al. |
| 7,097,644 B2 | 8/2006 | Long |
| 7,097,650 B2 | 8/2006 | Weller et al. |
| 7,104,741 B2 | 9/2006 | Krohn |
| 7,108,709 B2 | 9/2006 | Cummins |
| 7,111,769 B2 | 9/2006 | Wales et al. |
| 7,112,214 B2 | 9/2006 | Peterson et al. |
| 7,114,642 B2 | 10/2006 | Whitman |
| 7,119,534 B2 | 10/2006 | Butzmann |
| 7,121,446 B2 | 10/2006 | Arad et al. |
| 7,128,253 B2 | 10/2006 | Mastri et al. |
| 7,128,254 B2 | 10/2006 | Shelton, IV et al. |
| 7,128,748 B2 | 10/2006 | Mooradian et al. |
| 7,133,601 B2 | 11/2006 | Phillips et al. |
| 7,134,587 B2 | 11/2006 | Schwemberger et al. |
| 7,137,981 B2 | 11/2006 | Long |
| 7,140,527 B2 | 11/2006 | Ehrenfels et al. |
| 7,140,528 B2 | 11/2006 | Shelton, IV |
| 7,143,923 B2 | 12/2006 | Shelton, IV et al. |
| 7,143,924 B2 | 12/2006 | Scirica et al. |
| 7,143,925 B2 | 12/2006 | Shelton, IV et al. |
| 7,143,926 B2 | 12/2006 | Shelton, IV et al. |
| 7,147,138 B2 | 12/2006 | Shelton, IV |
| 7,147,139 B2 | 12/2006 | Schwemberger et al. |
| 7,147,637 B2 | 12/2006 | Goble |
| 7,147,650 B2 | 12/2006 | Lee |
| 7,150,748 B2 | 12/2006 | Ebbutt et al. |

(56) References Cited

U.S. PATENT DOCUMENTS

| | | |
|---|---|---|
| 7,156,863 B2 | 1/2007 | Sonnenschein et al. |
| 7,159,750 B2 | 1/2007 | Racenet et al. |
| 7,168,604 B2 | 1/2007 | Milliman et al. |
| 7,172,104 B2 | 2/2007 | Scirica et al. |
| 7,182,239 B1 | 2/2007 | Myers |
| 7,188,758 B2 | 3/2007 | Viola et al. |
| 7,199,537 B2 | 4/2007 | Okamura et al. |
| 7,204,404 B2 | 4/2007 | Nguyen et al. |
| 7,204,835 B2 | 4/2007 | Latterell et al. |
| 7,207,471 B2 | 4/2007 | Heinrich et al. |
| 7,207,472 B2 | 4/2007 | Wukusick et al. |
| 7,207,556 B2 | 4/2007 | Saitoh et al. |
| 7,210,609 B2 | 5/2007 | Leiboff et al. |
| 7,211,081 B2 | 5/2007 | Goble |
| 7,213,736 B2 | 5/2007 | Wales et al. |
| 7,217,285 B2 | 5/2007 | Vargas et al. |
| 7,225,964 B2 | 6/2007 | Mastri et al. |
| 7,234,624 B2 | 6/2007 | Gresham et al. |
| 7,235,302 B2 | 6/2007 | Jing et al. |
| 7,237,708 B1 | 7/2007 | Guy et al. |
| 7,238,195 B2 | 7/2007 | Viola |
| 7,246,734 B2 | 7/2007 | Shelton, IV |
| 7,247,161 B2 | 7/2007 | Johnston et al. |
| 7,258,262 B2 | 8/2007 | Mastri et al. |
| 7,258,546 B2 | 8/2007 | Beier et al. |
| 7,267,679 B2 | 9/2007 | McGuckin, Jr. et al. |
| 7,278,562 B2 | 10/2007 | Mastri et al. |
| 7,278,563 B1 | 10/2007 | Green |
| 7,282,048 B2 | 10/2007 | Goble et al. |
| 7,296,722 B2 | 11/2007 | Ivanko |
| 7,296,724 B2 | 11/2007 | Green et al. |
| 7,300,450 B2 | 11/2007 | Vleugels et al. |
| 7,303,106 B2 | 12/2007 | Milliman et al. |
| 7,303,107 B2 | 12/2007 | Milliman et al. |
| 7,303,108 B2 | 12/2007 | Shelton, IV |
| 7,308,998 B2 | 12/2007 | Mastri et al. |
| 7,326,203 B2 | 2/2008 | Papineau et al. |
| 7,326,213 B2 | 2/2008 | Benderev et al. |
| 7,328,828 B2 | 2/2008 | Ortiz et al. |
| 7,328,829 B2 | 2/2008 | Arad et al. |
| 7,331,340 B2 | 2/2008 | Barney |
| 7,331,969 B1 | 2/2008 | Inganas et al. |
| 7,334,717 B2 | 2/2008 | Rethy et al. |
| 7,334,718 B2 | 2/2008 | McAlister et al. |
| 7,336,048 B2 | 2/2008 | Lohr |
| 7,341,591 B2 | 3/2008 | Grinberg |
| RE40,237 E | 4/2008 | Bilotti et al. |
| 7,351,258 B2 | 4/2008 | Ricotta et al. |
| 7,354,447 B2 | 4/2008 | Shelton, IV et al. |
| 7,357,287 B2 | 4/2008 | Shelton, IV et al. |
| 7,357,806 B2 | 4/2008 | Rivera et al. |
| 7,364,060 B2 | 4/2008 | Milliman |
| 7,364,061 B2 | 4/2008 | Swayze et al. |
| 7,377,928 B2 | 5/2008 | Zubik et al. |
| 7,380,695 B2 | 6/2008 | Doll et al. |
| 7,380,696 B2 | 6/2008 | Shelton, IV et al. |
| 7,396,356 B2 | 7/2008 | Mollenauer |
| 7,398,907 B2 | 7/2008 | Racenet et al. |
| 7,398,908 B2 | 7/2008 | Holsten et al. |
| 7,401,721 B2 | 7/2008 | Holsten et al. |
| 7,404,508 B2 | 7/2008 | Smith et al. |
| 7,404,509 B2 | 7/2008 | Ortiz et al. |
| 7,404,822 B2 | 7/2008 | Viart et al. |
| 7,407,075 B2 | 8/2008 | Holsten et al. |
| 7,407,076 B2 | 8/2008 | Racenet et al. |
| 7,407,078 B2 | 8/2008 | Shelton, IV et al. |
| 7,410,086 B2 | 8/2008 | Ortiz et al. |
| 7,416,101 B2 | 8/2008 | Shelton, IV et al. |
| RE40,514 E | 9/2008 | Mastri et al. |
| 7,419,080 B2 | 9/2008 | Smith et al. |
| 7,419,081 B2 | 9/2008 | Ehrenfels et al. |
| 7,419,321 B2 | 9/2008 | Tereschouk |
| 7,422,136 B1 | 9/2008 | Marczyk |
| 7,422,139 B2 | 9/2008 | Shelton, IV et al. |
| 7,424,965 B2 | 9/2008 | Racenet et al. |
| 7,427,607 B2 | 9/2008 | Suzuki |
| 7,431,188 B1 | 10/2008 | Marczyk |
| 7,431,189 B2 | 10/2008 | Shelton, IV et al. |
| 7,431,694 B2 | 10/2008 | Stefanchik et al. |
| 7,431,730 B2 | 10/2008 | Viola |
| 7,434,715 B2 | 10/2008 | Shelton, IV et al. |
| 7,434,717 B2 | 10/2008 | Shelton, IV et al. |
| 7,438,209 B1 | 10/2008 | Hess et al. |
| 7,438,718 B2 | 10/2008 | Milliman et al. |
| 7,441,684 B2 | 10/2008 | Shelton, IV et al. |
| 7,441,685 B1 | 10/2008 | Boudreaux |
| 7,442,201 B2 | 10/2008 | Pugsley et al. |
| 7,448,525 B2 | 11/2008 | Shelton, IV et al. |
| 7,451,904 B2 | 11/2008 | Shelton, IV |
| 7,455,208 B2 | 11/2008 | Wales et al. |
| 7,455,676 B2 | 11/2008 | Holsten et al. |
| 7,461,767 B2 | 12/2008 | Viola et al. |
| 7,464,846 B2 | 12/2008 | Shelton, IV et al. |
| 7,464,847 B2 | 12/2008 | Viola et al. |
| 7,464,849 B2 | 12/2008 | Shelton, IV et al. |
| 7,467,740 B2 | 12/2008 | Shelton, IV et al. |
| 7,472,815 B2 | 1/2009 | Shelton, IV et al. |
| 7,472,816 B2 | 1/2009 | Holsten et al. |
| 7,473,253 B2 | 1/2009 | Dycus et al. |
| 7,481,347 B2 | 1/2009 | Roy |
| 7,481,349 B2 | 1/2009 | Holsten et al. |
| 7,485,124 B2 | 2/2009 | Kuhns et al. |
| 7,485,133 B2 | 2/2009 | Cannon et al. |
| 7,485,142 B2 | 2/2009 | Milo |
| 7,490,749 B2 | 2/2009 | Schall et al. |
| 7,494,039 B2 | 2/2009 | Racenet et al. |
| 7,500,979 B2 | 3/2009 | Hueil et al. |
| 7,503,474 B2 | 3/2009 | Hillstead et al. |
| 7,506,790 B2 | 3/2009 | Shelton, IV |
| 7,506,791 B2 | 3/2009 | Omaits et al. |
| 7,510,107 B2 | 3/2009 | Timm et al. |
| 7,510,566 B2 | 3/2009 | Jacobs et al. |
| 7,517,356 B2 | 4/2009 | Heinrich |
| 7,546,939 B2 | 6/2009 | Adams et al. |
| 7,546,940 B2 | 6/2009 | Milliman et al. |
| 7,547,312 B2 | 6/2009 | Bauman et al. |
| 7,549,563 B2 | 6/2009 | Mather et al. |
| 7,549,564 B2 | 6/2009 | Boudreaux |
| 7,549,998 B2 | 6/2009 | Braun |
| 7,556,185 B2 | 7/2009 | Viola |
| 7,559,449 B2 | 7/2009 | Viola |
| 7,559,450 B2 | 7/2009 | Wales et al. |
| 7,559,452 B2 | 7/2009 | Wales et al. |
| 7,565,993 B2 | 7/2009 | Milliman et al. |
| 7,568,603 B2 | 8/2009 | Shelton, IV et al. |
| 7,568,604 B2 | 8/2009 | Ehrenfels et al. |
| 7,575,144 B2 | 8/2009 | Ortiz et al. |
| 7,588,174 B2 | 9/2009 | Holsten et al. |
| 7,588,175 B2 | 9/2009 | Timm et al. |
| 7,588,176 B2 | 9/2009 | Timm et al. |
| 7,588,177 B2 | 9/2009 | Racenet |
| 7,597,229 B2 | 10/2009 | Boudreaux et al. |
| 7,597,230 B2 | 10/2009 | Racenet et al. |
| 7,604,150 B2 | 10/2009 | Boudreaux |
| 7,604,151 B2 | 10/2009 | Hess et al. |
| 7,607,557 B2 | 10/2009 | Shelton, IV et al. |
| 7,611,038 B2 | 11/2009 | Racenet et al. |
| 7,615,067 B2 | 11/2009 | Lee et al. |
| 7,624,902 B2 | 12/2009 | Marczyk et al. |
| 7,624,903 B2 | 12/2009 | Green et al. |
| 7,625,370 B2 | 12/2009 | Hart et al. |
| 7,631,793 B2 | 12/2009 | Rethy et al. |
| 7,635,074 B2 | 12/2009 | Olson et al. |
| 7,637,409 B2 | 12/2009 | Marczyk |
| 7,638,958 B2 | 12/2009 | Philipp et al. |
| 7,641,091 B2 | 1/2010 | Olson et al. |
| 7,641,092 B2 | 1/2010 | Kruszynski et al. |
| 7,641,095 B2 | 1/2010 | Viola |
| 7,644,848 B2 | 1/2010 | Swayze et al. |
| 7,645,230 B2 | 1/2010 | Mikkaichi et al. |
| 7,651,017 B2 | 1/2010 | Ortiz et al. |
| 7,651,498 B2 | 1/2010 | Shifrin et al. |
| 7,654,431 B2 | 2/2010 | Hueil et al. |
| 7,658,311 B2 | 2/2010 | Boudreaux |

(56) References Cited

U.S. PATENT DOCUMENTS

| | | |
|---|---|---|
| 7,658,312 B2 | 2/2010 | Vidal et al. |
| 7,662,161 B2 | 2/2010 | Briganti et al. |
| 7,665,646 B2 | 2/2010 | Prommersberger |
| 7,665,647 B2 | 2/2010 | Shelton, IV et al. |
| 7,669,746 B2 | 3/2010 | Shelton, IV |
| 7,669,747 B2 | 3/2010 | Weisenburgh, II et al. |
| 7,670,334 B2 | 3/2010 | Hueil et al. |
| 7,673,780 B2 | 3/2010 | Shelton, IV et al. |
| 7,673,781 B2 | 3/2010 | Swayze et al. |
| 7,673,782 B2 | 3/2010 | Hess et al. |
| 7,673,783 B2 | 3/2010 | Morgan et al. |
| 7,686,201 B2 | 3/2010 | Csiky |
| 7,695,485 B2 | 4/2010 | Whitman et al. |
| 7,699,204 B2 | 4/2010 | Viola |
| 7,699,846 B2 | 4/2010 | Ryan |
| 7,699,856 B2 | 4/2010 | Van Wyk et al. |
| 7,699,859 B2 | 4/2010 | Bombard et al. |
| 7,708,180 B2 | 5/2010 | Murray et al. |
| 7,708,182 B2 | 5/2010 | Viola |
| 7,708,758 B2 | 5/2010 | Lee et al. |
| 7,717,312 B2 | 5/2010 | Beetel |
| 7,717,313 B2 | 5/2010 | Criscuolo et al. |
| 7,717,846 B2 | 5/2010 | Zirps et al. |
| 7,718,180 B2 | 5/2010 | Karp |
| 7,718,556 B2 | 5/2010 | Matsuda et al. |
| 7,721,930 B2 | 5/2010 | McKenna et al. |
| 7,721,931 B2 | 5/2010 | Shelton, IV et al. |
| 7,721,933 B2 | 5/2010 | Ehrenfels et al. |
| 7,721,934 B2 | 5/2010 | Shelton, IV et al. |
| 7,721,936 B2 | 5/2010 | Shalton, IV et al. |
| 7,722,527 B2 | 5/2010 | Bouchier et al. |
| 7,722,610 B2 | 5/2010 | Viola et al. |
| 7,726,537 B2 | 6/2010 | Olson et al. |
| 7,726,538 B2 | 6/2010 | Holsten et al. |
| 7,731,072 B2 | 6/2010 | Timm et al. |
| 7,735,703 B2 | 6/2010 | Morgan et al. |
| 7,738,971 B2 | 6/2010 | Swayze et al. |
| 7,740,159 B2 | 6/2010 | Shelton, IV et al. |
| 7,743,960 B2 | 6/2010 | Whitman et al. |
| 7,744,627 B2 | 6/2010 | Orban, III et al. |
| 7,748,587 B2 | 7/2010 | Haramiishi et al. |
| 7,751,870 B2 | 7/2010 | Whitman |
| 7,753,245 B2 | 7/2010 | Boudreaux et al. |
| 7,753,904 B2 | 7/2010 | Shelton, IV et al. |
| 7,766,209 B2 | 8/2010 | Baxter, III et al. |
| 7,766,210 B2 | 8/2010 | Shelton, IV et al. |
| 7,766,821 B2 | 8/2010 | Brunnen et al. |
| 7,770,773 B2 | 8/2010 | Whitman et al. |
| 7,770,774 B2 | 8/2010 | Mastri et al. |
| 7,770,775 B2 | 8/2010 | Shelton, IV et al. |
| 7,770,776 B2 | 8/2010 | Chen et al. |
| 7,776,060 B2 | 8/2010 | Mooradian et al. |
| 7,780,054 B2 | 8/2010 | Wales |
| 7,780,055 B2 | 8/2010 | Scirica et al. |
| 7,780,663 B2 | 8/2010 | Yates et al. |
| 7,780,685 B2 | 8/2010 | Hunt et al. |
| 7,784,662 B2 | 8/2010 | Wales et al. |
| 7,784,663 B2 | 8/2010 | Shelton, IV |
| 7,789,889 B2 | 9/2010 | Zubik et al. |
| 7,793,812 B2 | 9/2010 | Moore et al. |
| 7,794,475 B2 | 9/2010 | Hess et al. |
| 7,798,386 B2 | 9/2010 | Schall et al. |
| 7,799,039 B2 | 9/2010 | Shelton, IV et al. |
| 7,810,690 B2 | 10/2010 | Bilotti et al. |
| 7,810,691 B2 | 10/2010 | Boyden et al. |
| 7,810,692 B2 | 10/2010 | Hall et al. |
| 7,810,693 B2 | 10/2010 | Broehl et al. |
| 7,815,092 B2 | 10/2010 | Whitman et al. |
| 7,819,296 B2 | 10/2010 | Hueil et al. |
| 7,819,297 B2 | 10/2010 | Doll et al. |
| 7,819,298 B2 | 10/2010 | Hall et al. |
| 7,819,299 B2 | 10/2010 | Shelton, IV et al. |
| 7,823,592 B2 | 11/2010 | Bettuchi et al. |
| 7,823,760 B2 | 11/2010 | Zemlok et al. |
| 7,828,189 B2 | 11/2010 | Holsten et al. |
| 7,832,408 B2 | 11/2010 | Shelton, IV et al. |
| 7,832,611 B2 | 11/2010 | Boyden et al. |
| 7,832,612 B2 | 11/2010 | Baxter, III et al. |
| 7,837,079 B2 | 11/2010 | Holsten et al. |
| 7,837,080 B2 | 11/2010 | Schwemberger |
| 7,837,081 B2 | 11/2010 | Holsten et al. |
| 7,837,694 B2 | 11/2010 | Tethrake et al. |
| 7,842,028 B2 | 11/2010 | Lee |
| 7,845,533 B2 | 12/2010 | Marczyk et al. |
| 7,845,535 B2 | 12/2010 | Scircia |
| 7,845,536 B2 | 12/2010 | Viola et al. |
| 7,845,537 B2 | 12/2010 | Shelton, IV et al. |
| 7,854,736 B2 | 12/2010 | Ryan |
| 7,857,183 B2 | 12/2010 | Shelton, IV |
| 7,857,185 B2 | 12/2010 | Swayze et al. |
| 7,857,186 B2 | 12/2010 | Baxter, III et al. |
| 7,857,813 B2 | 12/2010 | Schmitz et al. |
| 7,861,906 B2 | 1/2011 | Doll et al. |
| 7,866,525 B2 | 1/2011 | Scirica |
| 7,866,527 B2 | 1/2011 | Hall et al. |
| 7,886,951 B2 | 2/2011 | Hessler |
| 7,891,531 B1 | 2/2011 | Ward |
| 7,891,532 B2 | 2/2011 | Mastri et al. |
| 7,892,245 B2 | 2/2011 | Liddicoat et al. |
| 7,893,586 B2 | 2/2011 | West et al. |
| 7,896,215 B2 | 3/2011 | Adams et al. |
| 7,896,877 B2 | 3/2011 | Hall et al. |
| 7,900,805 B2 | 3/2011 | Shelton, IV et al. |
| 7,905,380 B2 | 3/2011 | Shelton, IV et al. |
| 7,905,381 B2 | 3/2011 | Baxter, III et al. |
| 7,909,039 B2 | 3/2011 | Hur |
| 7,909,220 B2 | 3/2011 | Viola |
| 7,909,221 B2 | 3/2011 | Viola et al. |
| 7,913,891 B2 | 3/2011 | Doll et al. |
| 7,913,893 B2 | 3/2011 | Mastri et al. |
| 7,914,543 B2 | 3/2011 | Roth et al. |
| 7,918,376 B1 | 4/2011 | Knodel et al. |
| 7,918,377 B2 | 4/2011 | Measamer et al. |
| 7,918,845 B2 | 4/2011 | Saadat et al. |
| 7,922,061 B2 | 4/2011 | Shelton, IV et al. |
| 7,922,063 B2 | 4/2011 | Zemlok et al. |
| 7,922,743 B2 | 4/2011 | Heinrich et al. |
| 7,926,691 B2 | 4/2011 | Viola et al. |
| 7,931,660 B2 | 4/2011 | Aranyi et al. |
| 7,934,630 B2 | 5/2011 | Shelton, IV et al. |
| 7,934,631 B2 | 5/2011 | Balbierz et al. |
| 7,935,773 B2 | 5/2011 | Hadba et al. |
| 7,938,307 B2 | 5/2011 | Bettuchi |
| 7,942,890 B2 | 5/2011 | D'Agostino et al. |
| 7,950,560 B2 | 5/2011 | Zemlok et al. |
| 7,950,561 B2 | 5/2011 | Aranyi |
| 7,951,071 B2 | 5/2011 | Whitman et al. |
| 7,951,166 B2 | 5/2011 | Orban, III et al. |
| 7,954,682 B2 | 6/2011 | Giordano et al. |
| 7,954,684 B2 | 6/2011 | Boudreaux |
| 7,954,686 B2 | 6/2011 | Baxter, III et al. |
| 7,954,687 B2 | 6/2011 | Zemlok et al. |
| 7,959,050 B2 | 6/2011 | Smith et al. |
| 7,959,051 B2 | 6/2011 | Smith et al. |
| 7,963,432 B2 | 6/2011 | Knodel et al. |
| 7,963,433 B2 | 6/2011 | Whitman et al. |
| 7,966,799 B2 | 6/2011 | Morgan et al. |
| 7,967,180 B2 | 6/2011 | Scirica |
| 7,967,181 B2 | 6/2011 | Viola et al. |
| 7,967,839 B2 | 6/2011 | Flock et al. |
| 7,972,298 B2 | 7/2011 | Wallace et al. |
| 7,976,563 B2 | 7/2011 | Summerer |
| 7,980,443 B2 | 7/2011 | Scheib et al. |
| 7,988,026 B2 | 8/2011 | Knodel et al. |
| 7,988,027 B2 | 8/2011 | Olson et al. |
| 7,988,779 B2 | 8/2011 | Disalvo et al. |
| 7,992,757 B2 | 8/2011 | Wheeler et al. |
| 7,997,469 B2 | 8/2011 | Olson et al. |
| 8,002,795 B2 | 8/2011 | Beetel |
| 8,006,885 B2 | 8/2011 | Marczyk |
| 8,006,889 B2 | 8/2011 | Adams et al. |
| 8,007,513 B2 | 8/2011 | Nalagatla et al. |
| 8,011,550 B2 | 9/2011 | Aranyi et al. |
| 8,011,551 B2 | 9/2011 | Marczyk et al. |

(56) References Cited

U.S. PATENT DOCUMENTS

| | | |
|---|---|---|
| 8,011,553 B2 | 9/2011 | Mastri et al. |
| 8,011,555 B2 | 9/2011 | Tarinelli et al. |
| 8,016,176 B2 | 9/2011 | Kasvikis et al. |
| 8,016,177 B2 | 9/2011 | Bettuchi et al. |
| 8,016,178 B2 | 9/2011 | Olson et al. |
| 8,016,849 B2 | 9/2011 | Wenchell |
| 8,016,855 B2 | 9/2011 | Whitman et al. |
| 8,016,858 B2 | 9/2011 | Whitman |
| 8,020,742 B2 | 9/2011 | Marczyk |
| 8,020,743 B2 | 9/2011 | Shelton, IV |
| 8,025,199 B2 | 9/2011 | Whitman et al. |
| 8,028,883 B2 | 10/2011 | Stopek |
| 8,028,885 B2 | 10/2011 | Smith et al. |
| 8,033,438 B2 | 10/2011 | Scirica |
| 8,035,487 B2 | 10/2011 | Malackowski |
| 8,038,045 B2 | 10/2011 | Bettuchi et al. |
| 8,038,046 B2 | 10/2011 | Smith et al. |
| 8,047,236 B2 | 11/2011 | Perry |
| 8,056,787 B2 | 11/2011 | Boudreaux et al. |
| 8,056,788 B2 | 11/2011 | Mastri et al. |
| 8,062,330 B2 | 11/2011 | Prommersberger et al. |
| 8,066,167 B2 | 11/2011 | Measamer et al. |
| D650,074 S | 12/2011 | Hunt et al. |
| 8,083,119 B2 | 12/2011 | Prommersberger |
| 8,083,120 B2 | 12/2011 | Shelton, IV et al. |
| 8,091,756 B2 | 1/2012 | Viola |
| 8,092,932 B2 | 1/2012 | Phillips et al. |
| 8,097,017 B2 | 1/2012 | Viola |
| 8,100,310 B2 | 1/2012 | Zemlok |
| 8,105,350 B2 | 1/2012 | Lee et al. |
| 8,109,426 B2 | 2/2012 | Milliman et al. |
| 8,113,410 B2 | 2/2012 | Hall et al. |
| 8,114,100 B2 | 2/2012 | Smith et al. |
| 8,123,103 B2 | 2/2012 | Milliman |
| 8,123,767 B2 | 2/2012 | Bauman et al. |
| 8,128,645 B2 | 3/2012 | Sonnenschein et al. |
| 8,136,712 B2 | 3/2012 | Zingman |
| 8,140,417 B2 | 3/2012 | Shibata |
| 8,141,762 B2 | 3/2012 | Bedi et al. |
| 8,141,763 B2 | 3/2012 | Milliman |
| 8,152,041 B2 | 4/2012 | Kostrzewski |
| 8,152,756 B2 | 4/2012 | Webster et al. |
| 8,157,145 B2 | 4/2012 | Shelton, IV et al. |
| 8,157,148 B2 | 4/2012 | Scirica |
| 8,157,152 B2 | 4/2012 | Holsten et al. |
| 8,157,153 B2 | 4/2012 | Shelton, IV et al. |
| 8,161,977 B2 | 4/2012 | Shelton, IV et al. |
| 8,162,138 B2 | 4/2012 | Bettenhausen et al. |
| 8,162,197 B2 | 4/2012 | Mastri et al. |
| 8,162,933 B2 | 4/2012 | Francischelli et al. |
| 8,167,185 B2 | 5/2012 | Shelton, IV et al. |
| 8,167,895 B2 | 5/2012 | D'Agostino et al. |
| 8,172,120 B2 | 5/2012 | Boyden et al. |
| 8,172,122 B2 | 5/2012 | Kasvikis et al. |
| 8,172,124 B2 | 5/2012 | Shelton, IV et al. |
| 8,177,797 B2 | 5/2012 | Shimoji et al. |
| 8,186,555 B2 | 5/2012 | Shelton, IV et al. |
| 8,186,560 B2 | 5/2012 | Hess et al. |
| 8,191,752 B2 | 6/2012 | Scirica |
| 8,192,460 B2 | 6/2012 | Orban, III et al. |
| 8,196,795 B2 | 6/2012 | Moore et al. |
| 8,196,796 B2 | 6/2012 | Shelton, IV et al. |
| 8,201,721 B2 | 6/2012 | Zemlok et al. |
| 8,205,781 B2 | 6/2012 | Baxter, III et al. |
| 8,210,411 B2 | 7/2012 | Yates et al. |
| 8,210,414 B2 | 7/2012 | Bettuchi et al. |
| 8,210,415 B2 | 7/2012 | Ward |
| 8,211,125 B2 | 7/2012 | Spivey |
| 8,214,019 B2 | 7/2012 | Govari et al. |
| 8,215,531 B2 | 7/2012 | Shelton, IV et al. |
| 8,215,533 B2 | 7/2012 | Viola et al. |
| 8,220,688 B2 | 7/2012 | Laurent et al. |
| 8,220,690 B2 | 7/2012 | Hess et al. |
| 8,225,799 B2 | 7/2012 | Bettuchi |
| 8,231,040 B2 | 7/2012 | Zemlok et al. |
| 8,231,042 B2 | 7/2012 | Hessler et al. |
| 8,231,043 B2 | 7/2012 | Tarinelli et al. |
| 8,236,010 B2 | 8/2012 | Ortiz et al. |
| 8,241,308 B2 | 8/2012 | Kortenbach et al. |
| 8,241,322 B2 | 8/2012 | Whitman et al. |
| 8,245,899 B2 | 8/2012 | Swensgard et al. |
| 8,245,900 B2 | 8/2012 | Scirica |
| 8,245,901 B2 | 8/2012 | Stopek |
| 8,246,637 B2 | 8/2012 | Viola et al. |
| 8,256,654 B2 | 9/2012 | Bettuchi et al. |
| 8,256,655 B2 | 9/2012 | Sniffin et al. |
| 8,257,356 B2 | 9/2012 | Bleich et al. |
| 8,257,391 B2 | 9/2012 | Orban, III et al. |
| 8,267,300 B2 | 9/2012 | Boudreaux |
| 8,272,553 B2 | 9/2012 | Mastri et al. |
| 8,276,801 B2 | 10/2012 | Zemlok et al. |
| 8,276,802 B2 | 10/2012 | Kostrzewski |
| 8,281,973 B2 | 10/2012 | Wenchell et al. |
| 8,286,845 B2 | 10/2012 | Perry et al. |
| 8,292,150 B2 | 10/2012 | Bryant |
| 8,292,151 B2 | 10/2012 | Viola |
| 8,292,155 B2 | 10/2012 | Shelton, IV et al. |
| 8,292,157 B2 | 10/2012 | Smith et al. |
| 8,292,888 B2 | 10/2012 | Whitman |
| 8,308,040 B2 | 11/2012 | Huang et al. |
| 8,308,042 B2 | 11/2012 | Aranyi |
| 8,308,046 B2 | 11/2012 | Prommersberger |
| 8,313,496 B2 | 11/2012 | Sauer et al. |
| 8,313,509 B2 | 11/2012 | Kostrzewski |
| 8,317,070 B2 | 11/2012 | Hueil et al. |
| 8,317,074 B2 | 11/2012 | Ortiz et al. |
| 8,317,744 B2 | 11/2012 | Kirschenman |
| 8,322,455 B2 | 12/2012 | Shelton, IV et al. |
| 8,322,589 B2 | 12/2012 | Boudreaux |
| 8,328,062 B2 | 12/2012 | Viola |
| 8,328,063 B2 | 12/2012 | Milliman et al. |
| 8,328,064 B2 | 12/2012 | Racenet et al. |
| 8,333,313 B2 | 12/2012 | Boudreaux et al. |
| 8,333,764 B2 | 12/2012 | Francischelli et al. |
| 8,348,123 B2 | 1/2013 | Scirica et al. |
| 8,348,127 B2 | 1/2013 | Marczyk |
| 8,348,129 B2 | 1/2013 | Bedi et al. |
| 8,348,130 B2 | 1/2013 | Shah et al. |
| 8,348,131 B2 | 1/2013 | Omaits et al. |
| 8,353,437 B2 | 1/2013 | Boudreaux |
| 8,353,438 B2 | 1/2013 | Baxter, III et al. |
| 8,353,439 B2 | 1/2013 | Baxter, III et al. |
| 8,360,296 B2 | 1/2013 | Zingman |
| 8,360,297 B2 | 1/2013 | Shelton, IV et al. |
| 8,360,299 B2 | 1/2013 | Zemlok et al. |
| 8,365,973 B1 | 2/2013 | White et al. |
| 8,365,976 B2 | 2/2013 | Hess et al. |
| 8,366,787 B2 | 2/2013 | Brown et al. |
| 8,371,491 B2 | 2/2013 | Huitema et al. |
| 8,371,492 B2 | 2/2013 | Aranyi et al. |
| 8,371,493 B2 | 2/2013 | Aranyi et al. |
| 8,372,094 B2 | 2/2013 | Bettuchi et al. |
| 8,377,029 B2 | 2/2013 | Nagao et al. |
| 8,393,513 B2 | 3/2013 | Jankowski |
| 8,393,514 B2 | 3/2013 | Shelton, IV et al. |
| 8,397,971 B2 | 3/2013 | Yates et al. |
| 8,398,633 B2 | 3/2013 | Mueller |
| 8,403,198 B2 | 3/2013 | Sorrentino et al. |
| 8,403,945 B2 | 3/2013 | Whitfield et al. |
| 8,408,439 B2 | 4/2013 | Huang et al. |
| 8,408,442 B2 | 4/2013 | Racenet et al. |
| 8,413,870 B2 | 4/2013 | Pastorelli et al. |
| 8,413,871 B2 | 4/2013 | Racenet et al. |
| 8,413,872 B2 | 4/2013 | Patel |
| 8,414,577 B2 | 4/2013 | Boudreaux et al. |
| 8,424,739 B2 | 4/2013 | Racenet et al. |
| 8,424,740 B2 | 4/2013 | Shelton, IV et al. |
| 8,424,741 B2 | 4/2013 | McGuckin, Jr. et al. |
| 8,444,036 B2 | 5/2013 | Shelton, IV |
| 8,453,904 B2 | 6/2013 | Eskaros et al. |
| 8,453,907 B2 | 6/2013 | Laurent et al. |
| 8,453,908 B2 | 6/2013 | Bedi et al. |
| 8,453,912 B2 | 6/2013 | Mastri et al. |
| 8,453,914 B2 | 6/2013 | Laurent et al. |

(56) References Cited

U.S. PATENT DOCUMENTS

| | | |
|---|---|---|
| 8,459,520 B2 | 6/2013 | Giordano et al. |
| 8,459,525 B2 | 6/2013 | Yates et al. |
| 8,464,922 B2 | 6/2013 | Marczyk |
| 8,464,923 B2 | 6/2013 | Shelton, IV |
| 8,464,924 B2 | 6/2013 | Gresham et al. |
| 8,464,925 B2 | 6/2013 | Hull et al. |
| 8,469,973 B2 | 6/2013 | Meade et al. |
| 8,470,355 B2 | 6/2013 | Skalla et al. |
| 8,474,677 B2 | 7/2013 | Woodard, Jr. et al. |
| 8,475,454 B1 | 7/2013 | Alshemari |
| 8,479,969 B2 | 7/2013 | Shelton, IV |
| 8,480,703 B2 | 7/2013 | Nicholas et al. |
| 8,485,412 B2 | 7/2013 | Shelton, IV et al. |
| 8,485,413 B2 | 7/2013 | Scheib et al. |
| 8,490,853 B2 | 7/2013 | Criscuolo et al. |
| 8,496,156 B2 | 7/2013 | Sniffin et al. |
| 8,499,993 B2 | 8/2013 | Shelton, IV et al. |
| 8,500,762 B2 | 8/2013 | Sholev et al. |
| 8,506,555 B2 | 8/2013 | Ruiz Morales |
| 8,517,239 B2 | 8/2013 | Scheib et al. |
| 8,517,241 B2 | 8/2013 | Nicholas et al. |
| 8,517,243 B2 | 8/2013 | Giordano et al. |
| 8,517,244 B2 | 8/2013 | Shelton, IV et al. |
| 8,523,043 B2 | 9/2013 | Ullrich et al. |
| 8,529,600 B2 | 9/2013 | Woodard, Jr. et al. |
| 8,534,528 B2 | 9/2013 | Shelton, IV |
| 8,540,128 B2 | 9/2013 | Shelton, IV et al. |
| 8,540,129 B2 | 9/2013 | Baxter, III et al. |
| 8,540,130 B2 | 9/2013 | Moore et al. |
| 8,540,131 B2 | 9/2013 | Swayze |
| 8,540,133 B2 | 9/2013 | Bedi et al. |
| 8,550,984 B2 | 10/2013 | Takemoto |
| 8,556,151 B2 | 10/2013 | Viola |
| 8,561,870 B2 | 10/2013 | Baxter, III et al. |
| 8,567,656 B2 | 10/2013 | Shelton, IV et al. |
| 8,568,425 B2 | 10/2013 | Ross et al. |
| 8,573,459 B2 | 11/2013 | Smith et al. |
| 8,573,461 B2 | 11/2013 | Shelton, IV et al. |
| 8,573,465 B2 | 11/2013 | Shelton, IV |
| 8,579,937 B2 | 11/2013 | Gresham |
| 8,584,919 B2 | 11/2013 | Hueil et al. |
| 8,585,721 B2 | 11/2013 | Kirsch |
| 8,590,760 B2 | 11/2013 | Cummins et al. |
| 8,590,762 B2 | 11/2013 | Hess et al. |
| 8,590,764 B2 | 11/2013 | Hartwick et al. |
| 8,602,287 B2 | 12/2013 | Yates et al. |
| 8,602,288 B2 | 12/2013 | Shelton, IV et al. |
| 8,608,043 B2 | 12/2013 | Scirica |
| 8,608,044 B2 | 12/2013 | Hueil et al. |
| 8,608,045 B2 | 12/2013 | Smith et al. |
| 8,608,046 B2 | 12/2013 | Laurent et al. |
| 8,616,431 B2 | 12/2013 | Timm et al. |
| 8,622,274 B2 | 1/2014 | Yates et al. |
| 8,622,275 B2 | 1/2014 | Baxter, III et al. |
| 8,627,995 B2 | 1/2014 | Smith et al. |
| 8,631,987 B2 | 1/2014 | Shelton, IV et al. |
| 8,631,993 B2 | 1/2014 | Kostrzewski |
| 8,632,462 B2 | 1/2014 | Yoo et al. |
| 8,632,525 B2 | 1/2014 | Kerr et al. |
| 8,632,535 B2 | 1/2014 | Shelton, IV et al. |
| 8,632,563 B2 | 1/2014 | Nagase et al. |
| 8,636,187 B2 | 1/2014 | Hueil et al. |
| 8,636,191 B2 | 1/2014 | Meagher |
| 8,636,736 B2 | 1/2014 | Yates et al. |
| 8,646,674 B2 | 2/2014 | Schulte et al. |
| 8,652,120 B2 | 2/2014 | Giordano et al. |
| 8,657,174 B2 | 2/2014 | Yates et al. |
| 8,657,176 B2 | 2/2014 | Shelton, IV et al. |
| 8,657,178 B2 | 2/2014 | Hueil et al. |
| 8,668,130 B2 | 3/2014 | Hess et al. |
| 8,672,207 B2 | 3/2014 | Shelton, IV et al. |
| 8,672,208 B2 | 3/2014 | Hess et al. |
| 8,672,951 B2 | 3/2014 | Smith et al. |
| 8,678,263 B2 | 3/2014 | Viola |
| 8,679,154 B2 | 3/2014 | Smith et al. |
| 8,684,253 B2 | 4/2014 | Giordano et al. |
| 8,695,866 B2 | 4/2014 | Leimbach et al. |
| 8,701,958 B2 | 4/2014 | Shelton, IV et al. |
| 8,708,210 B2 | 4/2014 | Zemlok et al. |
| 8,708,213 B2 | 4/2014 | Shelton, IV et al. |
| 8,714,430 B2 | 5/2014 | Natarajan et al. |
| 8,720,766 B2 | 5/2014 | Hess et al. |
| 8,721,630 B2 | 5/2014 | Ortiz et al. |
| 8,727,197 B2 | 5/2014 | Hess et al. |
| 8,727,199 B2 | 5/2014 | Wenchell |
| 8,733,612 B2 | 5/2014 | Ma |
| 8,733,613 B2 | 5/2014 | Huitema et al. |
| 8,734,478 B2 | 5/2014 | Widenhouse et al. |
| 8,740,034 B2 | 6/2014 | Morgan et al. |
| 8,740,037 B2 | 6/2014 | Shelton, IV et al. |
| 8,740,038 B2 | 6/2014 | Shelton, IV et al. |
| 8,746,529 B2 | 6/2014 | Shelton, IV et al. |
| 8,746,530 B2 | 6/2014 | Giordano et al. |
| 8,746,535 B2 | 6/2014 | Shelton, IV et al. |
| 8,747,238 B2 | 6/2014 | Shelton, IV et al. |
| 8,752,699 B2 | 6/2014 | Morgan et al. |
| 8,752,747 B2 | 6/2014 | Shelton, IV et al. |
| 8,752,749 B2 | 6/2014 | Moore et al. |
| 8,757,465 B2 | 6/2014 | Woodard, Jr. et al. |
| 8,758,391 B2 | 6/2014 | Swayze et al. |
| 8,763,875 B2 | 7/2014 | Morgan et al. |
| 8,763,877 B2 | 7/2014 | Schall et al. |
| 8,763,879 B2 | 7/2014 | Shelton, IV et al. |
| 8,770,458 B2 | 7/2014 | Scirica |
| 8,770,459 B2 | 7/2014 | Racenet et al. |
| 8,777,004 B2 | 7/2014 | Shelton, IV et al. |
| 8,783,541 B2 | 7/2014 | Shelton, IV et al. |
| 8,783,542 B2 | 7/2014 | Riestenberg et al. |
| 8,783,543 B2 | 7/2014 | Shelton, IV et al. |
| 8,789,737 B2 | 7/2014 | Hodgkinson et al. |
| 8,789,739 B2 | 7/2014 | Swensgard |
| 8,789,740 B2 | 7/2014 | Baxter, III et al. |
| 8,789,741 B2 | 7/2014 | Baxter, III et al. |
| 8,794,496 B2 | 8/2014 | Scirica |
| 8,794,497 B2 | 8/2014 | Zingman |
| 8,795,308 B2 | 8/2014 | Valin |
| 8,800,837 B2 | 8/2014 | Zemlok |
| 8,800,838 B2 | 8/2014 | Shelton, IV |
| 8,800,840 B2 | 8/2014 | Jankowski |
| 8,800,841 B2 | 8/2014 | Ellerhorst et al. |
| 8,801,734 B2 | 8/2014 | Shelton, IV et al. |
| 8,801,735 B2 | 8/2014 | Shelton, IV et al. |
| 8,801,752 B2 | 8/2014 | Fortier et al. |
| 8,806,973 B2 | 8/2014 | Ross et al. |
| 8,808,311 B2 | 8/2014 | Heinrich et al. |
| 8,814,024 B2 | 8/2014 | Woodard, Jr. et al. |
| 8,820,603 B2 | 9/2014 | Shelton, IV et al. |
| 8,820,605 B2 | 9/2014 | Shelton, IV |
| 8,827,133 B2 | 9/2014 | Shelton, IV et al. |
| 8,827,134 B2 | 9/2014 | Viola et al. |
| 8,827,903 B2 | 9/2014 | Shelton, IV et al. |
| 8,833,632 B2 | 9/2014 | Swensgard |
| 8,840,003 B2 | 9/2014 | Morgan et al. |
| 8,840,603 B2 | 9/2014 | Shelton, IV et al. |
| 8,844,789 B2 | 9/2014 | Shelton, IV et al. |
| 8,851,354 B2 | 10/2014 | Swensgard et al. |
| 8,857,693 B2 | 10/2014 | Schuckmann et al. |
| 8,857,694 B2 | 10/2014 | Shelton, IV et al. |
| 8,858,538 B2 | 10/2014 | Belson et al. |
| 8,858,571 B2 | 10/2014 | Shelton, IV et al. |
| 8,858,590 B2 | 10/2014 | Shelton, IV et al. |
| 8,864,007 B2 | 10/2014 | Widenhouse et al. |
| 8,864,009 B2 | 10/2014 | Shelton, IV et al. |
| 8,875,971 B2 | 11/2014 | Hall et al. |
| 8,875,972 B2 | 11/2014 | Weisenburgh, II et al. |
| 8,876,857 B2 | 11/2014 | Burbank |
| 8,893,946 B2 | 11/2014 | Boudreaux et al. |
| 8,893,949 B2 | 11/2014 | Shelton, IV et al. |
| 8,894,647 B2 | 11/2014 | Beardsley et al. |
| 8,899,463 B2 | 12/2014 | Schall et al. |
| 8,899,465 B2 | 12/2014 | Shelton, IV et al. |
| 8,899,466 B2 | 12/2014 | Baxter, III et al. |
| 8,905,977 B2 | 12/2014 | Shelton et al. |
| 8,911,471 B2 | 12/2014 | Spivey et al. |

(56) References Cited

U.S. PATENT DOCUMENTS

| | | |
|---|---|---|
| 8,920,435 B2 | 12/2014 | Smith et al. |
| 8,920,443 B2 | 12/2014 | Hiles et al. |
| 8,920,444 B2 | 12/2014 | Hiles et al. |
| 8,925,782 B2 | 1/2015 | Shelton, IV |
| 8,925,788 B2 | 1/2015 | Hess et al. |
| 8,926,598 B2 | 1/2015 | Mollere et al. |
| 8,931,682 B2 | 1/2015 | Timm et al. |
| 8,945,163 B2 | 2/2015 | Voegele et al. |
| 8,956,390 B2 | 2/2015 | Shah et al. |
| 8,967,443 B2 | 3/2015 | McCuen |
| 8,967,446 B2 | 3/2015 | Beardsley et al. |
| 8,973,803 B2 | 3/2015 | Hall et al. |
| 8,973,804 B2 | 3/2015 | Hess et al. |
| 8,974,440 B2 | 3/2015 | Farritor et al. |
| 8,978,954 B2 | 3/2015 | Shelton, IV et al. |
| 8,978,955 B2 | 3/2015 | Aronhalt et al. |
| 8,978,956 B2 | 3/2015 | Schall et al. |
| 8,991,676 B2 | 3/2015 | Hess et al. |
| 8,991,677 B2 | 3/2015 | Moore et al. |
| 8,992,422 B2 | 3/2015 | Spivey et al. |
| 8,998,058 B2 | 4/2015 | Moore et al. |
| 8,998,935 B2 | 4/2015 | Hart |
| 9,005,230 B2 | 4/2015 | Yates et al. |
| 9,005,238 B2 | 4/2015 | DeSantis et al. |
| 9,016,542 B2 | 4/2015 | Shelton, IV et al. |
| 9,028,494 B2 | 5/2015 | Shelton, IV et al. |
| 9,028,495 B2 | 5/2015 | Mueller et al. |
| 9,028,519 B2 | 5/2015 | Yates et al. |
| 9,033,203 B2 | 5/2015 | Woodard, Jr. et al. |
| 9,033,204 B2 | 5/2015 | Shelton, IV et al. |
| 9,044,227 B2 | 6/2015 | Shelton, IV et al. |
| 9,044,228 B2 | 6/2015 | Woodard, Jr. et al. |
| 9,044,229 B2 | 6/2015 | Scheib et al. |
| 9,044,230 B2 | 6/2015 | Morgan et al. |
| 9,050,083 B2 | 6/2015 | Yates et al. |
| 9,050,084 B2 | 6/2015 | Schmid et al. |
| 9,055,941 B2 | 6/2015 | Schmid et al. |
| 9,055,944 B2 | 6/2015 | Hodgkinson et al. |
| 9,060,770 B2 | 6/2015 | Shelton, IV et al. |
| 9,060,894 B2 | 6/2015 | Wubbeling |
| 9,072,515 B2 | 7/2015 | Hall et al. |
| 9,072,535 B2 | 7/2015 | Shelton, IV et al. |
| 9,072,536 B2 | 7/2015 | Shelton, IV et al. |
| 9,078,653 B2 | 7/2015 | Leimbach et al. |
| 9,084,601 B2 | 7/2015 | Moore et al. |
| 9,084,602 B2 | 7/2015 | Gleiman |
| 9,089,330 B2 | 7/2015 | Widenhouse et al. |
| 9,089,352 B2 | 7/2015 | Jeong |
| 9,095,339 B2 | 8/2015 | Moore et al. |
| 9,095,362 B2 | 8/2015 | Dachs, II et al. |
| 9,101,358 B2 | 8/2015 | Kerr et al. |
| 9,101,385 B2 | 8/2015 | Shelton, IV et al. |
| 9,107,663 B2 | 8/2015 | Swensgard |
| 9,113,862 B2 | 8/2015 | Morgan et al. |
| 9,113,864 B2 | 8/2015 | Morgan et al. |
| 9,113,865 B2 | 8/2015 | Shelton, IV et al. |
| 9,113,874 B2 | 8/2015 | Shelton, IV et al. |
| 9,113,880 B2 | 8/2015 | Zemlok et al. |
| 9,113,883 B2 | 8/2015 | Aronhalt et al. |
| 9,113,884 B2 | 8/2015 | Shelton, IV et al. |
| 9,119,657 B2 | 9/2015 | Shelton, IV et al. |
| 9,119,957 B2 | 9/2015 | Gantz et al. |
| 9,125,654 B2 | 9/2015 | Aronhalt et al. |
| 9,125,662 B2 | 9/2015 | Shelton, IV |
| 9,131,940 B2 | 9/2015 | Huitema et al. |
| 9,138,225 B2 | 9/2015 | Huang et al. |
| 9,149,274 B2 | 10/2015 | Spivey et al. |
| 9,168,038 B2 | 10/2015 | Shelton, IV et al. |
| 9,179,911 B2 | 11/2015 | Morgan et al. |
| 9,179,912 B2 | 11/2015 | Yates et al. |
| 9,186,140 B2 | 11/2015 | Hiles et al. |
| 9,186,143 B2 | 11/2015 | Timm et al. |
| 9,198,661 B2 | 12/2015 | Swensgard |
| 9,198,662 B2 | 12/2015 | Barton et al. |
| 9,204,878 B2 | 12/2015 | Hall et al. |
| 9,204,879 B2 | 12/2015 | Shelton, IV |
| 9,204,880 B2 | 12/2015 | Baxter, III et al. |
| 9,211,120 B2 | 12/2015 | Scheib et al. |
| 9,211,121 B2 | 12/2015 | Hall et al. |
| 9,211,122 B2 | 12/2015 | Hagerty et al. |
| 9,216,019 B2 | 12/2015 | Schmid et al. |
| 9,220,500 B2 | 12/2015 | Swayze et al. |
| 9,220,501 B2 | 12/2015 | Baxter, III et al. |
| 9,220,559 B2 | 12/2015 | Worrell et al. |
| 9,226,751 B2 | 1/2016 | Shelton, IV et al. |
| 9,232,941 B2 | 1/2016 | Mandakolathur Vasudevan et al. |
| 9,232,945 B2 | 1/2016 | Zingman |
| 9,237,891 B2 | 1/2016 | Shelton, IV |
| 9,241,714 B2 | 1/2016 | Timm et al. |
| 9,271,799 B2 | 3/2016 | Shelton, IV et al. |
| 9,272,406 B2 | 3/2016 | Aronhalt et al. |
| 9,277,919 B2 | 3/2016 | Timmer et al. |
| 9,282,962 B2 | 3/2016 | Schmid et al. |
| 9,282,966 B2 | 3/2016 | Shelton, IV et al. |
| 9,282,974 B2 | 3/2016 | Shelton, IV |
| 9,283,054 B2 | 3/2016 | Morgan et al. |
| 9,289,206 B2 | 3/2016 | Hess et al. |
| 9,289,210 B2 | 3/2016 | Baxter, III et al. |
| 9,289,212 B2 | 3/2016 | Shelton, IV et al. |
| 9,289,225 B2 | 3/2016 | Shelton, IV et al. |
| 9,289,256 B2 | 3/2016 | Shelton, IV et al. |
| 9,295,464 B2 | 3/2016 | Shelton, IV et al. |
| 9,301,752 B2 | 4/2016 | Mandakolathur Vasudevan et al. |
| 9,301,753 B2 | 4/2016 | Aldridge et al. |
| 9,301,755 B2 | 4/2016 | Shelton, IV et al. |
| 9,301,759 B2 | 4/2016 | Spivey et al. |
| 9,307,965 B2 | 4/2016 | Ming et al. |
| 9,307,986 B2 | 4/2016 | Hall et al. |
| 9,307,987 B2 | 4/2016 | Swensgard et al. |
| 9,307,988 B2 | 4/2016 | Shelton, IV |
| 9,307,989 B2 | 4/2016 | Shelton, IV et al. |
| 9,307,994 B2 | 4/2016 | Gresham et al. |
| 9,314,246 B2 | 4/2016 | Shelton, IV et al. |
| 9,314,247 B2 | 4/2016 | Shelton, IV et al. |
| 9,320,518 B2 | 4/2016 | Henderson et al. |
| 9,320,521 B2 | 4/2016 | Shelton, IV et al. |
| 9,320,523 B2 | 4/2016 | Shelton, IV et al. |
| 9,326,767 B2 | 5/2016 | Koch et al. |
| 9,326,768 B2 | 5/2016 | Shelton, IV |
| 9,326,769 B2 | 5/2016 | Shelton, IV et al. |
| 9,326,770 B2 | 5/2016 | Shelton, IV et al. |
| 9,326,771 B2 | 5/2016 | Baxter, III et al. |
| 9,332,974 B2 | 5/2016 | Henderson et al. |
| 9,332,984 B2 | 5/2016 | Weaner et al. |
| 9,332,987 B2 | 5/2016 | Leimbach et al. |
| 9,345,477 B2 | 5/2016 | Anim et al. |
| 9,345,481 B2 | 5/2016 | Hall et al. |
| 9,351,726 B2 | 5/2016 | Leimbach et al. |
| 9,351,727 B2 | 5/2016 | Leimbach et al. |
| 9,351,730 B2 | 5/2016 | Schmid et al. |
| 9,358,003 B2 | 6/2016 | Hall et al. |
| 9,364,230 B2 | 6/2016 | Shelton, IV et al. |
| 9,364,233 B2 | 6/2016 | Alexander, III et al. |
| 9,370,358 B2 | 6/2016 | Shelton, IV et al. |
| 9,370,364 B2 | 6/2016 | Smith et al. |
| 9,386,983 B2 | 7/2016 | Swensgard et al. |
| 9,386,984 B2 | 7/2016 | Aronhalt et al. |
| 9,386,985 B2 | 7/2016 | Koch, Jr. et al. |
| 9,386,988 B2 | 7/2016 | Baxter, III et al. |
| 9,393,015 B2 | 7/2016 | Laurent et al. |
| 9,398,911 B2 | 7/2016 | Auld |
| 9,402,626 B2 | 8/2016 | Ortiz et al. |
| 9,408,604 B2 | 8/2016 | Shelton, IV et al. |
| 9,408,606 B2 | 8/2016 | Shelton, IV |
| 9,414,838 B2 | 8/2016 | Shelton, IV et al. |
| 9,427,223 B2 | 8/2016 | Park et al. |
| 9,433,419 B2 | 9/2016 | Gonzalez et al. |
| 9,439,649 B2 | 9/2016 | Shelton, IV et al. |
| 9,439,651 B2 | 9/2016 | Smith et al. |
| 9,445,813 B2 | 9/2016 | Shelton, IV et al. |
| 9,451,958 B2 | 9/2016 | Shelton, IV et al. |
| 9,463,260 B2 | 10/2016 | Stopek |
| 9,468,438 B2 | 10/2016 | Baber et al. |
| 9,480,476 B2 | 11/2016 | Aldridge et al. |

(56) References Cited

U.S. PATENT DOCUMENTS

| | | |
|---|---|---|
| 9,486,214 B2 | 11/2016 | Shelton, IV |
| 9,486,302 B2 | 11/2016 | Boey et al. |
| 9,492,167 B2 | 11/2016 | Shelton, IV et al. |
| 9,492,170 B2 | 11/2016 | Bear et al. |
| 9,510,828 B2 | 12/2016 | Yates et al. |
| 9,510,830 B2 | 12/2016 | Shelton, IV et al. |
| 9,510,925 B2 | 12/2016 | Hotter et al. |
| 9,517,063 B2 | 12/2016 | Swayze et al. |
| 9,517,068 B2 | 12/2016 | Shelton, IV et al. |
| 9,522,029 B2 | 12/2016 | Yates et al. |
| 9,549,732 B2 | 1/2017 | Yates et al. |
| 9,549,735 B2 | 1/2017 | Shelton, IV et al. |
| 9,554,794 B2 | 1/2017 | Baber et al. |
| 9,561,032 B2 | 2/2017 | Shelton, IV et al. |
| 9,561,038 B2 | 2/2017 | Shelton, IV et al. |
| 9,566,061 B2 | 2/2017 | Aronhalt et al. |
| 9,572,577 B2 | 2/2017 | Lloyd et al. |
| 9,574,644 B2 | 2/2017 | Parihar |
| 9,585,657 B2 | 3/2017 | Shelton, IV et al. |
| 9,585,660 B2 | 3/2017 | Laurent et al. |
| 9,585,662 B2 | 3/2017 | Shelton, IV et al. |
| 9,592,050 B2 | 3/2017 | Schmid et al. |
| 9,592,052 B2 | 3/2017 | Shelton, IV |
| 9,592,053 B2 | 3/2017 | Shelton, IV et al. |
| 9,592,054 B2 | 3/2017 | Schmid et al. |
| 9,597,075 B2 | 3/2017 | Shelton, IV et al. |
| 9,597,080 B2 | 3/2017 | Milliman et al. |
| 9,603,595 B2 | 3/2017 | Shelton, IV et al. |
| 9,603,598 B2 | 3/2017 | Shelton, IV et al. |
| 9,603,991 B2 | 3/2017 | Shelton, IV et al. |
| 9,615,826 B2 | 4/2017 | Shelton, IV et al. |
| 9,629,623 B2 | 4/2017 | Lytle, IV et al. |
| 9,629,626 B2 | 4/2017 | Soltz et al. |
| 9,629,629 B2 | 4/2017 | Leimbach et al. |
| 9,629,814 B2 | 4/2017 | Widenhouse et al. |
| 9,642,620 B2 | 5/2017 | Baxter, III et al. |
| 9,649,110 B2 | 5/2017 | Parihar et al. |
| 9,649,111 B2 | 5/2017 | Shelton, IV et al. |
| 9,655,614 B2 | 5/2017 | Swensgard et al. |
| 9,655,624 B2 | 5/2017 | Shelton, IV et al. |
| 9,675,355 B2 | 6/2017 | Shelton, IV et al. |
| 9,675,372 B2 | 6/2017 | Laurent et al. |
| 9,675,375 B2 | 6/2017 | Houser et al. |
| 9,681,870 B2 | 6/2017 | Baxter, III et al. |
| 9,681,873 B2 | 6/2017 | Smith et al. |
| 9,687,230 B2 | 6/2017 | Leimbach et al. |
| 9,687,231 B2 | 6/2017 | Baxter, III et al. |
| 9,687,232 B2 | 6/2017 | Shelton, IV et al. |
| 9,687,236 B2 | 6/2017 | Leimbach et al. |
| 9,693,777 B2 | 7/2017 | Schellin et al. |
| 9,700,309 B2 | 7/2017 | Jaworek et al. |
| 9,700,310 B2 | 7/2017 | Morgan et al. |
| 9,700,317 B2 | 7/2017 | Aronhalt et al. |
| 9,700,321 B2 | 7/2017 | Shelton, IV et al. |
| 9,706,991 B2 | 7/2017 | Hess et al. |
| 9,724,091 B2 | 8/2017 | Shelton, IV et al. |
| 9,724,092 B2 | 8/2017 | Baxter, III et al. |
| 9,724,098 B2 | 8/2017 | Baxter, III et al. |
| 9,730,692 B2 | 8/2017 | Shelton, IV et al. |
| 9,730,697 B2 | 8/2017 | Morgan et al. |
| 9,743,928 B2 | 8/2017 | Shelton, IV et al. |
| 9,757,123 B2 | 9/2017 | Giordano et al. |
| 9,757,124 B2 | 9/2017 | Schellin et al. |
| 9,757,130 B2 | 9/2017 | Shelton, IV |
| 9,763,662 B2 | 9/2017 | Shelton, IV et al. |
| 9,775,608 B2 | 10/2017 | Aronhalt et al. |
| 9,775,609 B2 | 10/2017 | Shelton, IV et al. |
| 9,775,613 B2 | 10/2017 | Shelton, IV et al. |
| 9,782,169 B2 | 10/2017 | Kimsey et al. |
| 9,788,834 B2 | 10/2017 | Schmid et al. |
| 9,795,382 B2 | 10/2017 | Shelton, IV |
| 9,795,384 B2 | 10/2017 | Weaner et al. |
| 9,801,626 B2 | 10/2017 | Parihar et al. |
| 9,801,634 B2 | 10/2017 | Shelton, IV et al. |
| 9,808,244 B2 | 11/2017 | Leimbach et al. |
| 9,808,249 B2 | 11/2017 | Shelton, IV |
| 9,814,460 B2 | 11/2017 | Kimsey et al. |
| 9,814,462 B2 | 11/2017 | Woodard, Jr. et al. |
| 9,826,976 B2 | 11/2017 | Parihar et al. |
| 9,826,978 B2 | 11/2017 | Shelton, IV et al. |
| 9,833,236 B2 | 12/2017 | Shelton, IV et al. |
| 9,839,420 B2 | 12/2017 | Shelton, IV et al. |
| 9,839,422 B2 | 12/2017 | Schellin et al. |
| 9,839,423 B2 | 12/2017 | Vendely et al. |
| 9,839,427 B2 | 12/2017 | Swayze et al. |
| 9,839,428 B2 | 12/2017 | Baxter, III et al. |
| 9,844,368 B2 | 12/2017 | Boudreaux et al. |
| 9,844,373 B2 | 12/2017 | Swayze et al. |
| 9,848,873 B2 | 12/2017 | Shelton, IV |
| 9,848,875 B2 | 12/2017 | Aronhalt et al. |
| 9,861,359 B2 | 1/2018 | Shelton, IV et al. |
| 9,861,361 B2 | 1/2018 | Aronhalt et al. |
| 9,867,612 B2 | 1/2018 | Parihar et al. |
| 9,883,860 B2 | 2/2018 | Leimbach |
| 9,884,456 B2 | 2/2018 | Schellin et al. |
| 9,888,919 B2 | 2/2018 | Leimbach et al. |
| 9,888,924 B2 | 2/2018 | Ebersole et al. |
| 9,895,147 B2 | 2/2018 | Shelton, IV |
| 9,913,647 B2 | 3/2018 | Weisenburgh, II et al. |
| 9,918,704 B2 | 3/2018 | Shelton, IV et al. |
| 9,918,716 B2 | 3/2018 | Baxter, III et al. |
| 9,924,942 B2 | 3/2018 | Swayze et al. |
| 9,924,947 B2 | 3/2018 | Shelton, IV et al. |
| 9,968,354 B2 | 5/2018 | Shelton, IV et al. |
| 9,968,356 B2 | 5/2018 | Shelton, IV et al. |
| 9,974,529 B2 | 5/2018 | Shelton, IV et al. |
| 9,974,538 B2 | 5/2018 | Baxter, III et al. |
| 9,980,630 B2 | 5/2018 | Larkin et al. |
| 9,980,713 B2 | 5/2018 | Aronhalt et al. |
| 9,987,006 B2 | 6/2018 | Morgan et al. |
| 10,004,498 B2 | 6/2018 | Morgan et al. |
| 10,010,322 B2 | 7/2018 | Shelton, IV et al. |
| 10,028,742 B2 | 7/2018 | Shelton, IV et al. |
| 10,039,529 B2 | 8/2018 | Kerr et al. |
| 10,052,099 B2 | 8/2018 | Morgan et al. |
| 10,052,100 B2 | 8/2018 | Morgan et al. |
| 10,058,963 B2 | 8/2018 | Shelton, IV et al. |
| 10,064,624 B2 | 9/2018 | Shelton, IV et al. |
| 10,070,861 B2 | 9/2018 | Spivey et al. |
| 10,070,863 B2 | 9/2018 | Swayze et al. |
| 10,071,452 B2 | 9/2018 | Shelton, IV et al. |
| 10,085,806 B2 | 10/2018 | Hagn et al. |
| 10,123,798 B2 | 11/2018 | Baxter, III et al. |
| 10,130,359 B2 | 11/2018 | Hess et al. |
| 10,130,363 B2 * | 11/2018 | Huitema ............ A61B 17/07207 |
| 10,130,366 B2 | 11/2018 | Shelton, IV et al. |
| 10,136,887 B2 | 11/2018 | Shelton, IV et al. |
| 10,136,890 B2 | 11/2018 | Shelton, IV et al. |
| 10,149,679 B2 | 12/2018 | Shelton, IV et al. |
| 10,149,680 B2 | 12/2018 | Parihar et al. |
| 10,159,482 B2 | 12/2018 | Swayze et al. |
| 10,172,616 B2 | 1/2019 | Murray et al. |
| 10,213,198 B2 | 2/2019 | Aronhalt et al. |
| 10,238,385 B2 | 3/2019 | Yates et al. |
| 10,265,065 B2 | 4/2019 | Shelton, IV et al. |
| 10,335,144 B2 | 7/2019 | Shelton, IV et al. |
| 10,342,533 B2 | 7/2019 | Shelton, IV et al. |
| 10,390,823 B2 | 8/2019 | Shelton, IV et al. |
| 10,398,433 B2 | 9/2019 | Boudreaux et al. |
| 10,405,854 B2 | 9/2019 | Schmid et al. |
| 10,405,857 B2 | 9/2019 | Shelton, IV et al. |
| 10,433,918 B2 | 10/2019 | Shelton, IV et al. |
| 10,441,285 B2 | 10/2019 | Shelton, IV et al. |
| 10,441,369 B2 | 10/2019 | Shelton, IV et al. |
| 10,456,133 B2 | 10/2019 | Yates et al. |
| 10,470,762 B2 | 11/2019 | Leimbach et al. |
| 10,470,763 B2 | 11/2019 | Yates et al. |
| 10,517,682 B2 | 12/2019 | Giordano et al. |
| 10,595,835 B2 | 3/2020 | Kerr et al. |
| 10,624,634 B2 | 4/2020 | Shelton, IV et al. |
| 2002/0103494 A1 | 8/2002 | Pacey |
| 2002/0117534 A1 | 8/2002 | Green et al. |
| 2003/0009193 A1 | 1/2003 | Corsaro |
| 2003/0039689 A1 | 2/2003 | Chen et al. |

(56) References Cited

U.S. PATENT DOCUMENTS

| | | |
|---|---|---|
| 2003/0096158 A1 | 5/2003 | Takano et al. |
| 2003/0181900 A1 | 9/2003 | Long |
| 2003/0236505 A1 | 12/2003 | Bonadio et al. |
| 2004/0034357 A1 | 2/2004 | Beane et al. |
| 2004/0068161 A1 | 4/2004 | Couvillon |
| 2004/0068224 A1 | 4/2004 | Couvillon et al. |
| 2004/0073222 A1 | 4/2004 | Koseki |
| 2004/0102783 A1 | 5/2004 | Sutterlin et al. |
| 2004/0108357 A1 | 6/2004 | Milliman et al. |
| 2004/0115022 A1 | 6/2004 | Albertson et al. |
| 2004/0147909 A1 | 7/2004 | Johnston et al. |
| 2004/0164123 A1 | 8/2004 | Racenet et al. |
| 2004/0167572 A1 | 8/2004 | Roth et al. |
| 2004/0193189 A1 | 9/2004 | Kortenbach et al. |
| 2004/0222268 A1 | 11/2004 | Bilotti et al. |
| 2004/0225186 A1 | 11/2004 | Horne et al. |
| 2004/0232201 A1 | 11/2004 | Wenchell et al. |
| 2004/0260315 A1 | 12/2004 | Dell et al. |
| 2004/0267310 A1 | 12/2004 | Racenet et al. |
| 2005/0059997 A1 | 3/2005 | Bauman et al. |
| 2005/0070929 A1 | 3/2005 | Dalessandro et al. |
| 2005/0080342 A1 | 4/2005 | Gilreath et al. |
| 2005/0090817 A1 | 4/2005 | Phan |
| 2005/0125897 A1 | 6/2005 | Wyslucha et al. |
| 2005/0139636 A1 | 6/2005 | Schwemberger et al. |
| 2005/0143759 A1 | 6/2005 | Kelly |
| 2005/0154406 A1 | 7/2005 | Bombard et al. |
| 2005/0169974 A1 | 8/2005 | Tenerz et al. |
| 2005/0177181 A1 | 8/2005 | Kagan et al. |
| 2005/0184121 A1 | 8/2005 | Heinrich |
| 2005/0203550 A1 | 9/2005 | Laufer et al. |
| 2005/0228224 A1 | 10/2005 | Okada et al. |
| 2005/0245965 A1 | 11/2005 | Orban, III et al. |
| 2005/0263563 A1 | 12/2005 | Racenet et al. |
| 2006/0049229 A1 | 3/2006 | Milliman et al. |
| 2006/0052825 A1 | 3/2006 | Ransick et al. |
| 2006/0064086 A1 | 3/2006 | Odom |
| 2006/0089535 A1 | 4/2006 | Raz et al. |
| 2006/0173470 A1 | 8/2006 | Oray et al. |
| 2006/0180634 A1 | 8/2006 | Shelton et al. |
| 2006/0201989 A1 | 9/2006 | Ojeda |
| 2006/0235368 A1 | 10/2006 | Oz |
| 2006/0271042 A1 | 11/2006 | Latterell et al. |
| 2006/0271102 A1 | 11/2006 | Bosshard et al. |
| 2006/0287576 A1 | 12/2006 | Tsuji et al. |
| 2006/0289602 A1 | 12/2006 | Wales et al. |
| 2006/0291981 A1 | 12/2006 | Viola et al. |
| 2007/0027468 A1 | 2/2007 | Wales et al. |
| 2007/0051375 A1 | 3/2007 | Milliman |
| 2007/0084897 A1 | 4/2007 | Shelton et al. |
| 2007/0093869 A1 | 4/2007 | Bloom et al. |
| 2007/0102472 A1 | 5/2007 | Shelton |
| 2007/0106317 A1 | 5/2007 | Shelton et al. |
| 2007/0134251 A1 | 6/2007 | Ashkenazi et al. |
| 2007/0170225 A1 | 7/2007 | Shelton et al. |
| 2007/0173687 A1 | 7/2007 | Shima et al. |
| 2007/0173813 A1 | 7/2007 | Odom |
| 2007/0175950 A1 | 8/2007 | Shelton et al. |
| 2007/0175951 A1 | 8/2007 | Shelton et al. |
| 2007/0175955 A1 | 8/2007 | Shelton et al. |
| 2007/0194079 A1 | 8/2007 | Hueil et al. |
| 2007/0194082 A1 | 8/2007 | Morgan et al. |
| 2007/0203510 A1 | 8/2007 | Bettuchi |
| 2007/0225562 A1 | 9/2007 | Spivey et al. |
| 2007/0243227 A1 | 10/2007 | Gertner |
| 2007/0246505 A1 | 10/2007 | Pace-Floridia et al. |
| 2007/0276409 A1 | 11/2007 | Ortiz et al. |
| 2007/0279011 A1 | 12/2007 | Jones et al. |
| 2007/0286892 A1 | 12/2007 | Herzberg et al. |
| 2008/0029570 A1 | 2/2008 | Shelton et al. |
| 2008/0029573 A1 | 2/2008 | Shelton et al. |
| 2008/0029574 A1 | 2/2008 | Shelton et al. |
| 2008/0029575 A1 | 2/2008 | Shelton et al. |
| 2008/0078802 A1 | 4/2008 | Hess et al. |
| 2008/0082125 A1 | 4/2008 | Murray et al. |
| 2008/0082126 A1 | 4/2008 | Murray et al. |
| 2008/0086078 A1 | 4/2008 | Powell et al. |
| 2008/0091072 A1 | 4/2008 | Omori et al. |
| 2008/0128469 A1 | 6/2008 | Dalessandro et al. |
| 2008/0135600 A1 | 6/2008 | Hiranuma et al. |
| 2008/0140115 A1 | 6/2008 | Stopek |
| 2008/0169328 A1 | 7/2008 | Shelton |
| 2008/0169332 A1 | 7/2008 | Shelton et al. |
| 2008/0169333 A1 | 7/2008 | Shelton et al. |
| 2008/0172087 A1 | 7/2008 | Fuchs et al. |
| 2008/0197167 A1 | 8/2008 | Viola et al. |
| 2008/0200762 A1 | 8/2008 | Stokes et al. |
| 2008/0249536 A1 | 10/2008 | Stahler et al. |
| 2008/0296346 A1 | 12/2008 | Shelton, IV et al. |
| 2008/0308602 A1 | 12/2008 | Timm et al. |
| 2008/0308603 A1 | 12/2008 | Shelton et al. |
| 2008/0315829 A1 | 12/2008 | Jones et al. |
| 2009/0001121 A1 | 1/2009 | Hess et al. |
| 2009/0001130 A1 | 1/2009 | Hess et al. |
| 2009/0005809 A1 | 1/2009 | Hess et al. |
| 2009/0048589 A1 | 2/2009 | Takashino et al. |
| 2009/0078736 A1 | 3/2009 | Van Lue |
| 2009/0090763 A1 | 4/2009 | Zemlok et al. |
| 2009/0099876 A1 | 4/2009 | Whitman |
| 2009/0149871 A9 | 6/2009 | Kagan et al. |
| 2009/0188964 A1 | 7/2009 | Orlov |
| 2009/0204108 A1 | 8/2009 | Steffen |
| 2009/0206125 A1 | 8/2009 | Huitema et al. |
| 2009/0206126 A1 | 8/2009 | Huitema et al. |
| 2009/0206131 A1 | 8/2009 | Weisenburgh, II et al. |
| 2009/0206133 A1 | 8/2009 | Morgan et al. |
| 2009/0206137 A1 | 8/2009 | Hall et al. |
| 2009/0206139 A1 | 8/2009 | Hall et al. |
| 2009/0206141 A1 | 8/2009 | Huitema et al. |
| 2009/0206142 A1 | 8/2009 | Huitema et al. |
| 2009/0242610 A1 | 10/2009 | Shelton, IV et al. |
| 2009/0255974 A1 | 10/2009 | Viola |
| 2009/0292283 A1 | 11/2009 | Odom |
| 2010/0069942 A1 | 3/2010 | Shelton, IV |
| 2010/0133317 A1 | 6/2010 | Shelton, IV et al. |
| 2010/0147921 A1 | 6/2010 | Olson |
| 2010/0147922 A1 | 6/2010 | Olson |
| 2010/0193566 A1 | 8/2010 | Scheib et al. |
| 2010/0222901 A1 | 9/2010 | Swayze et al. |
| 2011/0006101 A1 | 1/2011 | Hall et al. |
| 2011/0011916 A1 | 1/2011 | Levine |
| 2011/0024477 A1 | 2/2011 | Hall |
| 2011/0024478 A1 | 2/2011 | Shelton, IV |
| 2011/0060363 A1 | 3/2011 | Hess et al. |
| 2011/0087276 A1 | 4/2011 | Bedi et al. |
| 2011/0091515 A1 | 4/2011 | Zilberman et al. |
| 2011/0114697 A1 | 5/2011 | Baxter, III et al. |
| 2011/0125176 A1 | 5/2011 | Yates et al. |
| 2011/0147433 A1 | 6/2011 | Shelton, IV et al. |
| 2011/0163146 A1 | 7/2011 | Ortiz et al. |
| 2011/0174861 A1 | 7/2011 | Shelton, IV et al. |
| 2011/0192882 A1 | 8/2011 | Hess et al. |
| 2011/0275901 A1 | 11/2011 | Shelton, IV |
| 2011/0276083 A1 | 11/2011 | Shelton, IV et al. |
| 2011/0278343 A1 | 11/2011 | Knodel et al. |
| 2011/0290856 A1 | 12/2011 | Shelton, IV et al. |
| 2011/0293690 A1 | 12/2011 | Griffin et al. |
| 2011/0295295 A1 | 12/2011 | Shelton, IV et al. |
| 2012/0029272 A1 | 2/2012 | Shelton, IV et al. |
| 2012/0074200 A1 | 3/2012 | Schmid et al. |
| 2012/0080336 A1 | 4/2012 | Shelton, IV et al. |
| 2012/0080344 A1 | 4/2012 | Shelton, IV |
| 2012/0080478 A1 | 4/2012 | Morgan et al. |
| 2012/0080498 A1 | 4/2012 | Shelton, IV et al. |
| 2012/0109186 A1 | 5/2012 | Parrott et al. |
| 2012/0125792 A1 | 5/2012 | Cassivi |
| 2012/0234895 A1 | 9/2012 | O'Connor et al. |
| 2012/0234897 A1 | 9/2012 | Shelton, IV et al. |
| 2012/0248169 A1 | 10/2012 | Widenhouse et al. |
| 2012/0283707 A1 | 11/2012 | Giordano et al. |
| 2012/0289979 A1 | 11/2012 | Eskaros et al. |
| 2012/0292367 A1 | 11/2012 | Morgan et al. |
| 2012/0298722 A1 | 11/2012 | Hess et al. |
| 2013/0020375 A1 | 1/2013 | Shelton, IV et al. |

(56) References Cited

U.S. PATENT DOCUMENTS

| | | |
|---|---|---|
| 2013/0020376 A1 | 1/2013 | Shelton, IV et al. |
| 2013/0023861 A1 | 1/2013 | Shelton, IV et al. |
| 2013/0026208 A1 | 1/2013 | Shelton, IV et al. |
| 2013/0026210 A1 | 1/2013 | Shelton, IV et al. |
| 2013/0087597 A1 | 4/2013 | Shelton, IV et al. |
| 2013/0116669 A1 | 5/2013 | Shelton, IV et al. |
| 2013/0153641 A1 | 6/2013 | Shelton, IV et al. |
| 2013/0175317 A1 | 7/2013 | Yates et al. |
| 2013/0233906 A1 | 9/2013 | Hess et al. |
| 2013/0256373 A1 | 10/2013 | Schmid et al. |
| 2013/0256380 A1 | 10/2013 | Schmid et al. |
| 2013/0270322 A1 | 10/2013 | Scheib et al. |
| 2013/0334283 A1 | 12/2013 | Swayze et al. |
| 2013/0334285 A1 | 12/2013 | Swayze et al. |
| 2013/0341374 A1 | 12/2013 | Shelton, IV et al. |
| 2014/0001231 A1 | 1/2014 | Shelton, IV et al. |
| 2014/0001234 A1 | 1/2014 | Shelton, IV et al. |
| 2014/0005640 A1 | 1/2014 | Shelton, IV et al. |
| 2014/0005678 A1 | 1/2014 | Shelton, IV et al. |
| 2014/0005718 A1 | 1/2014 | Shelton, IV et al. |
| 2014/0014705 A1 | 1/2014 | Baxter, III |
| 2014/0048580 A1 | 2/2014 | Merchant et al. |
| 2014/0151433 A1 | 6/2014 | Shelton, IV et al. |
| 2014/0175152 A1 | 6/2014 | Hess et al. |
| 2014/0224857 A1 | 8/2014 | Schmid |
| 2014/0243865 A1 | 8/2014 | Swayze et al. |
| 2014/0246475 A1 | 9/2014 | Hall et al. |
| 2014/0249557 A1 | 9/2014 | Koch et al. |
| 2014/0263541 A1 | 9/2014 | Leimbach et al. |
| 2014/0263552 A1 | 9/2014 | Hall et al. |
| 2014/0284371 A1 | 9/2014 | Morgan et al. |
| 2014/0291379 A1 | 10/2014 | Schellin et al. |
| 2014/0291383 A1 | 10/2014 | Spivey et al. |
| 2014/0299648 A1 | 10/2014 | Shelton, IV et al. |
| 2014/0303645 A1 | 10/2014 | Morgan et al. |
| 2014/0330161 A1 | 11/2014 | Swayze et al. |
| 2015/0008248 A1 | 1/2015 | Giordano et al. |
| 2015/0053737 A1 | 2/2015 | Leimbach et al. |
| 2015/0053743 A1 | 2/2015 | Yates et al. |
| 2015/0053746 A1 | 2/2015 | Shelton, IV et al. |
| 2015/0053748 A1 | 2/2015 | Yates et al. |
| 2015/0060518 A1 | 3/2015 | Shelton, IV et al. |
| 2015/0060519 A1 | 3/2015 | Shelton, IV et al. |
| 2015/0060520 A1 | 3/2015 | Shelton, IV et al. |
| 2015/0060521 A1 | 3/2015 | Weisenburgh, II et al. |
| 2015/0076208 A1 | 3/2015 | Shelton, IV |
| 2015/0076209 A1 | 3/2015 | Shelton, IV et al. |
| 2015/0076210 A1 | 3/2015 | Shelton, IV et al. |
| 2015/0076212 A1 | 3/2015 | Shelton, IV |
| 2015/0083781 A1 | 3/2015 | Giordano et al. |
| 2015/0083782 A1 | 3/2015 | Scheib et al. |
| 2015/0090760 A1 | 4/2015 | Giordano et al. |
| 2015/0090762 A1 | 4/2015 | Giordano et al. |
| 2015/0173749 A1 | 6/2015 | Shelton, IV et al. |
| 2015/0173756 A1 | 6/2015 | Baxter, III et al. |
| 2015/0173789 A1 | 6/2015 | Baxter, III et al. |
| 2015/0196295 A1 | 7/2015 | Shelton, IV et al. |
| 2015/0196296 A1 | 7/2015 | Swayze et al. |
| 2015/0196299 A1 | 7/2015 | Swayze et al. |
| 2015/0201932 A1 | 7/2015 | Swayze et al. |
| 2015/0201936 A1 | 7/2015 | Swayze et al. |
| 2015/0201937 A1 | 7/2015 | Swayze et al. |
| 2015/0201938 A1 | 7/2015 | Swayze et al. |
| 2015/0201939 A1 | 7/2015 | Swayze et al. |
| 2015/0201940 A1 | 7/2015 | Swayze et al. |
| 2015/0201941 A1 | 7/2015 | Swayze et al. |

FOREIGN PATENT DOCUMENTS

| | | |
|---|---|---|
| CN | 1634601 A | 7/2005 |
| CN | 2716900 Y | 8/2005 |
| CN | 2738962 Y | 11/2005 |
| DE | 273689 C | 5/1914 |
| DE | 1775926 A | 1/1972 |
| DE | 3036217 A1 | 4/1982 |
| DE | 3210466 A1 | 9/1983 |
| DE | 3709067 A1 | 9/1988 |
| DE | 19851291 A1 | 1/2000 |
| DE | 19924311 A1 | 11/2000 |
| DE | 20016423 U1 | 2/2001 |
| DE | 20112837 U1 | 10/2001 |
| DE | 20121753 U1 | 4/2003 |
| DE | 10314072 A1 | 10/2004 |
| DE | 202007003114 U1 | 6/2007 |
| EP | 0000756 A1 | 2/1979 |
| EP | 0122046 A1 | 10/1984 |
| EP | 0129442 B1 | 11/1987 |
| EP | 0169044 B1 | 6/1991 |
| EP | 0594148 A1 | 4/1994 |
| EP | 0646357 A1 | 4/1995 |
| EP | 0505036 B1 | 5/1995 |
| EP | 0669104 A1 | 8/1995 |
| EP | 0705571 A1 | 4/1996 |
| EP | 0528478 B1 | 5/1996 |
| EP | 0770355 A1 | 5/1997 |
| EP | 0625335 B1 | 11/1997 |
| EP | 0879742 A1 | 11/1998 |
| EP | 0650701 B1 | 3/1999 |
| EP | 0923907 A1 | 6/1999 |
| EP | 0484677 B2 | 7/2000 |
| EP | 1034747 A1 | 9/2000 |
| EP | 1034748 A1 | 9/2000 |
| EP | 1053719 A1 | 11/2000 |
| EP | 1055399 A1 | 11/2000 |
| EP | 1055400 A1 | 11/2000 |
| EP | 1080694 A1 | 3/2001 |
| EP | 1090592 A1 | 4/2001 |
| EP | 1095627 A1 | 5/2001 |
| EP | 0806914 B1 | 9/2001 |
| EP | 1284120 A1 | 2/2003 |
| EP | 0869742 B1 | 5/2003 |
| EP | 1374788 A1 | 1/2004 |
| EP | 1407719 A2 | 4/2004 |
| EP | 0996378 B1 | 6/2004 |
| EP | 1157666 B1 | 9/2005 |
| EP | 0880338 B1 | 10/2005 |
| EP | 1158917 B1 | 11/2005 |
| EP | 1344498 B1 | 11/2005 |
| EP | 1330989 B1 | 12/2005 |
| EP | 1632191 A2 | 3/2006 |
| EP | 1082944 B1 | 5/2006 |
| EP | 1253866 B1 | 7/2006 |
| EP | 1285633 B1 | 12/2006 |
| EP | 1011494 B1 | 1/2007 |
| EP | 1767163 A1 | 3/2007 |
| EP | 1837041 A1 | 9/2007 |
| EP | 0922435 B1 | 10/2007 |
| EP | 1599146 B1 | 10/2007 |
| EP | 1330201 B1 | 6/2008 |
| EP | 2039302 A2 | 3/2009 |
| EP | 1719461 B1 | 6/2009 |
| EP | 1769754 B1 | 6/2010 |
| EP | 1627605 B1 | 12/2010 |
| EP | 2316345 A1 | 5/2011 |
| EP | 02462878 A1 | 6/2012 |
| EP | 2517638 A1 | 10/2012 |
| EP | 2649948 A1 | 10/2013 |
| FR | 459743 A | 11/1913 |
| FR | 999646 A | 2/1952 |
| FR | 1112936 A | 3/1956 |
| FR | 2598905 A1 | 11/1987 |
| FR | 2765794 A1 | 1/1999 |
| FR | 2815842 A1 | 5/2002 |
| GB | 939929 A | 10/1963 |
| GB | 1210522 A | 10/1970 |
| GB | 1217159 A | 12/1970 |
| GB | 1339394 A | 12/1973 |
| GB | 2024012 A | 1/1980 |
| GB | 2109241 A | 6/1983 |
| GB | 2272159 A | 5/1994 |
| GB | 2336214 A | 10/1999 |
| GR | 930100110 A | 11/1993 |
| JP | S5033988 U | 4/1975 |
| JP | S62170011 U | 10/1987 |

(56) References Cited

FOREIGN PATENT DOCUMENTS

| | | |
|---|---|---|
| JP | H04215747 A | 8/1992 |
| JP | H0584252 A | 4/1993 |
| JP | H05123325 A | 5/1993 |
| JP | H0630945 A | 2/1994 |
| JP | H06237937 A | 8/1994 |
| JP | H06327684 A | 11/1994 |
| JP | H07124166 A | 5/1995 |
| JP | H07255735 A | 10/1995 |
| JP | H07285089 A | 10/1995 |
| JP | H0833642 A | 2/1996 |
| JP | H08164141 A | 6/1996 |
| JP | H08182684 A | 7/1996 |
| JP | H08507708 A | 8/1996 |
| JP | H08229050 A | 9/1996 |
| JP | H10118090 A | 5/1998 |
| JP | 2000014632 A | 1/2000 |
| JP | 2000033071 A | 2/2000 |
| JP | 2000112002 A | 4/2000 |
| JP | 2000166932 A | 6/2000 |
| JP | 2000171730 A | 6/2000 |
| JP | 2000287987 A | 10/2000 |
| JP | 2000325303 A | 11/2000 |
| JP | 2001087272 A | 4/2001 |
| JP | 2001514541 A | 9/2001 |
| JP | 2001276091 A | 10/2001 |
| JP | 2002051974 A | 2/2002 |
| JP | 2002085415 A | 3/2002 |
| JP | 2002143078 A | 5/2002 |
| JP | 2002528161 A | 9/2002 |
| JP | 2002314298 A | 10/2002 |
| JP | 2003135473 A | 5/2003 |
| JP | 2003521301 A | 7/2003 |
| JP | 2004147701 A | 5/2004 |
| JP | 2004162035 A | 6/2004 |
| JP | 2004229976 A | 8/2004 |
| JP | 2005080702 A | 3/2005 |
| JP | 2005131163 A | 5/2005 |
| JP | 2005131164 A | 5/2005 |
| JP | 2005131173 A | 5/2005 |
| JP | 2005131211 A | 5/2005 |
| JP | 2005131212 A | 5/2005 |
| JP | 2005137423 A | 6/2005 |
| JP | 2005328882 A | 12/2005 |
| JP | 2005335432 A | 12/2005 |
| JP | 2005342267 A | 12/2005 |
| JP | 2006187649 A | 7/2006 |
| JP | 2006281405 A | 10/2006 |
| JP | 2006346445 A | 12/2006 |
| JP | 2009507526 A | 2/2009 |
| JP | 2009189838 A | 8/2009 |
| JP | 2009539420 A | 11/2009 |
| JP | 2010098844 A | 4/2010 |
| KR | 20110003229 A | 1/2011 |
| RU | 1814161 A1 | 5/1993 |
| RU | 2008830 C1 | 3/1994 |
| RU | 2052979 C1 | 1/1996 |
| RU | 2098025 C1 | 12/1997 |
| RU | 2141279 C1 | 11/1999 |
| RU | 2144791 C1 | 1/2000 |
| RU | 2181566 C2 | 4/2002 |
| RU | 2187249 C2 | 8/2002 |
| RU | 32984 U1 | 10/2003 |
| RU | 2225170 C2 | 3/2004 |
| RU | 42750 U1 | 12/2004 |
| RU | 61114 U1 | 2/2007 |
| SU | 189517 A | 1/1967 |
| SU | 328636 A | 9/1972 |
| SU | 674747 A1 | 7/1979 |
| SU | 735249 A1 | 5/1980 |
| SU | 1009439 A | 4/1983 |
| SU | 1333319 A2 | 8/1987 |
| SU | 1377053 A1 | 2/1988 |
| SU | 1509051 A1 | 9/1989 |
| SU | 1561964 A1 | 5/1990 |
| SU | 1708312 A1 | 1/1992 |
| SU | 1722476 A1 | 3/1992 |
| SU | 1752361 A1 | 8/1992 |
| WO | WO-9315648 A1 | 8/1993 |
| WO | WO-9420030 A1 | 9/1994 |
| WO | WO-9517855 A1 | 7/1995 |
| WO | WO-9520360 A1 | 8/1995 |
| WO | WO-9623448 A1 | 8/1996 |
| WO | WO-9635464 A1 | 11/1996 |
| WO | WO-9639086 A1 | 12/1996 |
| WO | WO-9639088 A1 | 12/1996 |
| WO | WO-9724073 A1 | 7/1997 |
| WO | WO-9734533 A1 | 9/1997 |
| WO | WO-9903407 A1 | 1/1999 |
| WO | WO-9903409 A1 | 1/1999 |
| WO | WO-9948430 A1 | 9/1999 |
| WO | WO-0024322 A1 | 5/2000 |
| WO | WO-0024330 A1 | 5/2000 |
| WO | WO-0053112 A2 | 9/2000 |
| WO | WO-0057796 A1 | 10/2000 |
| WO | WO-0105702 A1 | 1/2001 |
| WO | WO-0154594 A1 | 8/2001 |
| WO | WO-0158371 A1 | 8/2001 |
| WO | WO-0162164 A2 | 8/2001 |
| WO | WO-0162169 A2 | 8/2001 |
| WO | WO-0191646 A1 | 12/2001 |
| WO | WO-0219932 A1 | 3/2002 |
| WO | WO-0226143 A1 | 4/2002 |
| WO | WO-0236028 A1 | 5/2002 |
| WO | WO-02065933 A2 | 8/2002 |
| WO | WO-03055402 A1 | 7/2003 |
| WO | WO-03094747 A1 | 11/2003 |
| WO | WO-03079909 A3 | 3/2004 |
| WO | WO-2004019803 A1 | 3/2004 |
| WO | WO-2004032783 A1 | 4/2004 |
| WO | WO-2004047626 A1 | 6/2004 |
| WO | WO-2004047653 A2 | 6/2004 |
| WO | WO-2004056277 A1 | 7/2004 |
| WO | WO-2004078050 A2 | 9/2004 |
| WO | WO-2004078051 A2 | 9/2004 |
| WO | WO-2004096015 A2 | 11/2004 |
| WO | WO-2006044581 A2 | 4/2006 |
| WO | WO-2006051252 A1 | 5/2006 |
| WO | WO-2006059067 A1 | 6/2006 |
| WO | WO-2006085389 A1 | 8/2006 |
| WO | WO-2007137304 A2 | 11/2007 |
| WO | WO-2007142625 A2 | 12/2007 |
| WO | WO-2008021969 A2 | 2/2008 |
| WO | WO-2008089404 A2 | 7/2008 |
| WO | WO-2009067649 A2 | 5/2009 |
| WO | WO-2009091497 A2 | 7/2009 |
| WO | WO-2011008672 A2 | 1/2011 |
| WO | WO-2011044343 A2 | 4/2011 |
| WO | WO-2012006306 A2 | 1/2012 |
| WO | WO-2012044606 A2 | 4/2012 |

OTHER PUBLICATIONS

C.C. Thompson et al., "Peroral Endoscopic Reduction of Dilated Gastrojejunal Anastomosis After Roux-en-Y Gastric Bypass: A Possible New Option for Patients with Weight Regain," Surg Endosc (2006) vol. 20., pp. 1744-1748.

Covidien Brochure, "Endo GIA™ Curved Tip Reload with Tri-Staple™ Technology," (2012), 2 pages.

Covidien Brochure, "Endo GIA™ Reloads with Tri-Staple™ Technology," (2010), 2 pages.

Miyata et al., "Biomolecule-Sensitive Hydrogels," Advanced Drug Delivery Reviews, 54 (2002) pp. 79-98.

Jeong et al., "Thermosensitive Sol-Gel Reversible Hydrogels," Advanced Drug Delivery Reviews, 54 (2002) pp. 37-51.

Byrne et al., "Molecular Imprinting Within Hydrogels," Advanced Drug Delivery Reviews, 54 (2002) pp. 149-161.

Covidien Brochure, "Endo GIA™ Ultra Universal Stapler," (2010), 2 pages.

Qiu et al., "Environment-Sensitive Hydrogels for Drug Delivery," Advanced Drug Delivery Reviews, 53 (2001) pp. 321-339.

Hoffman, "Hydrogels for Biomedical Applications," Advanced Drug Delivery Reviews, 43 (2002) pp. 3-12.

(56) References Cited

OTHER PUBLICATIONS

Peppas, "Physiologically Responsive Hydrogels," Journal of Bioactive and Compatible Polymers, vol. 6 (Jul. 1991) pp. 241-246.
Peppas, Editor "Hydrogels in Medicine and Pharmacy," vol. I, Fundamentals, CRC Press, 1986.
Ebara, "Carbohydrate-Derived Hydrogels and Microgels," Engineered Carbohydrate-Based Materials for Biomedical Applications: Polymers, Surfaes, Dendrimers, Nanoparticles, and Hydrogels, Edited by Ravin Narain, 2011, pp. 337-345.
D. Tuite, Ed., "Get the Lowdown on Ultracapacitors," Nov. 15, 2007; [online] URL: http://electronicdesign.com/Articles/Print.cfm?ArticleID=17465, accessed Jan. 15, 2008 (5 pages).
Datasheet for Panasonic TK Relays Ultra Low Profile 2 A Polarized Relay, Copyright Matsushita Electric Works, Ltd. (Known of at least as early as Aug. 17, 2010), 5 pages.
B.R. Coolman, DVM, MS et al., "Comparison of Skin Staples With Sutures for Anastomosis of the Small Intestine in Dogs," Abstract; http://www.blackwell-synergy.com/doi/abs/10.1053/jvet.2000.7539?cookieSet=1&journalCode=vsu which redirects to http://www3.interscience.wiley.com/journal/119040681/abstract?CRETRY=1&SRETRY=0; [online] accessed: Sep. 22, 2008 (2 pages).
Disclosed Anonymously, "Motor-Driven Surgical Stapler Improvements," Research Disclosure Database No. 526041, Published: Feb. 2008.
Biomedical Coatings, Fort Wayne Metals, Research Products Corporation, obtained online at www.fwmetals.com on Jun. 21, 2010 (1 page).
Van Meer et al., "A Disposable Plastic Compact Wrist for Smart Minimally Invasive Surgical Tools," LAAS/CNRS (Aug. 2005).
Breedveld et al., "A New, Easily Miniaturized Sterrable Endoscope," IEEE Engineering in Medicine and Biology Magazine (Nov./Dec. 2005).
ASTM procedure D2240-00, "Standard Test Method for Rubber Property-Durometer Hardness," (Published Aug. 2000).
ASTM procedure D2240-05, "Standard Test Method for Rubber Property-Durometer Hardness," (Published Apr. 2010).
Covidien Brochure, "Endo GIA™ Reloads with Tri-Staple™ Technology," (2010), 1 page.
Covidien Brochure, "Endo GIA™ Black Reload with Tri-Staple™ Technology," (2012), 2 pages.
The Sodem Aseptic Battery Transfer Kit, Sodem Systems, 2000, 3 pages.
Covidien Brochure, "Endo GIA™ Reloads with Tri-Staple™ Technology and Endo GIA™ Ultra Universal Staplers," (2010), 2 pages.
Matsuda, "Thermodynamics of Formation of Porous Polymeric Membrane from Solutions," Polymer Journal, vol. 23, No. 5, pp. 435-444 (1991).
Young, "Microcellular foams via phase separation," Journal of Vacuum Science & Technology A 4(3), (May/Jun. 1986).
Chen et al., "Elastomeric Biomaterials for Tissue Engineering," Progress in Polymer Science 38 (2013), pp. 584-671.
Pitt et al., "Attachment of Hyaluronan to Metallic Surfaces," J. Biomed. Mater. Res. 68A: pp. 95-106, 2004.
Schellhammer et al., "Poly-Lactic-Acid for Coating of Endovascular Stents: Preliminary Results in Canine Experimental Av-Fistulae," Mat.-wiss. u. Werkstofftech., 32, pp. 193-199 (2001).
Solorio et al., "Gelatin Microspheres Crosslinked with Genipin for Local Delivery of Growth Factors," J. Tissue Eng. Regen. Med. (2010), 4(7): pp. 514-523.
http://ninpgan.net/publications/51-100/89.pdf; 2004, Ning Pan, on Uniqueness of Fibrous Materials, Design & Nature II. Eds: Colins, M. and Brebbia, C. Wit Press, Boston, 493-504.
Covidien iDrive™ Ultra in Service Reference Card, "iDrive™ Ultra Powered Stapling Device," (4 pages).
Covidien iDrive™ Ultra Powered Stapling System ibrochure, "The Power of iDrive™ Ultra Powered Stapling System and Tri-Staple™ Technology," (23 pages).
Seils et al., Covidien Summary: Clinical Study "UCONN Biodynamics: Final Report on Results," (2 pages).
Covidien "iDrive™ Ultra Powered Stapling System, A Guide for Surgeons," (6 pages).
Covidien "iDrive™ Ultra Powered Stapling System, Cleaning and Sterilization Guide," (2 pages).
Covidien Brochure "iDrive™ Ultra Powered Stapling System," (6 pages).

\* cited by examiner

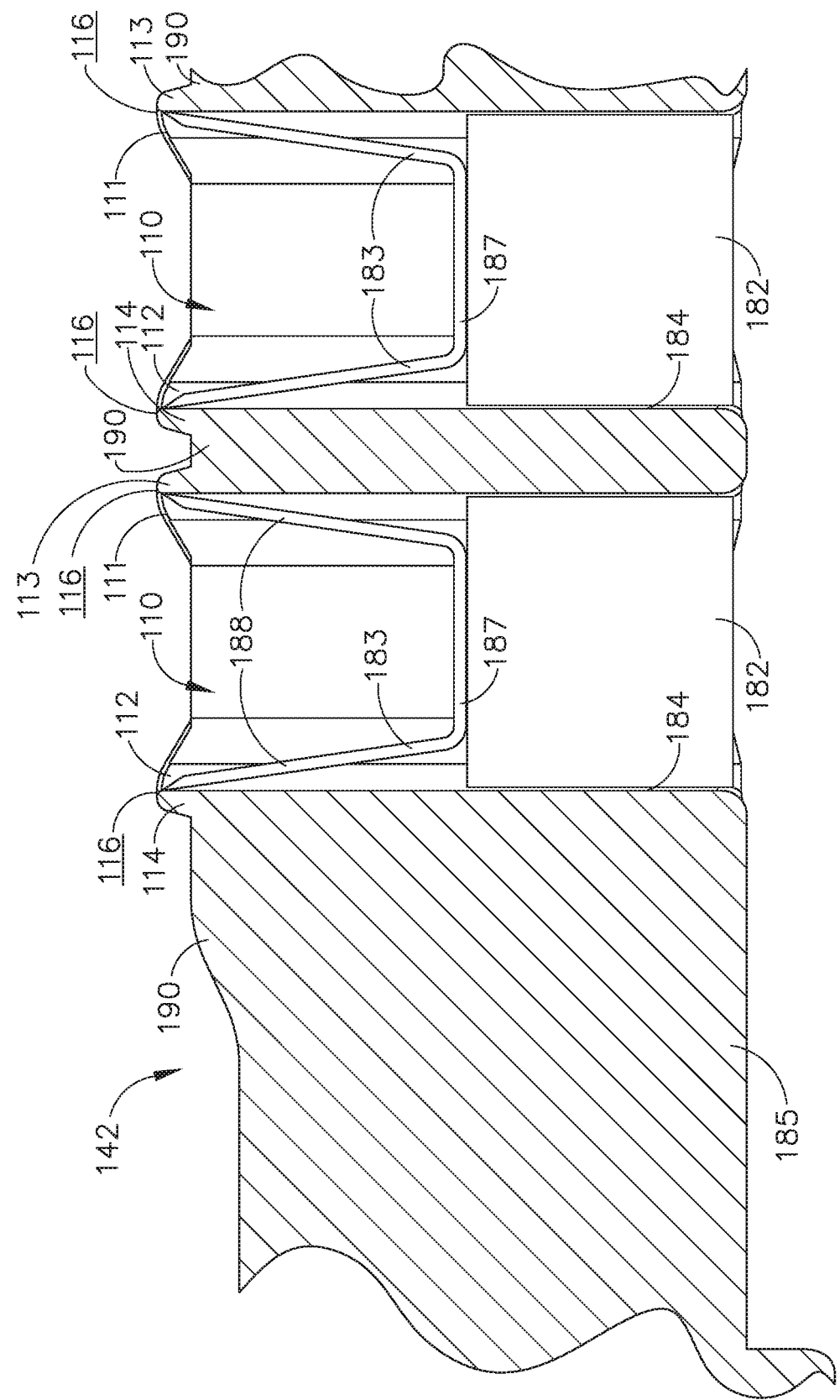

FASTENER CARTRIDGE

CROSS-REFERENCE TO RELATED APPLICATIONS

This application is a continuation application claiming priority under 35 U.S.C. § 120 to U.S. patent application Ser. No. 14/733,026, entitled STAPLE CARTRIDGE, filed Jun. 8, 2015, which issued on Nov. 20, 2018 as U.S. Pat. No. 10,130,363, which is a continuation application claiming priority under 35 U.S.C. § 120 to U.S. patent application Ser. No. 13/772,903, entitled STAPLE CARTRIDGE, filed Feb. 21, 2013, which issued on Sep. 15, 2015 as U.S. Pat. No. 9,131,940, which is a continuation application claiming priority under 35 U.S.C. § 120 to U.S. patent application Ser. No. 12/893,461, entitled STAPLE CARTRIDGE, filed Sep. 29, 2010, which issued on May 27, 2014 as U.S. Pat. No. 8,733,613, the entire disclosures of which are hereby incorporated by reference herein.

BACKGROUND i. Technical Field

The present invention relates to stapling instruments and, in various embodiments, to a surgical stapling instrument for producing one or more rows of staples.

ii. Background of the Related Art

A stapling instrument can include a pair of cooperating elongate jaw members, wherein each jaw member can be adapted to be inserted into a patient and positioned relative to tissue that is to be stapled and/or incised. In various embodiments, one of the jaw members can support a staple cartridge with at least two laterally spaced rows of staples contained therein, and the other jaw member can support an anvil with staple-forming pockets aligned with the rows of staples in the staple cartridge. Generally, the stapling instrument can further include a pusher bar and a knife blade which are slidable relative to the jaw members to sequentially eject the staples from the staple cartridge via camming surfaces on the pusher bar and/or camming surfaces on a wedge sled that is pushed by the pusher bar. In at least one embodiment, the camming surfaces can be configured to activate a plurality of staple drivers carried by the cartridge and associated with the staples in order to push the staples against the anvil and form laterally spaced rows of deformed staples in the tissue gripped between the jaw members. In at least one embodiment, the knife blade can trail the camming surfaces and cut the tissue along a line between the staple rows. Examples of such stapling instruments are disclosed in U.S. Pat. No. 7,794,475, entitled SURGICAL STAPLES HAVING COMPRESSIBLE OR CRUSHABLE MEMBERS FOR SECURING TISSUE THEREIN AND STAPLING INSTRUMENTS FOR DEPLOYING THE SAME, the entire disclosure of which is hereby incorporated by reference herein.

The foregoing discussion is intended only to illustrate various aspects of the related art in the field of the invention at the time, and should not be taken as a disavowal of claim scope.

SUMMARY

In at least one form, a staple cartridge can comprise a plurality of staples and a cartridge body. The cartridge body can comprise a tissue-contacting deck, a plurality of staple cavities, wherein each staple cavity comprises an opening in the deck, and wherein a staple is positioned in each staple cavity. The cartridge body can further comprise a plurality of ridges extending from the tissue-contacting deck, wherein each opening is at least partially surrounded by a ridge.

In at least one form, a staple cartridge can comprise a plurality of staples and a cartridge body. The cartridge body can comprise a middle portion, a side portion, a tissue-contacting deck, a plurality of staple cavities, wherein a staple is positioned in each staple cavity, and a plurality of ridges extending from the tissue-contacting deck, wherein each ridge extends between the middle portion and the side portion of the cartridge body.

In at least one form, a staple cartridge can comprise a plurality of staples and a cartridge body. The cartridge body can comprise a proximal end, a distal end, a tissue-contacting deck, a plurality of staple cavities, wherein a staple is positioned in each staple cavity, and a plurality of ridges extending from the tissue-contacting deck, wherein each ridge comprises a height which varies between a proximal height and a distal height, and wherein the proximal height is closer to the proximal end than the distal height.

In various embodiments, a fastener cartridge comprising a cartridge body and unfired fasteners is disclosed. The cartridge body comprises a deck and fastener cavities. The deck comprises a variable height tissue compression surface. A longitudinal slot is defined through at least a portion of the variable height tissue compression surface. The fastener cavities comprise a first fastener cavity defined in the variable height tissue compression surface on a first side of the longitudinal slot and a second fastener cavity defined in the variable height tissue compression surface on the first side of the longitudinal slot. The first fastener cavity is laterally offset from the second fastener cavity. The unfired fasteners comprise a first unfired fastener and a second unfired fastener. The first unfired fastener is removably positioned in the first fastener cavity. The first unfired fastener comprises a first height. The second unfired fastener is removably positioned in the second fastener cavity. The second unfired fastener comprises a second height. The first height and the second height are different. The variable height tissue compression surface is configured to provide targeted tissue compression between the first unfired fastener and the second unfired fastener.

In various embodiments, a fastener cartridge comprising a cartridge body and unfired fasteners is disclosed. The cartridge body comprises a deck and fastener cavities. The deck comprises a variable height tissue compression surface. A longitudinal slot is defined through at least a portion of the variable height tissue compression surface. The fastener cavities comprise a first fastener cavity defined in the variable height tissue compression surface on a first side of the longitudinal slot and a second fastener cavity defined in the variable height tissue compression surface on the first side of the longitudinal slot. The unfired fasteners comprise a first unfired fastener and a second unfired fastener. The first unfired fastener is removably positioned in the first fastener cavity. The first unfired fastener comprises a first height. The second unfired fastener is removably positioned in the second fastener cavity. The second unfired fastener comprises a second height. The first height and the second height are different. The variable height tissue compression surface is configured to provide targeted tissue compression between the first unfired fastener and the second unfired fastener. The variable height tissue compression surface comprises a peak between the first unfired fastener and the second unfired fastener.

In various embodiments, a fastener cartridge comprising a cartridge body, unfired fasteners, and a sled is disclosed. The cartridge body comprises a deck and fastener cavities. The deck comprises a variable height tissue compression surface. A longitudinal slot is defined through at least a portion of the variable height tissue compression surface. The fastener cavities comprise a first fastener cavity defined in the variable height tissue compression surface on a first side of the longitudinal slot and a second fastener cavity defined in the variable height tissue compression surface on the first side of the longitudinal slot. The unfired fasteners comprises a first unfired fastener and a second unfired fastener. The first unfired fastener is removably positioned in the first fastener cavity. The first unfired fastener comprises a first height. The second unfired fastener is removably positioned in the second fastener cavity. The second unfired fastener comprises a second height. The first height and the second height are different. The sled is configured to fire the unfired fasteners from the fastener cavities during a firing stroke. The variable height tissue compression surface is configured to provide targeted tissue compression between the first unfired fastener and the second unfired fastener.

In various embodiments, a fastener cartridge comprising a cartridge body and unfired fasteners is disclosed. The cartridge body comprises a deck and fastener cavities. The deck comprises a variable height tissue compression surface. A longitudinal slot is defined through at least a portion of the variable height tissue compression surface. The fastener cavities comprise a first fastener cavity defined in the variable height tissue compression surface on a first side of the longitudinal slot and a second fastener cavity defined in the variable height tissue compression surface on the first side of the longitudinal slot. The unfired fasteners comprise a first unfired fastener and a second unfired fastener. The first unfired fastener is removably positioned in the first fastener cavity. The first unfired fastener comprises a first height. The second unfired fastener is removably positioned in the second fastener cavity. The second unfired fastener comprises a second height. The first height and the second height are different. The unfired fasteners comprise B-form staples. The variable height tissue compression surface is configured to provide targeted tissue compression between the first unfired fastener and the second unfired fastener.

In various embodiments, a fastener cartridge comprising a cartridge body and unfired fasteners is disclosed. The cartridge body comprises a deck and fastener cavities. The deck comprises an uneven tissue compression surface. A longitudinal slot is defined through at least a portion of the uneven tissue compression surface. The fastener cavities comprises a first fastener cavity defined in the uneven tissue compression surface on a first side of the longitudinal slot and a second fastener cavity defined in the uneven tissue compression surface on the first side of the longitudinal slot. The unfired fasteners comprises a first unfired fastener and a second unfired fastener. The first unfired fastener is removably positioned in the first fastener cavity and comprises a first height. The second unfired fastener is removably positioned in the second fastener cavity and comprises a second height. The first height and the second height are different. The uneven tissue compression surface comprises at least one peak between the first fastener cavity and the second fastener cavity. The uneven tissue compression surface is configured to provide variable compression longitudinally along a portion of the deck.

In various embodiments, a fastener cartridge comprising a cartridge body and unfired fasteners is disclosed. The cartridge body comprises a deck and fastener cavities. The deck comprises an uneven tissue compression surface. A longitudinal slot is defined through at least a portion of the uneven tissue compression surface. The fastener cavities comprise a first fastener cavity defined in the uneven tissue compression surface on a first side of the longitudinal slot and a second fastener cavity defined in the uneven tissue compression surface on the first side of the longitudinal slot. The unfired fasteners comprise a first unfired fastener and a second unfired fastener. The first unfired fastener is removably positioned in the first fastener cavity and comprises a first height. The second unfired fastener is removably positioned in the second fastener cavity and comprises a second height. The first height and the second height are different. The uneven tissue compression surface comprises at least one peak between the first fastener cavity and the second fastener cavity. The uneven tissue compression surface is configured to provide variable compression laterally along a portion of the deck.

In various embodiments, a fastener cartridge comprising a cartridge body and unfired fasteners is disclosed. The cartridge body comprises a deck and fastener cavities. The deck comprises an uneven tissue compression surface. A longitudinal slot is defined through at least a portion of the uneven tissue compression surface. The fastener cavities comprise a first fastener cavity defined in the uneven tissue compression surface on a first side of the longitudinal slot and a second fastener cavity defined in the uneven tissue compression surface on the first side of the longitudinal slot. The first fastener cavity is laterally offset from the second fastener cavity. The unfired fasteners comprise a first unfired fastener and a second unfired fastener. The first unfired fastener is removably positioned in the first fastener cavity and comprises a first height. The second unfired fastener is removably positioned in the second fastener cavity and comprises a second height. The first height and the second height are different. The uneven tissue compression surface comprises at least one peak between the first fastener cavity and the second fastener cavity.

In various embodiments, a fastener cartridge comprising a cartridge body and unfired fasteners is disclosed. The cartridge body comprises a deck and fastener cavities. The deck comprises an uneven tissue compression surface. A longitudinal slot is defined through at least a portion of the uneven tissue compression surface. The fastener cavities comprise a first fastener cavity defined in the uneven tissue compression surface on a first side of the longitudinal slot and a second fastener cavity defined in the uneven tissue compression surface on the first side of the longitudinal slot. The first fastener cavity is laterally offset from the second fastener cavity. The unfired fasteners comprise a first unfired fastener and a second unfired fastener. The first unfired fastener is removably positioned in the first fastener cavity and comprises a first height. The second unfired fastener is removably positioned in the second fastener cavity and comprises a second height. The first height and the second height are different. The uneven tissue compression surface comprises a plurality of peaks between the first fastener cavity and the second fastener cavity.

In various embodiments, a fastener cartridge comprising a cartridge body, unfired fasteners, and a sled is disclosed. The cartridge body comprises a deck and fastener cavities. The deck comprises an uneven tissue compression surface. A longitudinal slot is defined through at least a portion of the uneven tissue compression surface. The fastener cavities comprise a first fastener cavity defined in the uneven tissue compression surface on a first side of the longitudinal slot and a second fastener cavity defined in the uneven tissue compression surface on the first side of the longitudinal slot. The first fastener cavity is laterally offset from the second fastener cavity. The unfired fasteners comprise a first unfired fastener and a second unfired fastener. The first unfired fastener is removably positioned in the first fastener cavity and comprises a first height. The second unfired fastener is removably positioned in the second fastener cavity and comprises a second height. The first height and the second height are different. The sled is configured to fire the unfired fasteners from the fastener cavities during a firing stroke. The uneven tissue compression surface comprises at least one peak between the first fastener cavity and the second fastener cavity.

In various embodiments, a fastener cartridge comprising a cartridge body and unfired fasteners removably positioned in the cartridge body is disclosed. The cartridge body comprises an uneven tissue compression surface. A longitudinal slot is defined through at least a portion of the uneven tissue compression surface. The unfired fasteners comprise a first unfired fastener on a first side of the longitudinal slot and a second unfired fastener on the first side of the longitudinal slot. The first unfired fastener comprises a first height. The second unfired fastener comprises a second height. The first height and the second height are different. The uneven tissue compression surface comprises a plurality of peaks on the first side of the longitudinal slot. The uneven tissue compression surface is configured to provide variable pre-compression laterally along a width of the cartridge body.

In various embodiments, a fastener cartridge comprising a cartridge body and unfired fasteners is disclosed. The cartridge body comprises an uneven tissue compression surface. A longitudinal slot is defined through at least a portion of the uneven tissue compression surface. The unfired fasteners are removably positioned in the cartridge body. The unfired fasteners comprise a first unfired fastener on a first side of the longitudinal slot and a second unfired fastener on the first side of the longitudinal slot. The first unfired fastener comprises a first height. The unfired fastener is laterally offset from the second unfired fastener. The second unfired fastener comprises a second height. The first height and the second height are different. The uneven tissue compression surface comprises a plurality of peaks on the first side of the longitudinal slot.

In various embodiments, a fastener cartridge comprising a cartridge body and unfired fasteners removably positioned in the cartridge body is disclosed. The cartridge body comprises an uneven tissue compression surface. A longitudinal slot is defined through at least a portion of the uneven tissue compression surface. The unfired fasteners comprise a first unfired fastener on a first side of the longitudinal slot and a second unfired fastener on the first side of the longitudinal slot. The first unfired fastener comprises a first height. The second unfired fastener comprises a second height. The first height and the second height are different. The uneven tissue compression surface comprises a plurality of peaks on the first side of the longitudinal slot. The peaks comprise the same peak height.

In various embodiments, a fastener cartridge comprising a cartridge body, unfired fasteners, and a sled configured to fire the unfired fasteners from the cartridge body during a firing stroke is disclosed. The cartridge body comprises an uneven tissue compression surface. A longitudinal slot is defined through at least a portion of the uneven tissue compression surface. The unfired fasteners are removably positioned in the cartridge body. The unfired fasteners comprise a first unfired fastener on a first side of the longitudinal slot and a second unfired fastener on the first side of the longitudinal slot. The first unfired fastener comprises a first height. The second unfired fastener comprises a second height. The first height and the second height are different. The uneven tissue compression surface comprises a plurality of peaks on the first side of the longitudinal slot.

The foregoing discussion should not be taken as a disavowal of claim scope.

BRIEF DESCRIPTION OF THE DRAWINGS

Various features of the embodiments described herein are set forth with particularity in the appended claims. The various embodiments, however, both as to organization and methods of operation, together with advantages thereof, may be understood in accordance with the following description taken in conjunction with the accompanying drawings as follows.

FIG. 9 is a detail view illustrating staples positioned within staple cavities defined in the staple cartridge of FIG. 7.

Corresponding reference characters indicate corresponding parts throughout the several views. The exemplifications set out herein illustrate various embodiments of the invention, in one form, and such exemplifications are not to be construed as limiting the scope of the invention in any manner.

DETAILED DESCRIPTION

Numerous specific details are set forth to provide a thorough understanding of the overall structure, function, manufacture, and use of the embodiments as described in the specification and illustrated in the accompanying drawings. It will be understood by those skilled in the art, however, that the embodiments may be practiced without such specific details. In other instances, well-known operations, components, and elements have not been described in detail so as not to obscure the embodiments described in the specification. Those of ordinary skill in the art will understand that the embodiments described and illustrated herein are non-limiting examples, and thus it can be appreciated that the specific structural and functional details disclosed herein may be representative and illustrative. Variations and changes thereto may be made without departing from the scope of the claims.

Reference throughout the specification to "various embodiments," "some embodiments," "one embodiment," or "an embodiment", or the like, means that a particular feature, structure, or characteristic described in connection with the embodiment is included in at least one embodiment. Thus, appearances of the phrases "in various embodiments," "in some embodiments," "in one embodiment," or "in an embodiment", or the like, in places throughout the specification are not necessarily all referring to the same embodiment. Furthermore, the particular features, structures, or characteristics may be combined in any suitable manner in one or more embodiments. Thus, the particular features, structures, or characteristics illustrated or described in connection with one embodiment may be combined, in whole or in part, with the features structures, or characteristics of one or more other embodiments without limitation. Furthermore, it will be appreciated that for conciseness and clarity, spatial terms such as "vertical," "horizontal," "up," and "down", for example, may be used herein with respect to the illustrated embodiments. However, these terms are used to assist the reader and are not intended to be limiting and absolute.

Figure 1:
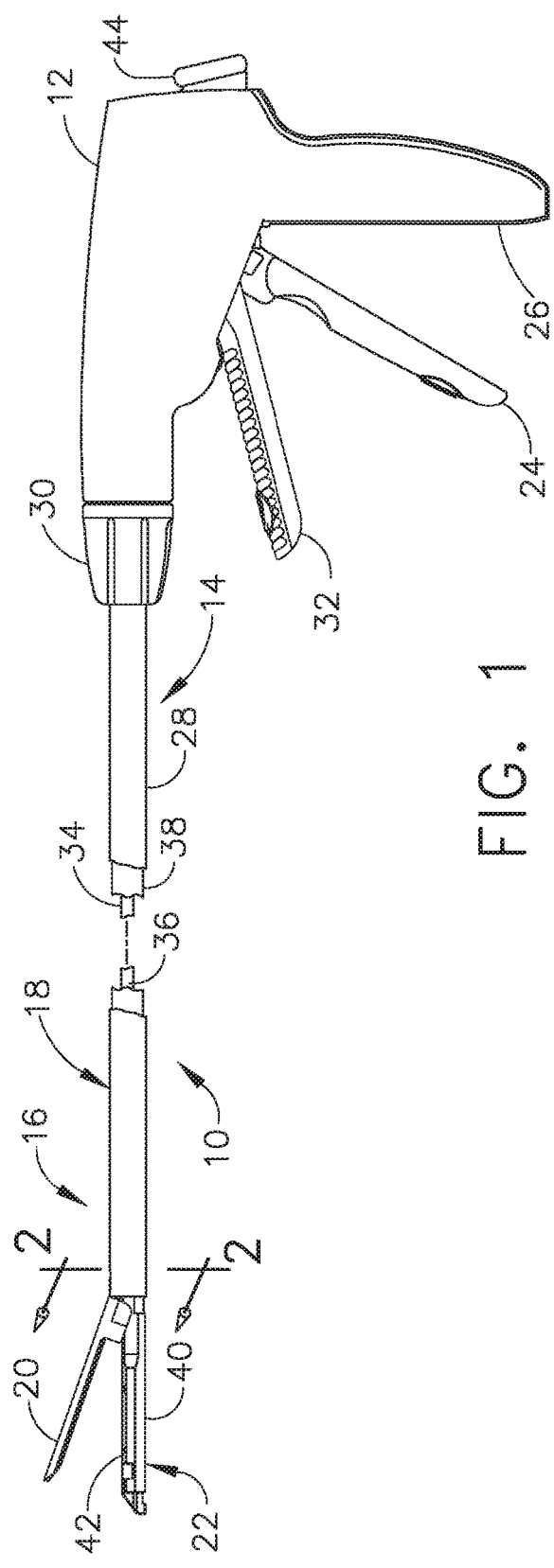
FIG. 1 is an elevational view of a surgical stapling instrument.

Turning to FIG. 1, a surgical stapling and severing instrument 10 can include a handle portion 12 that can be manipulated in order to position an implement portion 14 in a surgical site. In various embodiments, the implement portion 14 can include an end effector 16 attached to an elongate shaft 18. In various circumstances, the implement portion 14 can be sized and configured to be inserted through a cannula of a trocar (not shown) into the surgical site in order to perform an endoscopic or laparoscopic surgical procedure, for example. The end effector 16 can comprise an upper jaw, or anvil, 20 and a lower jaw 22, wherein the anvil 20 can be moved between an open position and a closed position when the closure trigger 24 of the handle portion 12 is moved, or depressed, toward a pistol grip 26 of the handle portion 12. In various embodiments, the depression of the closure trigger 24 can advance an outer closing sleeve 28 of the elongate shaft 18 wherein the outer closing sleeve 28 can contact the anvil 20 and pivot the anvil 20 into its closed position. In certain circumstances, the surgeon may rotate the implement potion 14 about its longitudinal axis by twisting a shaft rotation knob 30. In any event, once the end effector 16 has been inserted into an insufflated body cavity, for example, the closure trigger 24 may be released thereby allowing the anvil 20 to be biased open by a spring (not shown) and positioned relative to the targeted tissue. In various embodiments, the closure trigger 24 can be locked in its depressed condition and, in at least one embodiment, the handle portion 12 can further comprise a lock release actuator 44 which can be depressed to unlock the closure trigger 24. Once the anvil 20 and the lower jaw 22 have been suitably positioned relative to the tissue in the surgical site, the closure trigger 24 can be depressed once again in order to close the anvil 20 and compress the tissue against a staple cartridge 42 attached to the bottom jaw 22.

Figure 2:
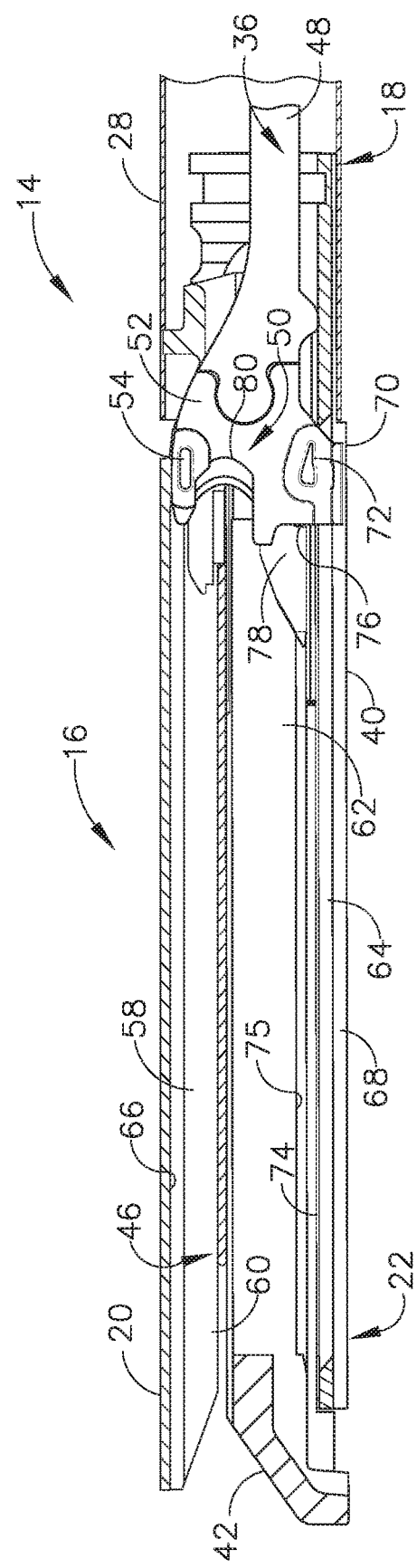
FIG. 2 is a cross-sectional view of an end effector of the surgical stapling instrument of FIG. 1 taken along line 2-2 in FIG. 1.
Figure 3:
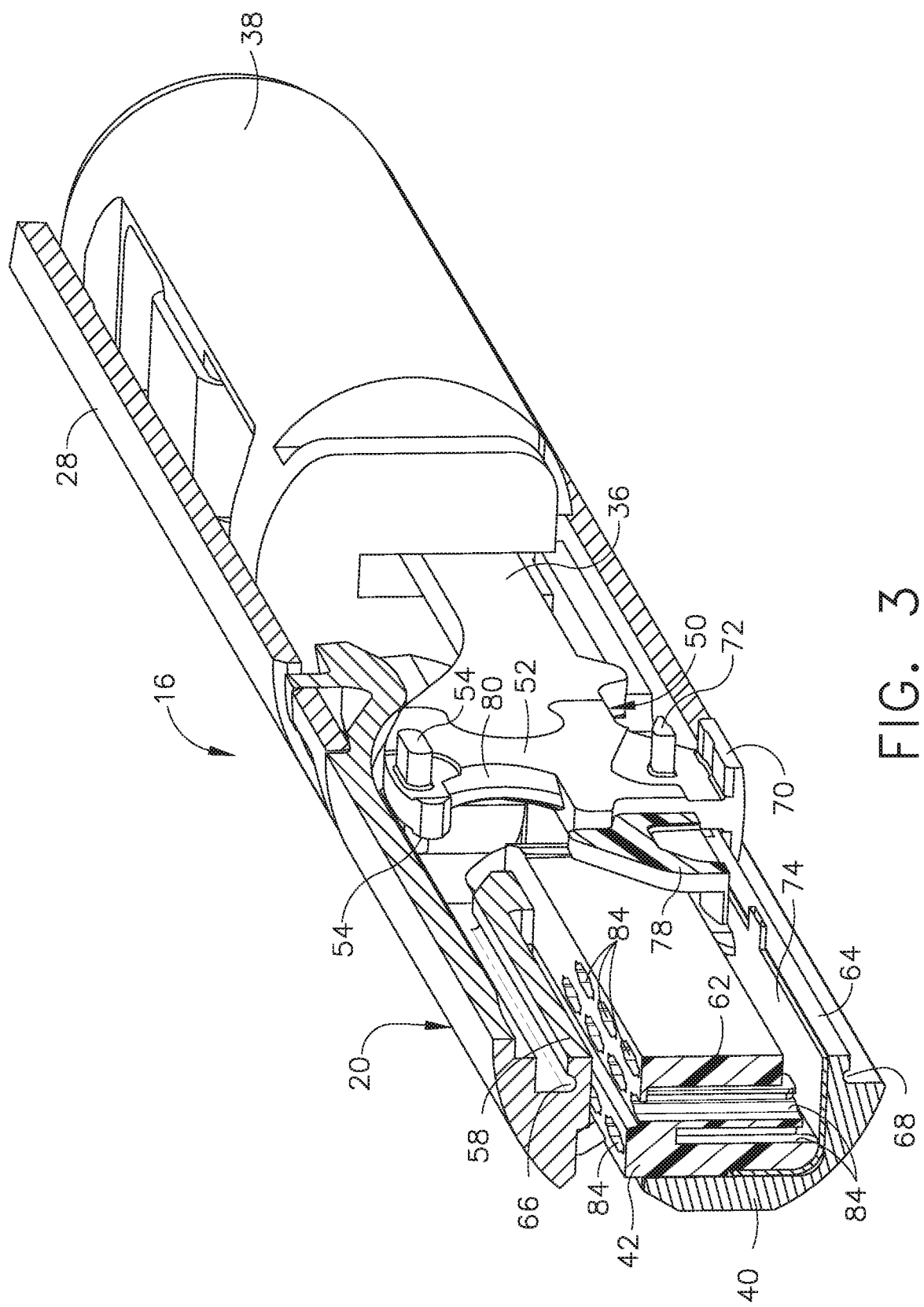
FIG. 3 is a cross-sectional perspective view of the end effector of FIG. 1.

Once the anvil 20 has been closed, a firing trigger 32 can be drawn, or depressed, toward the closure trigger 24 and the pistol grip 26 in order to apply a firing force or motion to a firing member and advance the firing member from an unfired position. In various embodiments, the firing member can comprise a proximal firing rod 34 which is attached to a distal firing bar 36. In at least one such embodiment, the firing rod 34 and/or the firing bar 36 can be supported within a frame 38 in shaft 18 which can extend between the handle portion 12 and the end effector 16. As a result of the firing motion applied to the firing member, the firing bar 36 can be advanced distally within a elongate staple cartridge channel 40 of the lower jaw 22 and a staple cartridge 42 positioned within the cartridge channel 40. In various embodiments, referring to FIG. 2, the firing bar 36 can comprise an attachment portion 48 that is attached to an E-beam 50 which can translate within the end effector 16. The E-beam 50 can comprise a vertical portion 52 which can pass through a narrow longitudinal anvil slot 58 extending through a tissue-contacting surface 60 in the anvil 20, a narrow vertical slot 62 in the staple cartridge 42, and a narrow longitudinal channel slot 64 in the elongate staple channel 40 when the E-beam 50 is advanced distally. Referring now to FIGS. 2 and 3, the anvil slot 58 can extend upwardly into the anvil 20 and can comprise an end which opens into a laterally-widened longitudinal channel 66 sized and configured to receive an upper pin 54 that extends laterally from the vertical portion 52. Similarly, the channel slot 64 can extend downwardly into the channel 40 and can comprise an end which opens into a laterally-widened longitudinal channel 68 sized and configured to receive one or more lower feet 70 extending laterally from the vertical portion 52.

Figure 4:
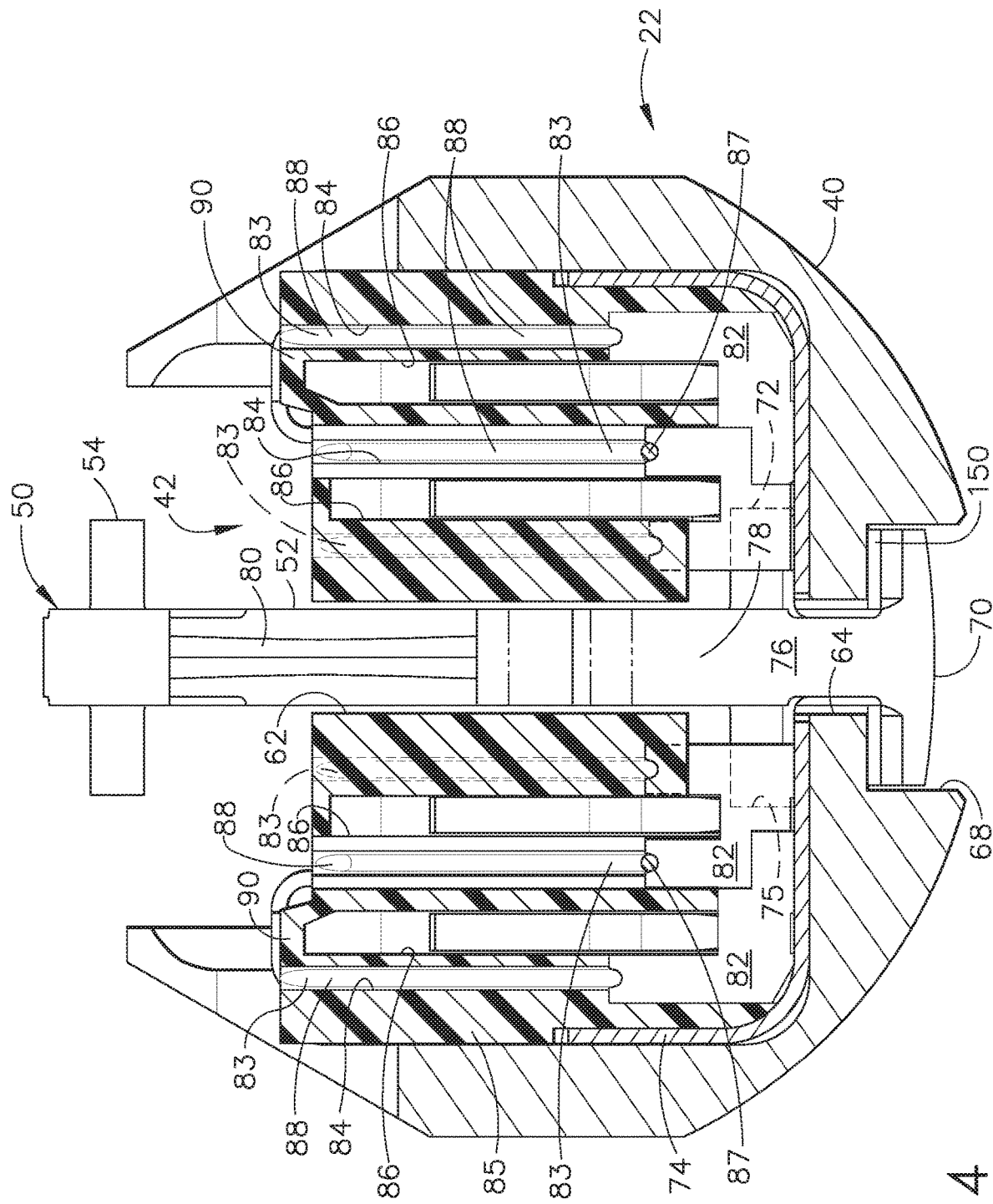
FIG. 4 is a cross-sectional view of the end effector of FIG. 1 illustrating staples contained therein in an unfired configuration.

In various embodiments, further to the above, the E-beam 50 can further comprise one or more middle pins 72 which can extend laterally from the vertical portion 52 and can be configured to slide along a top surface of a bottom tray 74 of the staple cartridge 42. In certain embodiments, the middle pins 72 can be configured to seat the staple cartridge 42, or assure that the staple cartridge 42 remains seated, in the channel 40. A longitudinal firing recess 75 formed in the staple cartridge 42 above the bottom tray 74 is sized to allow the middle pins 72 to translate through the staple cartridge 42. In various embodiments, the E-beam 50 can further comprise a distal drive surface 76 which can be configured to translate through the vertical slot 62 in the staple cartridge 42 and drive a wedge sled 78 distally through the staple cartridge 42. In certain embodiments, the wedge sled 78 can be integrally-formed within the E-beam 50 while, in other embodiments, the wedge sled 78 can reside in the staple cartridge 42 and can be contacted by the drive surface 76 as the E-beam 50 is advanced distally. The vertical portion 52 of the E-beam 50 can further comprise a cutting surface 80 which extends along a distal edge above the distal drive surface 76 and below the upper pin 54 that severs the clamped tissue 46 as the tissue 46 is being stapled. Referring now to FIG. 4, the wedge sled 78 can be configured to engage one or more staple drivers 82 and drive the staple drivers 82 upwardly toward the anvil 20. In various embodiments, staples, such as staples 83, for example, can be seated on and/or otherwise supported by the staple drivers 82 such that, as the staple drivers 82 are lifted upwardly, the staples 83 can be lifted upwardly as well. In at least one such embodiment, the staples 83 can also be at least partially positioned within staple cavities, or pockets, 84 in a staple cartridge body 85 of the staple cartridge 42 wherein, as the staples 83 are lifted upwardly, the staples 83 can contact the anvil 20 and can be ejected from the staple cavities 84. In at least one embodiment, referring again to FIG. 4, the bottom tray 74 can be attached to the cartridge body 85 in order to retain the staple drivers 82 and the staples 83 within the staple cartridge 42 until the staples 83 are deployed therefrom as described above.

Figure 5:
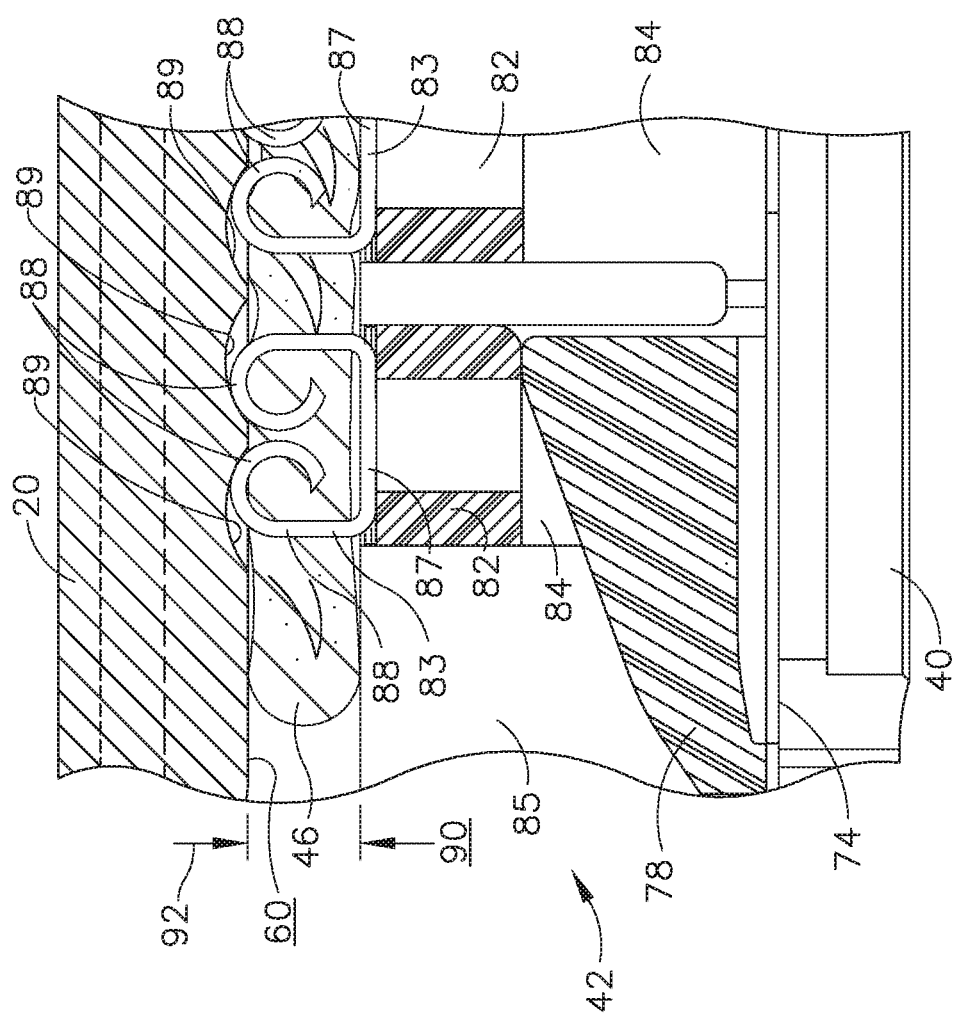
FIG. 5 is a diagram illustrating the staples of FIG. 4 in a fired configuration.
Figure 6:
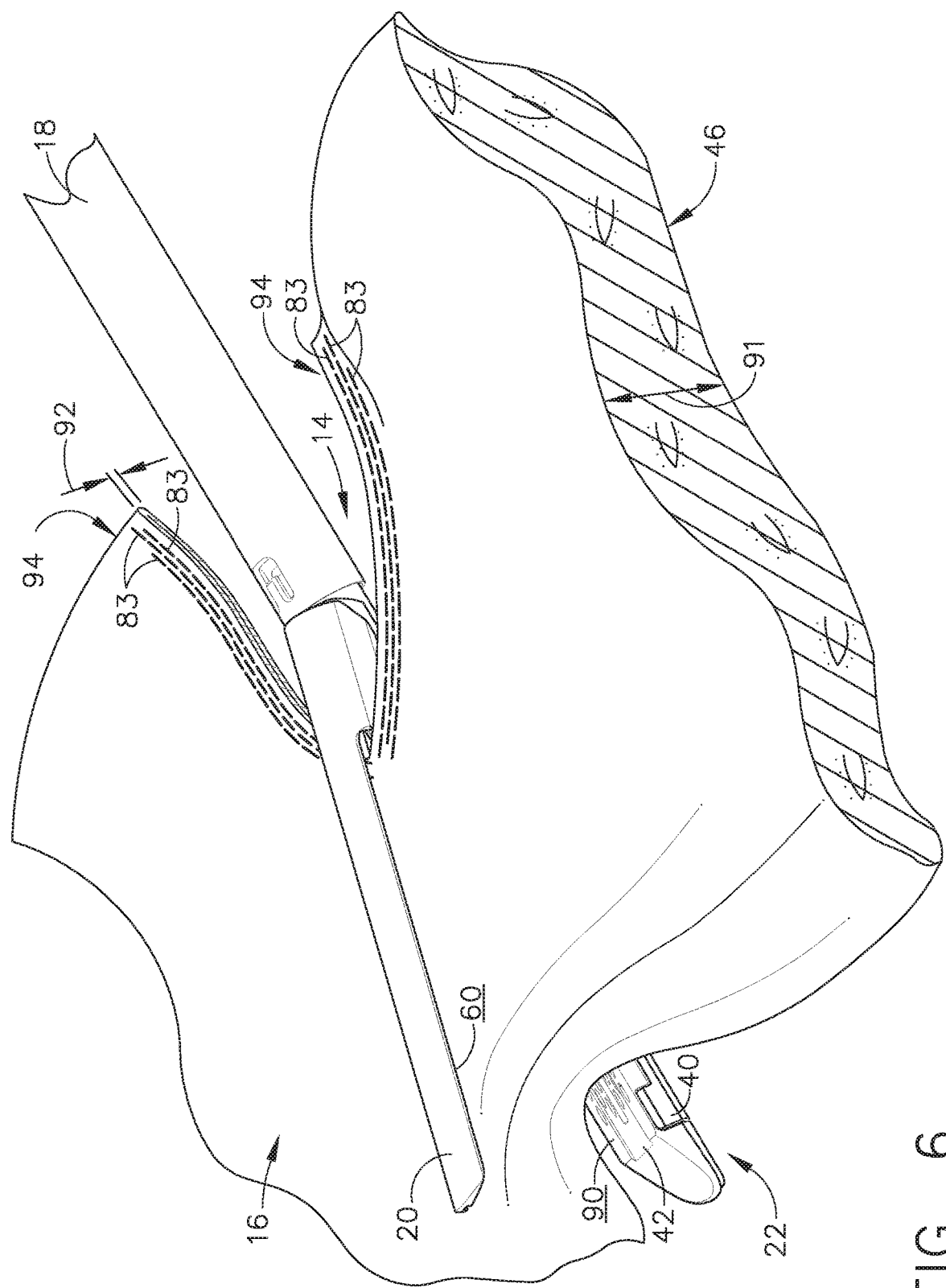
FIG. 6 is a diagram illustrating the end effector of FIG. 1 being used to staple and transect tissue.

In use, referring now to FIGS. 5 and 6, the anvil 20 can be positioned on one side of the tissue 46 and the bottom jaw 22 can be positioned on the opposite side of the tissue 46 such that, when the anvil 20 is closed onto the tissue, the tissue-contacting surface 60 of the anvil 20 and the tissue-contacting deck 90 of the staple cartridge 42 can compress the tissue 46 between an uncompressed thickness 91 and a compressed thickness 92. In order to staple and transect the tissue 46, as described above, the wedge sled 78 can be advanced distally within the staple cartridge 42 in order to lift the staple drivers 82 toward the anvil 20 and deform the staples 83. In various embodiments, each staple driver 82 can comprise one or more slots defined therein which can be configured to receive and releasably hold the bases 87 of the staples 83 in position. In at least one such embodiment, each staple 83 can comprise one or more staple legs 88 extending from the base 87, wherein the staple legs 88 can extend upwardly into the staple cavities 84. In various embodiments, the tips of the staple legs 88 can be recessed with respect to the deck, or tissue-contacting surface, 90 of the cartridge body 85 when the staples 83 are in their unfired position. As the staples 83 are being lifted upwardly by the drivers 82, the tips of the staple legs 88 can emerge from the staple cavities 84, penetrate the tissue 46, and contact the anvil forming pockets 89 positioned opposite the staple cavities 84. The anvil forming pockets 89 can be configured to deform the staples 83 into any suitable shape, such as the B-form shape depicted in FIG. 5, for example. As the staples 83 are deployed, referring now to FIG. 6, the cutting edge 80 can transect the tissue 46 into stapled portions 94.

As described above, the jaw members of an end effector can be configured to apply a compressive pressure, or force, to the tissue being stapled. In various circumstances, however, the tissue can be slippery, for example, and at least a portion of the tissue can slide relative to the jaw members. In certain circumstances, the tissue can slide out of the distal end of the end effector in a longitudinal direction and/or slide out of the sides of the end effector in a direction which is transverse to the longitudinal direction. In some circumstances, portions of the tissue can milk out of the distal end of the end effector and/or the sides of the end effector when the tissue is compressed. In various embodiments disclosed herein, a staple cartridge can comprise one or more tissue retention features which can be configured to prevent, or at least reduce the possibility of, tissue positioned within the end effector from moving relative to the end effector.

Figure 7:
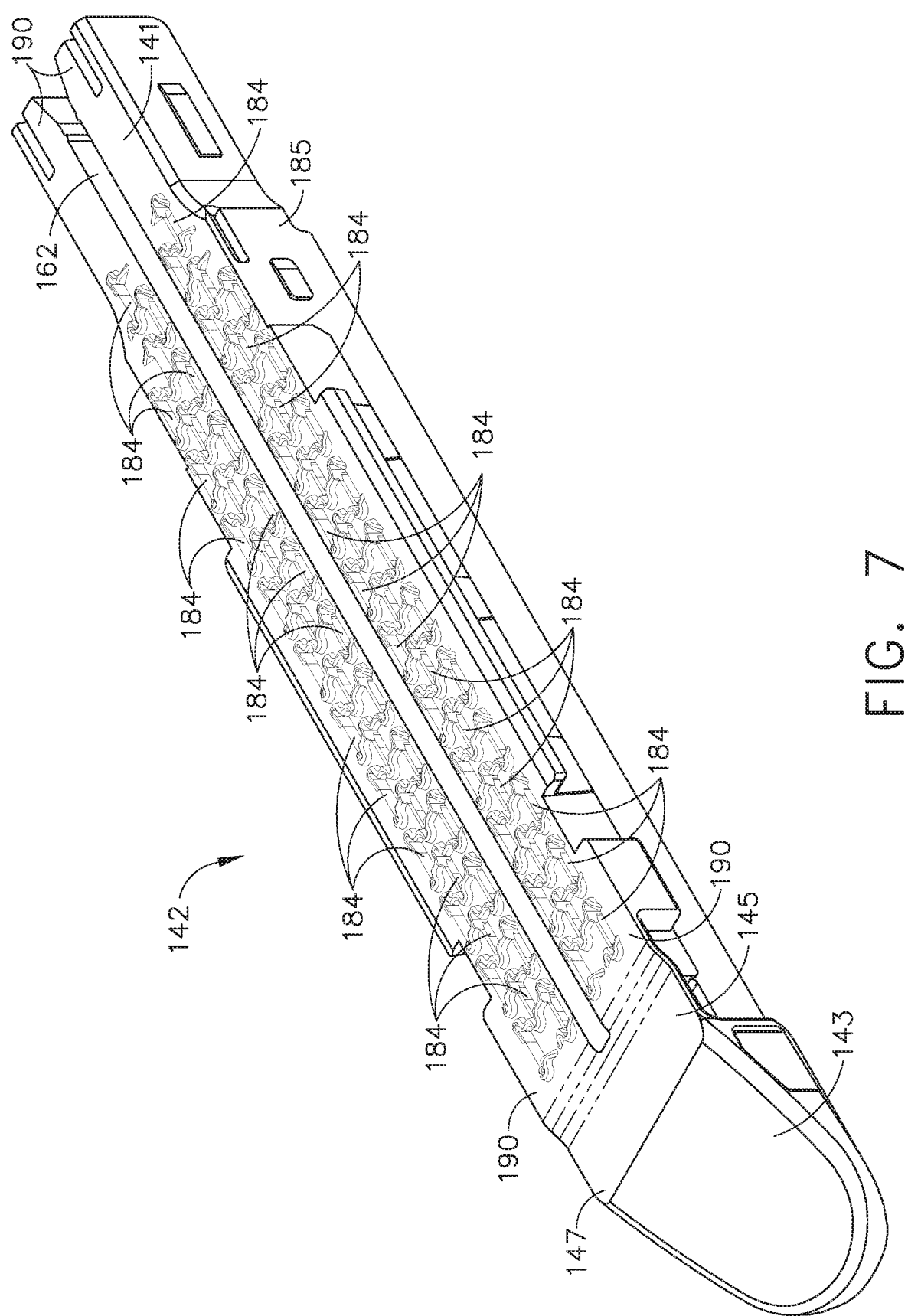
FIG. 7 is a perspective view of a staple cartridge in accordance with at least one embodiment comprising a plurality of ridges extending from a cartridge body.
Figure 8:
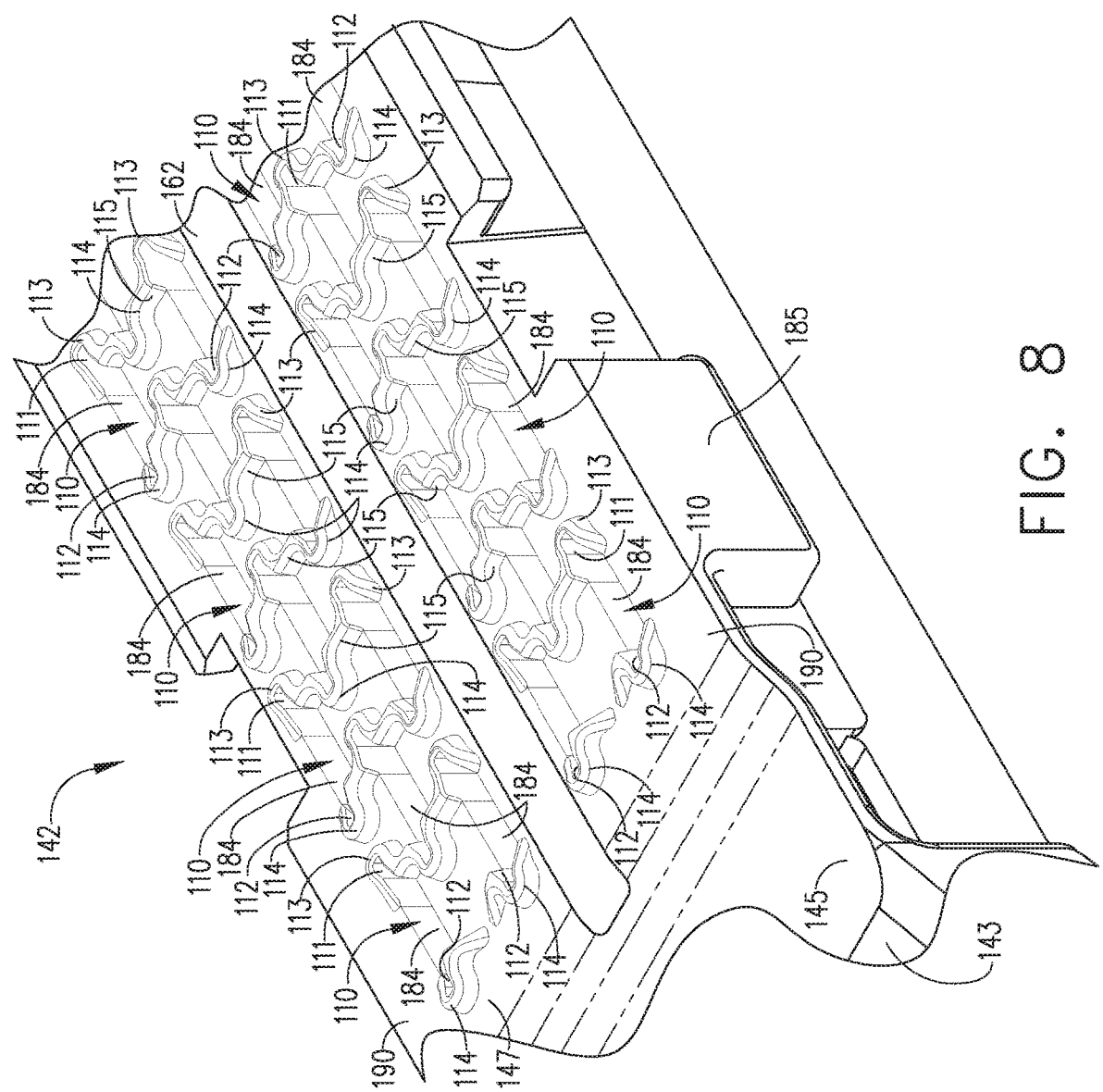
FIG. 8 is a detail view of the staple cartridge of FIG. 7.

In various embodiments, referring now to FIGS. 7 and 8, a staple cartridge, such as staple cartridge 142, for example, can comprise a cartridge body 185 and a plurality of staples, such as staples 187 (FIG. 9), for example, positioned within the cartridge body 185. The cartridge body 185 can comprise a proximal end 141 and a distal end 143, wherein the proximal end 141 can be configured to be inserted into a proximal end of a staple cartridge channel and the distal end 143 can be configured to be inserted into a distal end of the staple cartridge channel. In at least one embodiment, the cartridge body 185 can comprise a plurality of staple cavities 184 which can each be configured to receive a staple 187 therein. In certain alternative embodiments, although not illustrated, a staple cavity can comprise more than one staple positioned therein. In any event, the staple cavities 184 can be arranged in a plurality of rows within the cartridge body 185. More particularly, in at least one embodiment, the staple cavities 184 can be arranged in three staple rows, for example, on a first side 145 of the cartridge body 185 and three staple rows, for example, on a second side 147 of the cartridge body 185. In at least one such embodiment, the first side 145 and the second side 147 of the cartridge body 185 can be separated by a knife slot 162 which can be configured to slidably receive a cutting member therein. In various other embodiments, a cartridge can comprise any other suitable number of staple rows, such as two staple rows or four staple rows, for example, on each side of the knife slot 162. Referring to FIG. 9, in various embodiments, the staple cartridge 142 can further comprise a plurality of staple drivers 182 configured to support the staples 187 and/or eject the staples 187 from the staple cavities 184. In certain embodiments, each staple cavity 184 can comprise an open end, or opening, 110 in the deck 190 of the cartridge body 185 through which the staples 187 can be ejected.

In various embodiments, referring primarily to FIG. 8, the staple cavities 184 can be arranged such that they are staggered longitudinally relative to one another. For example, the staple cavities 184 on the first side 145 of the cartridge body 185, for example, can be arranged in an innermost row of staple cavities 184, an intermediate row of staple cavities 184, and an outermost row of staple cavities 184, wherein the staple cavities 184 in one row may not be aligned transversely with the staple cavities 184 in one or both of the other rows. In at least one embodiment, each staple cavity 184 can comprise a proximal end 111 and a distal end 112, wherein the proximal end 111 of each staple cavity 184 can be positioned closer to the proximal end 141 of the cartridge body 185 than the distal end 112. Likewise, the distal end 112 of each cavity 184 can be positioned closer to the distal end 143 of the cartridge body 185 than the proximal end 111. In various embodiments, the innermost row of staple cavities 184 can be positioned such that the distal ends 112 of the staple cavities 184 within the innermost row are positioned distally with respect to the distal ends 112 of the staple cavities 184 in the intermediate row of staple cavities 184. Similarly, the outermost row of staple cavities 184 can be positioned such that the distal ends 112 of the staple cavities 184 within the outermost row are positioned distally with respect to the distal ends 112 of the staple cavities in the intermediate row of staple cavities 184. For example, the distalmost staple cavity 184 in the innermost row can be positioned distally with respect to the distalmost staple cavity 184 in the intermediate row and, similarly, the distalmost staple cavity 184 in the outermost row can be positioned distally with respect to the distalmost staple cavity 184 in the intermediate row. In certain embodiments, the staple cavities 184 of the innermost row and the staple cavities 184 of the outermost row can be aligned transversely with each other such that, one, the distal ends 112 of the innermost staple cavities 184 are aligned with the distal ends 112 of the outermost staple cavities 184 and, two, the proximal ends 111 of the innermost staple cavities 184 are aligned with the proximal ends 111 of the outermost staple cavities 184. In various embodiments, each staple cavity 184, and their openings 110, can have the same, or at least approximately the same, configuration and, in at least one embodiment, the staple cavities 184 can be spaced equidistantly, or at least substantially equidistantly, relative to one another within a staple row.

Figure 8A:
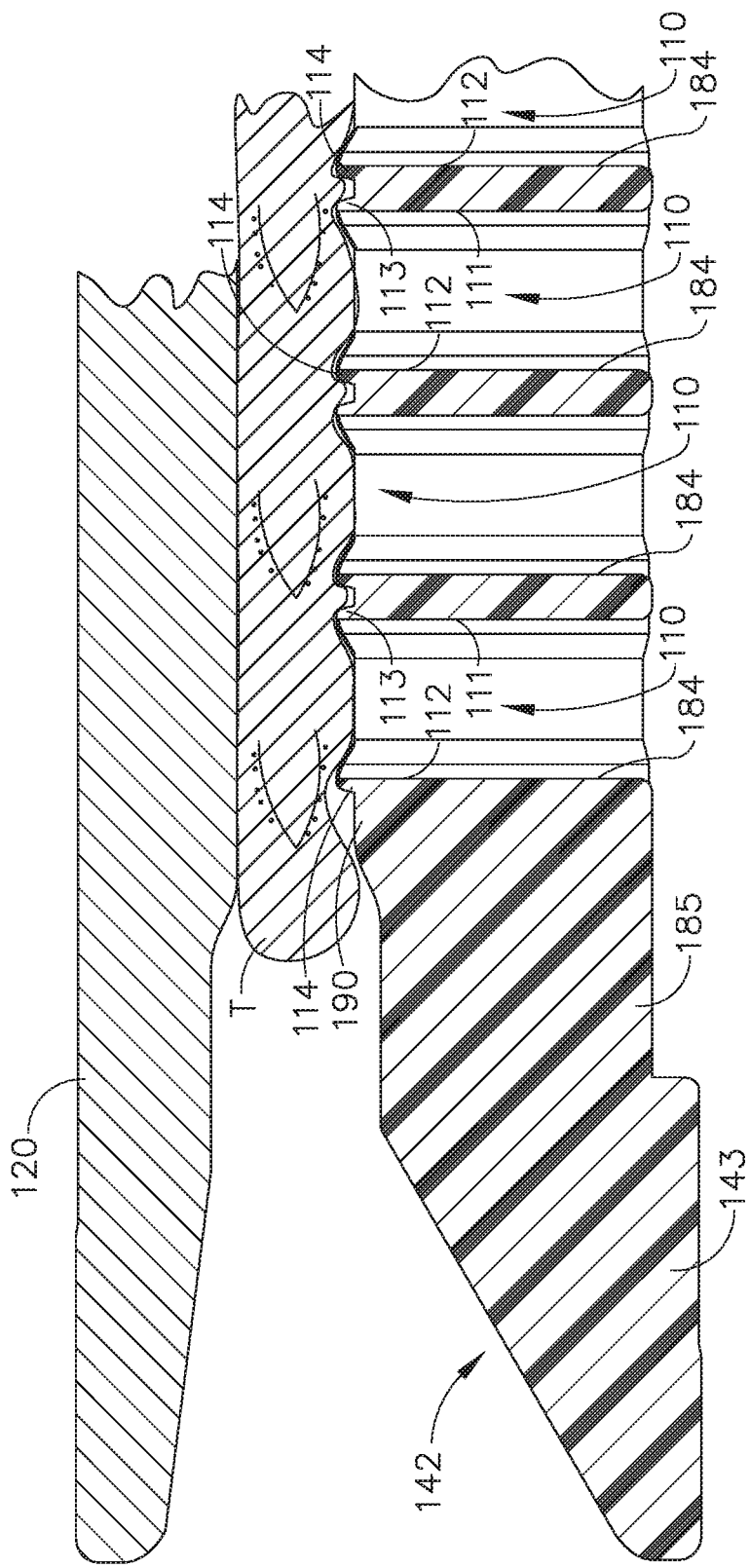
FIG. 8A is a cross-sectional view of the staple cartridge of FIG. 7.

In various embodiments, referring again to FIGS. 7 and 8, the cartridge body 185 of the staple cartridge 142 can further comprise one or more ridges, such as ridges 113, 114, and 115, for example, which can be configured to contact and compress the targeted tissue. More particularly, referring now to FIG. 8A, the anvil 120 of an end effector can be closed in order to compress the tissue T against the staple cartridge 142 wherein, in such circumstances, the tissue-contacting deck 190 and the ridges 113, 114, and 115 extending therefrom can engage the tissue. As the anvil 120 is closed, in certain circumstances, the anvil 120 can push the tissue toward the staple cartridge 142 such that the tissue first contacts the ridges 113, 114, and 115 and then contacts the cartridge deck 190. In other circumstances, the staple cartridge 142 can be positioned against the tissue such that the ridges 113, 114, and 115 contact the tissue before the tissue is contacted by the cartridge deck 190. In any event, the ridges 113, 114, and 115, once in contact in with the tissue, can prevent, or at least limit, relative movement between the tissue and the staple cartridge 142. In certain embodiments, the ridges 113, 114, and 115 can extend upwardly from a flat, or at least substantially flat, cartridge deck 190 and can define one or more pockets or channels, for example, which can be configured to receive a portion of the tissue therein and, as a result, inhibit the relative movement of the tissue in the longitudinal direction and/or the transverse direction of the end effector, especially when the tissue is at least partially compressed between the anvil 120 and the ridges 113, 114, and 115. In various embodiments, as the ridges 113, 114, and 115 extend above the cartridge deck 190, the tissue positioned intermediate the anvil 120 and the ridges 113, 114, and 115 can be compressed before the tissue positioned intermediate the anvil 120 and the cartridge deck 190 is compressed. In some such circumstances, as a result, the tissue positioned between the anvil 120 and the ridges 113, 114, and 115 can be pre-compressed, i.e., at least partially compressed before the other portions of the tissue positioned between the anvil 120 and the cartridge deck 190 are compressed. Owing to this pre-compression, in various circumstances, portions of the tissue can be controlled or prevented from slipping out of the end effector before the tissue is fully compressed as described in greater detail below.

In various embodiments, referring again to FIGS. 7 and 8, the ridges 113 extending from the cartridge deck 190 can extend around the proximal ends 111 of the staple cavity openings 110. Similarly, the ridges 114 extending from the cartridge deck 190 can extend around the distal ends 112 of the staple cavity openings 110. These proximal ridges 113 and distal ridges 114, in various embodiments, can be configured to engage the tissue positioned above and/or around the staple cavities 184 and hold these portions of the tissue in position as the tissue is being compressed and/or stapled. Stated another way, holding the tissue positioned above and/or surrounding the staple cavities 184 can provide localized control over the portions of the tissue that are going to be stapled and, as a result, prevent, or at least limit, the relative movement between these portions of the tissue and the staple cartridge 142. In various embodiments, the ridges 113 and 114 can be positioned around the openings 110 of all of the staple cavities 184 or only some of the staple cavities 184. In at least one embodiment, a cartridge body may comprise ridges 113 and 114 surrounding only the staple cavities 184 in the outermost rows of the first and second sides 145 and 147. In such embodiments, the ridges surrounding the outermost rows of staple cavities 184 may be sufficient to block the lateral movement of the tissue within the end effector. In certain embodiments, a cartridge body may only comprise proximal ridges 113 surrounding the proximal ends 111 of the proximalmost staple cavities 184 and/or distal ridges 114 surrounding the distal ends 112 of the distalmost staple cavities 184. In such embodiments, the ridges surrounding the proximalmost and distalmost staple cavities 184 may be sufficient to block the longitudinal movement of the tissue within the end effector.

In various embodiments, further to the above, each proximal ridge 113 can comprise an arcuate or curved profile, for example, which surrounds a proximal end 111 of an opening 110. The arcuate profile of each proximal ridge 113 can be defined by one radius of curvature or more than one radius of curvature. Similarly, each distal ridge 114 can comprise an arcuate or curved profile, for example, which surrounds a distal end 112 of an opening 110. The arcuate profile of each distal ridge 114 can be defined by one radius of curvature or more than one radius of curvature. In certain embodiments, further to the above, each ridge 113 and 114 can form a pocket which can receive a portion of tissue that is being compressed and prevent that portion of tissue from moving longitudinally and/or transversely relative to the staple cartridge 142. In various embodiments, the staple cartridge 142 can further comprise intermediate ridges 115 which can extend between and/or connect adjacent ridges 113 and 114 in adjacent rows of staple cavities 184. In at least one such embodiment, one or more ridges 113, 114, and 115 can co-operatively form an undulating ridge extending across the first side 145 or the second side 147 of the cartridge body 185 wherein, in at least one embodiment, the undulating ridge can extend between a center portion and a side portion of the cartridge body 142. In various embodiments, each undulating ridge can comprise a plurality of wave portions winding around the proximal and distal ends of the staple cavities 184, for example. In various embodiments, each ridge 113, 114, and 115 can comprise a height defined from the cartridge deck 190 wherein, in certain embodiments, the height of each ridge 113, 114, and 115 can be uniform, or at least substantially uniform, across the length thereof. In at least one embodiment, each ridge 113, 114, and 115 can have the same, or at least substantially the same, height.

In various embodiments, as described above, the staple cavities defined in a staple cartridge body can comprise a staple positioned therein wherein the entirety of the staple can be positioned below the top surface, or tissue-contacting surface, of the cartridge deck when the staple is in its unfired position. In certain other embodiments, at least a portion of the staple, such as the tips of the staple legs, for example, can extend above the top surface, or tissue-contacting surface, of the cartridge deck when the staples are in their unfired position. In some such embodiments, the tips of the staples can protrude from the deck and may snag on tissue as the staple cartridge is inserted into a surgical site. In at least one embodiment, referring now to FIG. 9, the ridges 113 and 114, for example, which extend above the tissue-contacting cartridge deck 190, can at least partially surround and protect the staple legs 183 of staples 187 when they extend above the cartridge deck 190 in their unfired position. Although the ridges 113 and 114 may not extend entirely around each opening 110, in various embodiments, the proximal ridge 113 may sufficiently surround one of the staple leg tips and the distal ridge 114 may sufficiently surround the other staple leg tip such that the staple leg tips do not contact the tissue prior to the tissue being compressed against the staple cartridge 142 and/or the staples 187 being ejected from the staple cartridge 142. In at least one embodiment, the staple leg tips can be positioned below the top surfaces 116 of the ridges 113 and 114. In certain embodiments, the staple leg tips can lie in a common plane with the top surfaces 116 of the ridges 113 and 114. In various embodiments, as a result of the protection afforded by the ridges 113 and 114, for example, staples having a taller staple height can be used without the staple tips protruding from the staple cartridge 142 in their unfired position. In certain embodiments, referring again to FIG. 9, the ridges 113 and 114 can extend or increase the length in which the staple legs 183 of the staples 187 can be controlled and/or supported. In at least one such embodiment, each ridge 113 and 114 can extend or increase the length in which the staple legs 183 are supported on three sides thereof. Such embodiments can prevent, or at least reduce the possibility of, the staple legs 183 from buckling when they are inserted through dense tissue, such as bronchus tissue, for example.

In various embodiments, referring again to FIG. 4, the cartridge body 85 can comprise cavities 84, slot 62, and channels 86, for example, defined therein which can reduce the strength of the cartridge body 85. In various circumstances, especially when the cartridge body 85 is compressed by the anvil 20, for example, the cartridge body 85 can deflect as a result of the load applied thereto. In at least one such embodiment, the portions of the cartridge deck 90 extending over the channels 86, for example, may be especially thin and may be especially subject to deflection and/or breakage. In certain embodiments, referring again to FIGS. 7 and 8, the ridges 113, 114, and/or 115 can be configured to strengthen and/or stiffen the cartridge body 185. In at least one such embodiment, the ridges 113 and 114, for example, can extend around the openings 110 in order to strengthen and/or stiffen the portions of the cartridge body 185 surrounding the staple cavities 184. In certain embodiments, the ridges 115, for example, can extend transversely over channels 86, or the like, defined within the cartridge body 185 such that the ridges 115 can strengthen and/or stiffen the cartridge body 185 surrounding the channels 86. In various other embodiments, the cartridge body 185 can comprise any suitable number and configuration of ridges extending therefrom in order to achieve the advantages described herein.

In various embodiments, a staple cartridge body 185 can be comprised of plastic materials, metallic materials, and/or ceramic materials, for example. Some such materials can comprise liquid crystal polymers, such as Vectra, for example, thermoplastic polymers, such as polycarbonate, ABS, Noryl, polyamides (nylons), polyethersulfones, polyetherimides, such as Ultem, for example, and/or polymer blends of two or more of the aforementioned thermoplastic polymers, for example, wherein, in various embodiments, the cartridge body 185 can be formed by an injection molding process, for example. Some such materials can comprise thermoset polymers, like thermoset polyesters, for example, investment cast stainless steels, such as 17-4 PH, for example, and/or metal Injection molded stainless steels, such as 17-4 PH, for example. In at least one such embodiment, the ridges 113, 114, and/or 115 can be integrally formed with the cartridge deck 190 of the cartridge body 185. In certain embodiments, the ridges 113, 114, and/or 115 can be attached to the cartridge deck 190 by at least one adhesive, for example.

Figure 12:
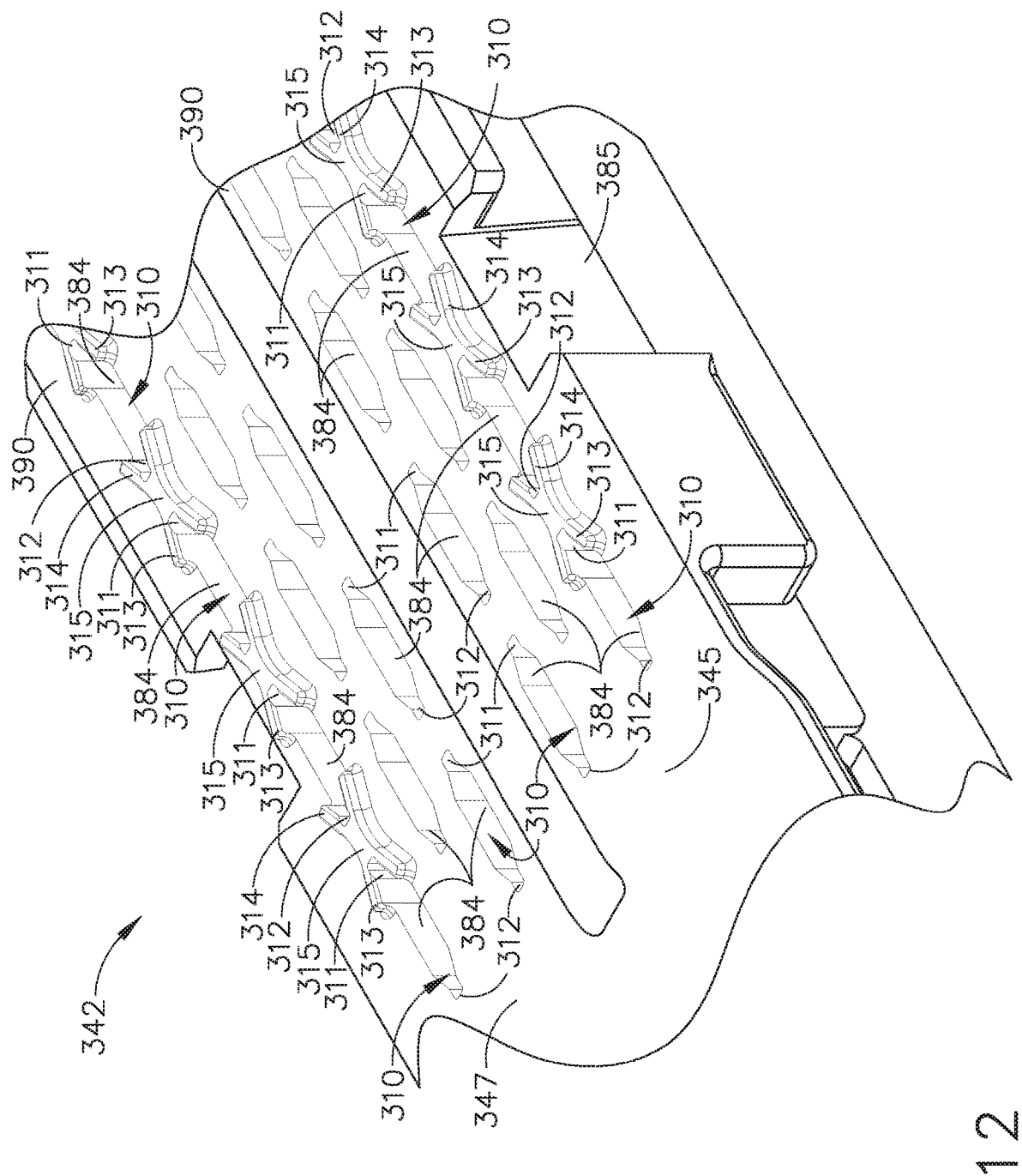
FIG. 12 is a partial perspective view of a staple cartridge in accordance with at least one alternative embodiment comprising a plurality of ridges surrounding the proximal and distal ends of staple cavity openings defined in a cartridge body.
Figure 13:
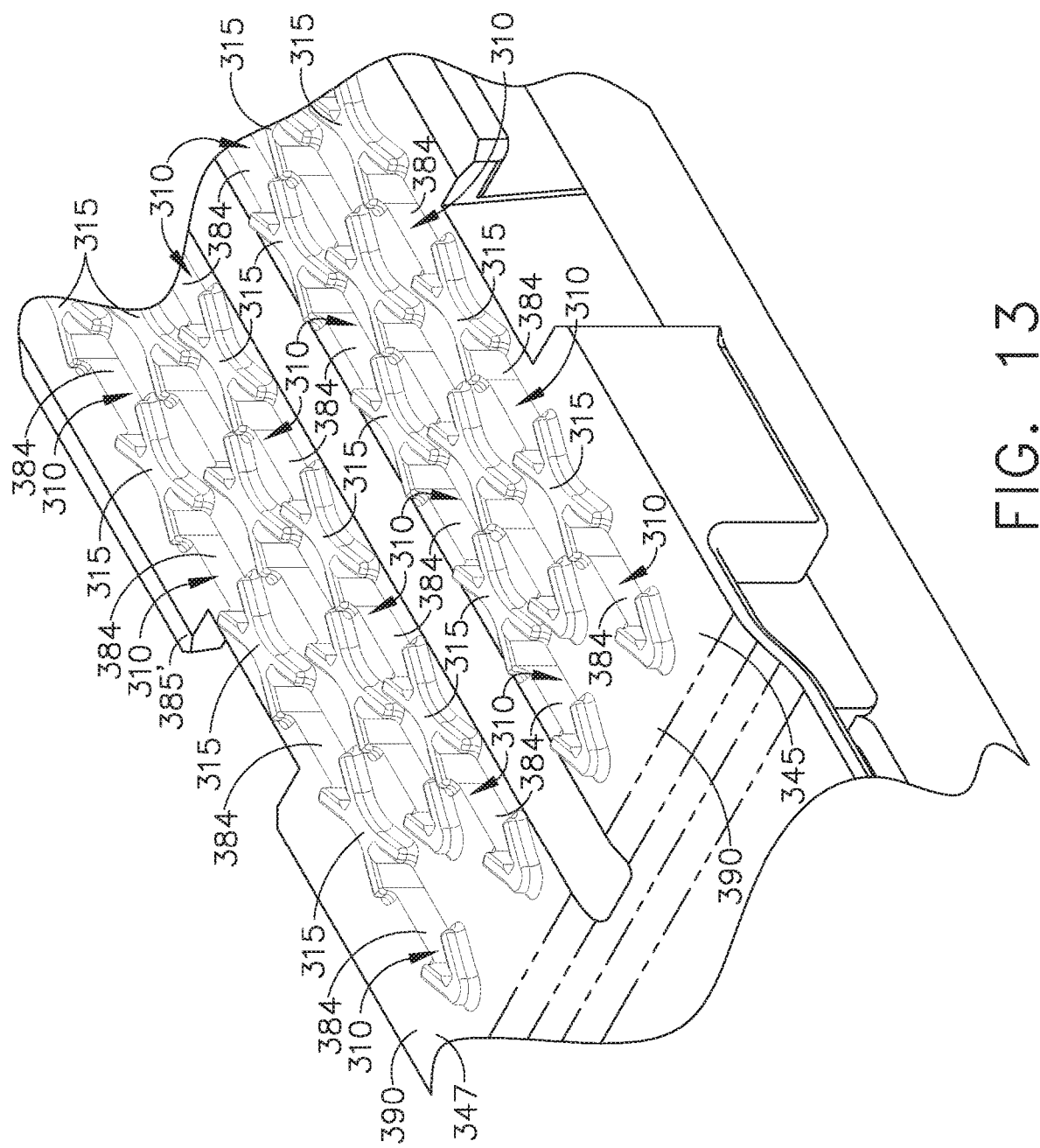
FIG. 13 is a partial perspective view of a staple cartridge in accordance with at least one alternative embodiment comprising a plurality of ridges surrounding the proximal and distal ends of staple cavity openings defined in a cartridge body.

In various embodiments, referring now to FIG. 12, a staple cartridge, such as staple cartridge 342, for example, can comprise a cartridge body 385, a plurality of staple cavities 384 defined in the cartridge body 385, and a staple positioned in each of the staple cavities 384. In certain embodiments, the cartridge body 385 can further comprise a first side 345 comprising a first group of staple cavities 384, a second side 347 comprising a second group of staple cavities 384, and a cartridge deck 390. In various embodiments, the cartridge body 385 can further comprise a plurality of ridges 315 extending from the cartridge deck 390 which can be positioned intermediate adjacent staple cavities 384 in a row of staple cavities 384. In at least one embodiment, each ridge 315 can comprise a cross-shaped or X-shaped configuration, for example. In at least one such embodiment, for example, each ridge 315 can comprise a V-shaped portion 313 which can at least partially surround a proximal end 311 of a staple cavity opening 310 and, in addition, a V-shaped portion 314 which can at least partially surround a distal end 312 of another staple cavity opening 310. In certain embodiments, only the outermost rows of staple cavities 384 in cartridge body 385 can be at least partially surrounded by ridges 315. In certain other embodiments, referring now to FIG. 13, a staple cartridge body 385' can comprise ridges 315 which at least partially surround the opening 310 of every staple cavity 384 in the cartridge body. In any event, in various embodiments, each ridge 315 can be configured to compress and control tissue positioned against the staple cartridge 342 as described above and/or surround the staple legs of the staples extending above the deck 390.

Figure 16:
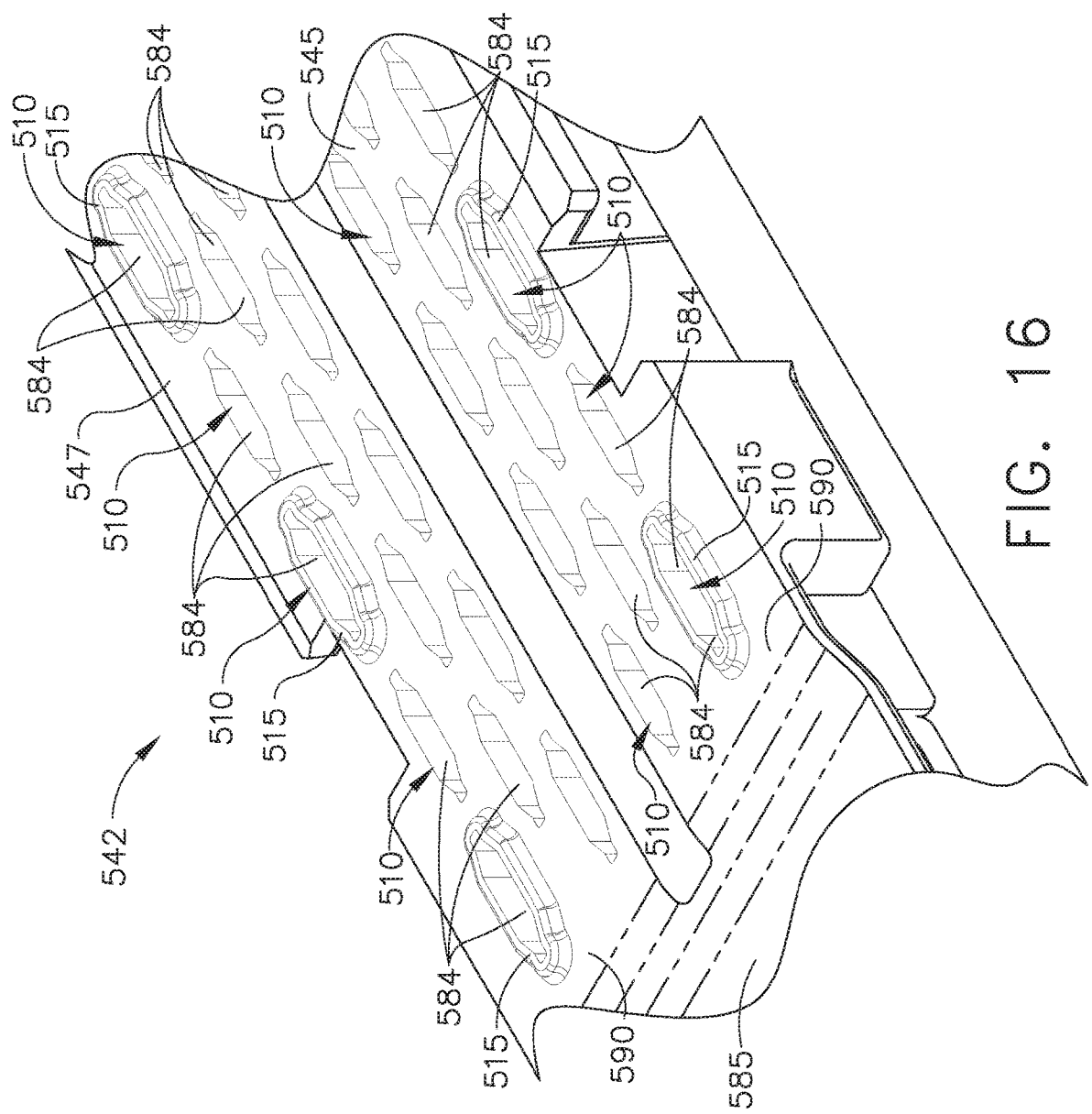
FIG. 16 is a partial perspective view of a staple cartridge in accordance with at least one alternative embodiment comprising a plurality of ridges entirely surrounding staple cavity openings defined in a cartridge body.
Figure 16A:
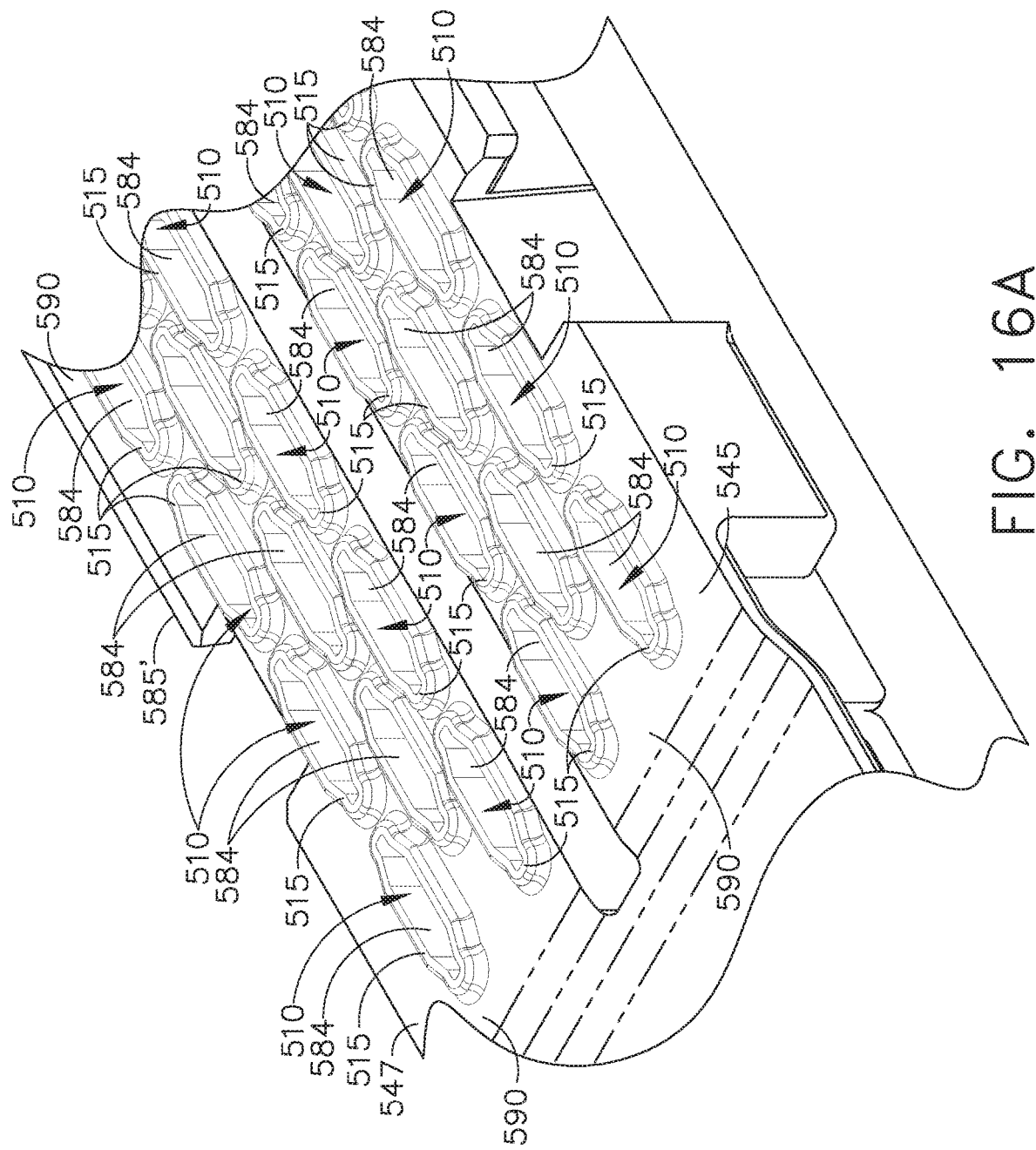
FIG. 16A is a partial perspective view of a staple cartridge in accordance with at least one alternative embodiment comprising a plurality of ridges entirely surrounding staple cavity openings defined in a cartridge body.

In various embodiments, referring now to FIG. 16, a staple cartridge, such as staple cartridge 542, for example, can comprise a cartridge body 585, a plurality of staple cavities 584 defined in the cartridge body 585, and a staple positioned in each of the staple cavities 584. In certain embodiments, the cartridge body 585 can further comprise a first side 545 comprising a first group of staple cavities 584, a second side 547 comprising a second group of staple cavities 584, and a cartridge deck 590. In various embodiments, the cartridge body 585 can further comprise a plurality of ridges 515 extending from the cartridge deck 590, wherein each ridge 515 can entirely surround or encompass a staple cavity opening 510. As illustrated in FIG. 16, some cavity openings 510 in the cartridge body 585 may not be surrounded by a ridge 515; whereas, in various alternative embodiments, referring now to FIG. 16A, every cavity opening 510 in a cartridge body 585' can be surrounded by a ridge 515. Various embodiments are contemplated where a cartridge body comprises a first group of staple cavities 584 which are surrounded by a ridge 515 and a second group of staple cavities 584 which are not surrounded by a ridge 515, wherein staples having a taller staple height can be positioned in the first group of staple cavities 584 and wherein staples having a shorter staple height can be positioned in the second group of staple cavities 584 such that neither the taller staples nor the shorter staples protrude from the staple cartridge 542. In at least one such embodiment, for example, the cartridge body can be configured to utilize taller staples in one row of staple cavities 584 and shorter staples in another row of staple cavities 584. In certain embodiments, ridges 515 can surround all of the staple cavities 584 in the outermost rows of staple cavities 584 in the cartridge body such that taller staples can be utilized in the outermost rows and shorter staples can be utilized in the innermost rows and/or intermediate rows of staple cavities 584, for example.

Figure 14:
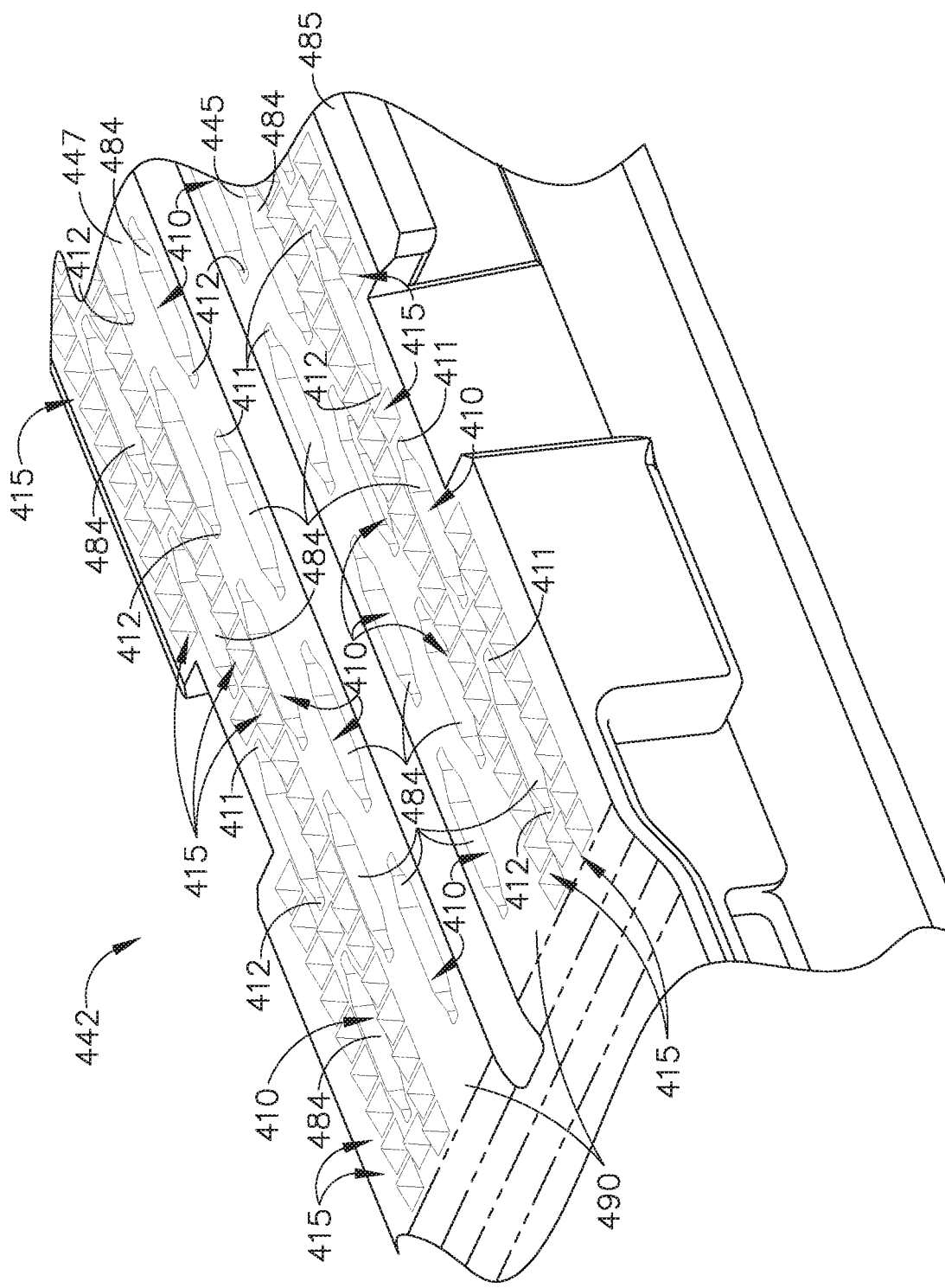
FIG. 14 is a partial perspective view of a staple cartridge in accordance with at least one alternative embodiment comprising a plurality of knurled ridges extending from a cartridge body.
Figure 15:
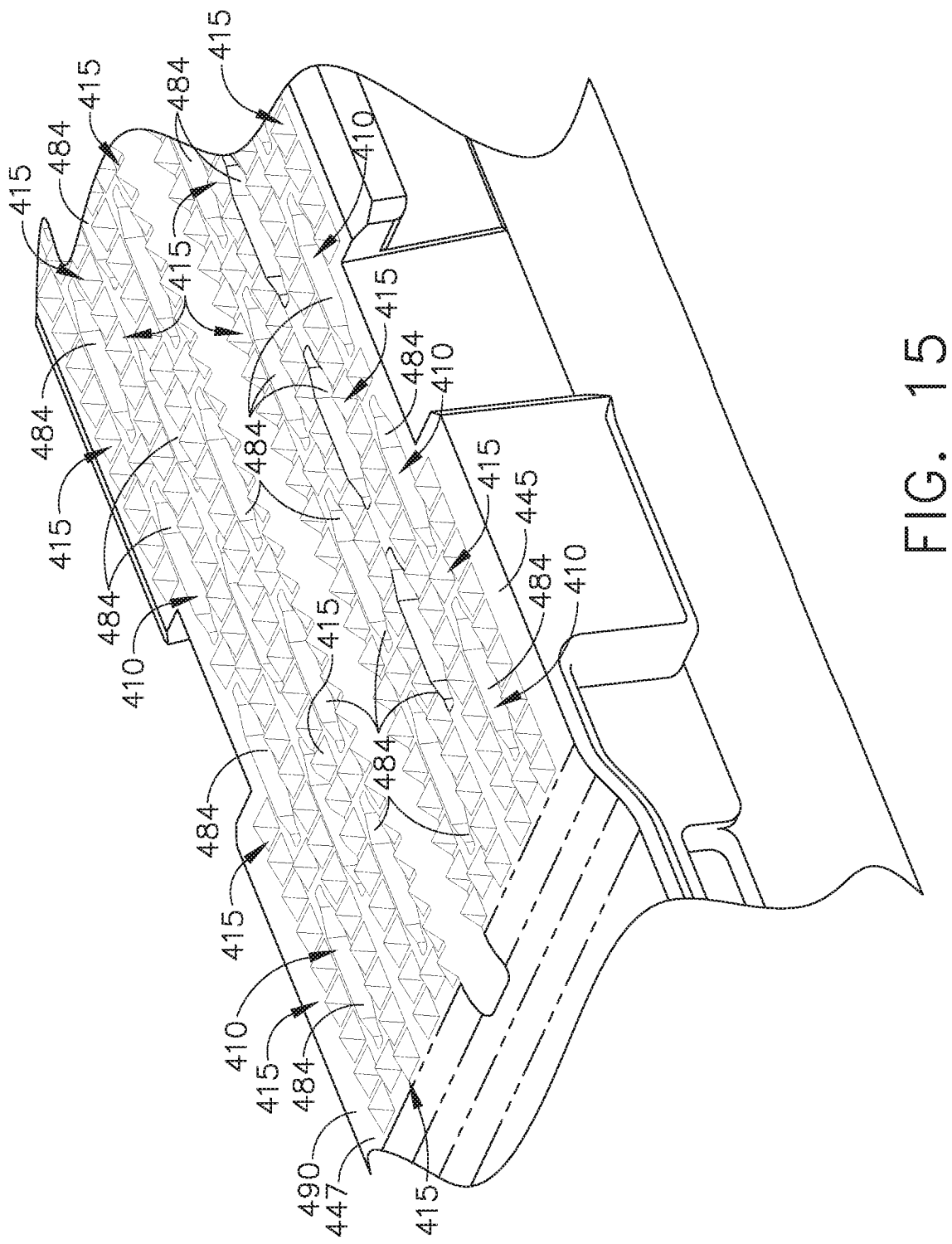
FIG. 15 is a partial perspective view of a staple cartridge in accordance with at least one alternative embodiment comprising a plurality of knurled ridges extending from a cartridge body.
Figure 15A:
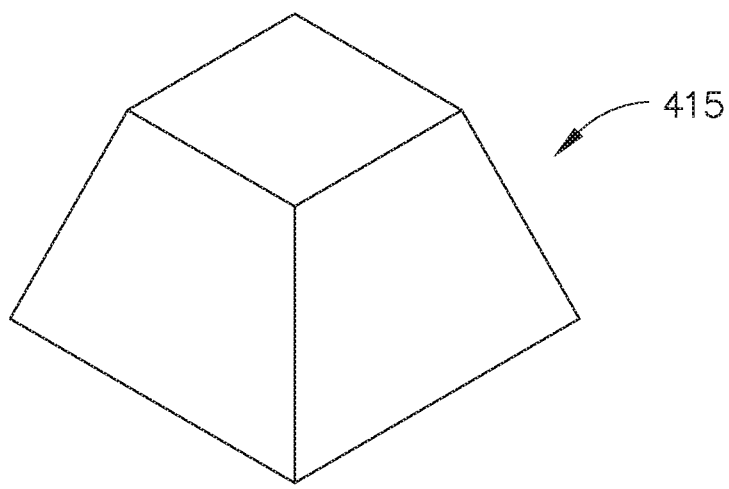
FIG. 15A is a perspective view of a pyramidal knurl in accordance with at least one embodiment.
Figure 15B:
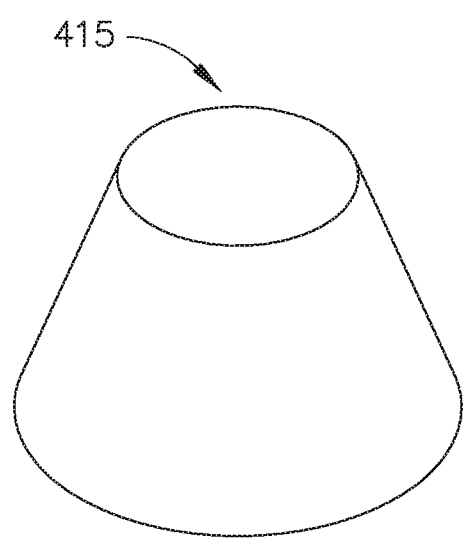
FIG. 15B is a perspective view of a frustoconical knurl in accordance with at least one embodiment.
Figure 15C:
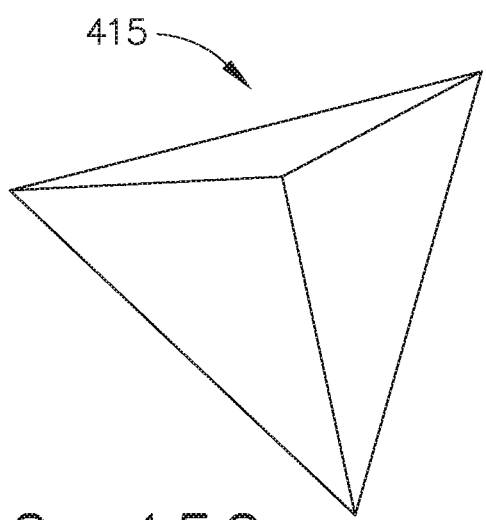
FIG. 15C is a perspective view of a triangular knurl in accordance with at least one embodiment.

In various embodiments, referring now to FIG. 14, a staple cartridge, such as staple cartridge 442, for example, can comprise a cartridge body 485, a plurality of staple cavities 484 defined in the cartridge body 485, and a staple positioned in each of the staple cavities 484. In certain embodiments, the cartridge body 485 can further comprise a first side 445 comprising a first group of staple cavities 484, a second side 447 comprising a second group of staple cavities 484, and a cartridge deck 490. In various embodiments, the cartridge body 445 can further comprise a plurality of ridges 415 extending from the cartridge deck 490, wherein each ridge 415 can comprise a plurality, or array, of knurls. In use, an anvil can be utilized to position tissue against the knurls such that the tissue conforms to the contour of the knurls. In various embodiments, each ridge 415 can comprise a plurality of pyramidal-shaped, or diamond-shaped, knurls, for example, at least partially surrounding one or more staple cavity openings 410 wherein, in at least one embodiment, the pyramidal-shaped knurls can point upwardly from the cartridge deck 490. In at least one embodiment, each pyramidal knurl can comprise four triangular sides which can converge together to form a sharp point. In certain embodiments, referring to FIG. 15A, the pyramidal knurls of ridges 415 can be truncated, wherein the top of each knurl can comprise a flat top surface surrounded by inclined sides. Although four-sided pyramidal knurls can be utilized, referring now to FIG. 15C, other pyramidal shapes are contemplated which have less than four sides or more than four sides, such as three sides, for example. In various embodiments, one or more ridges 415 can comprise a plurality of cone-shaped knurls, wherein each cone-shaped knurl can comprise a circular, or at least substantially circular, base which tapers upwardly to form a sharp point. In certain embodiments, referring now to FIG. 15B, the cone-shaped knurls can be truncated, wherein the top of each knurl can comprise a flat top surface surrounded by an annular side. In various embodiments, referring again to FIG. 14, the knurls of the ridges 415 can extend along the lateral sides of the staple cavity openings 410 and/or between adjacent staple cavity openings 410. In at least one embodiment, the knurls can extend around the proximal ends 411 and/or the distal ends 412 of the staple cavity openings 410. In certain embodiments, the knurls of ridges 415 may only surround some of the staple cavities 484 while, in certain other embodiments, referring to FIG. 15, the knurls of ridges 415 may cover the entirety, or at least the substantial entirety, of the cartridge deck 490, for example.

Figure 10:
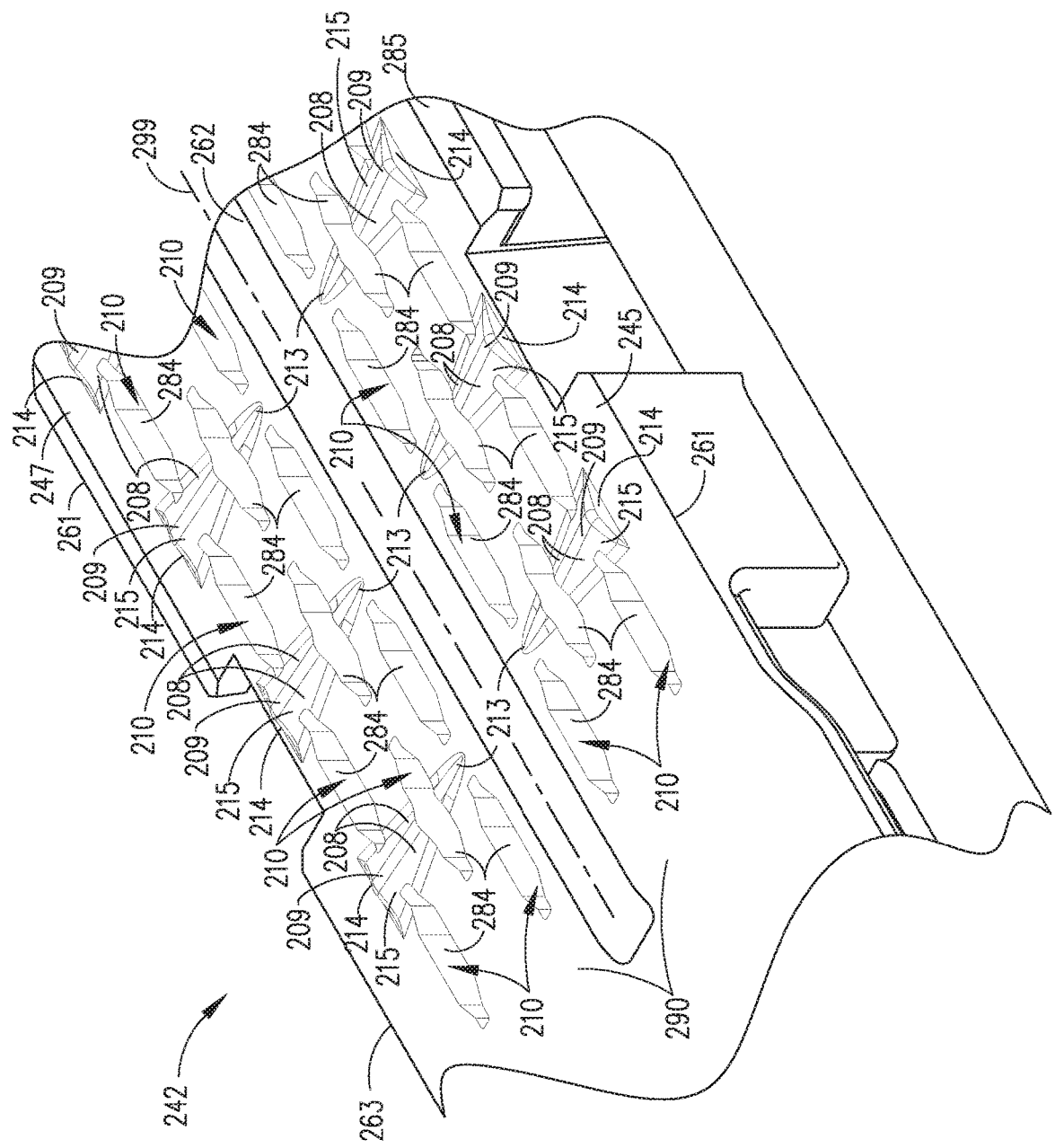
FIG. 10 is a partial perspective view of a staple cartridge in accordance with at least one alternative embodiment comprising a plurality of transverse ridges extending from a cartridge body.
Figure 11:
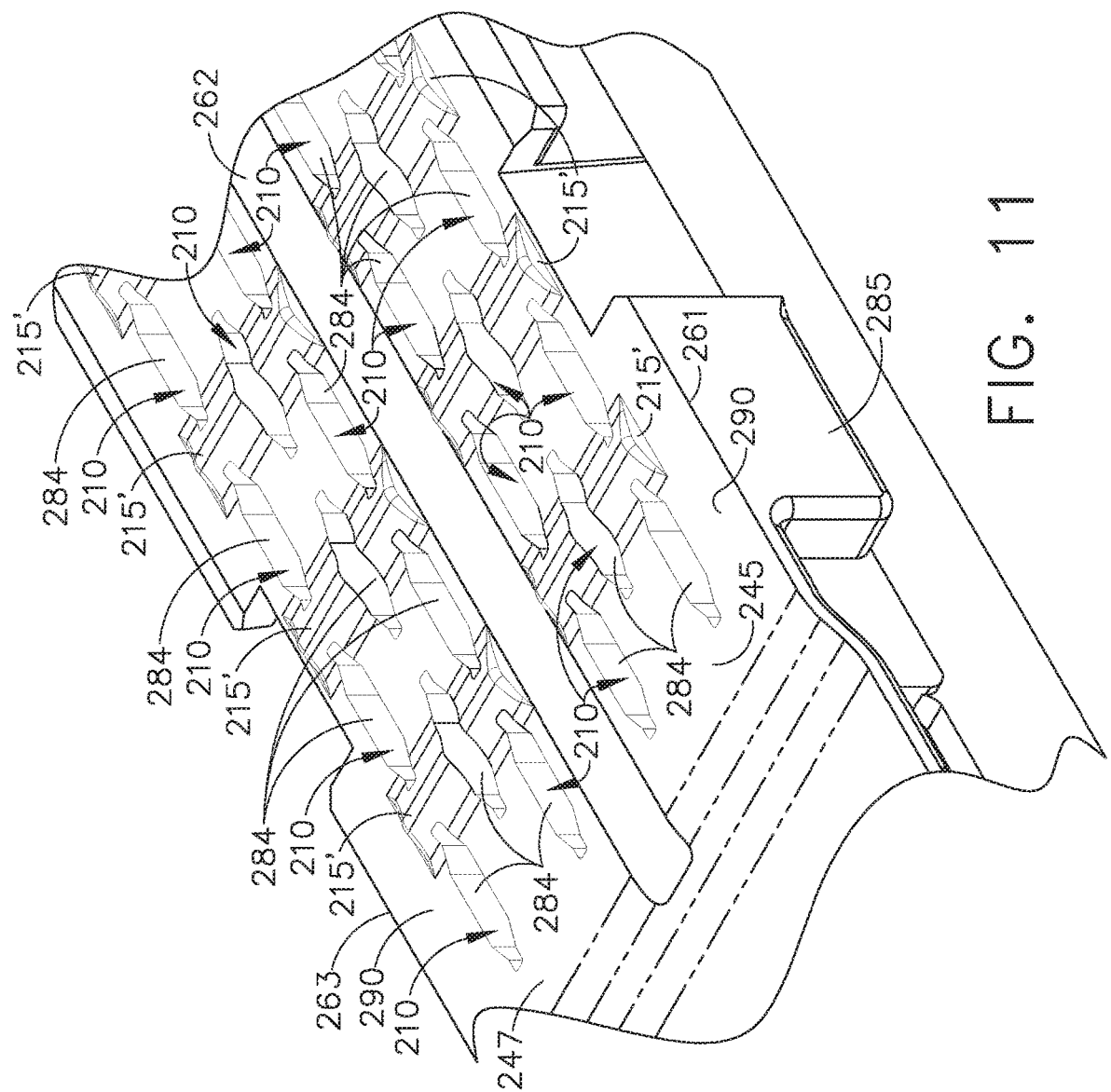
FIG. 11 is a partial perspective view of a staple cartridge in accordance with at least one alternative embodiment comprising a plurality of transverse ridges extending from a cartridge body.

In various embodiments, referring now to FIG. 10, a staple cartridge, such as staple cartridge 242, for example, can comprise a cartridge body 285, a plurality of staple cavities 284 defined in the cartridge body 285, and a staple positioned in each of the staple cavities 284. In certain embodiments, the cartridge body 285 can further comprise a first side 245 comprising a first group of staple cavities 284, a second side 247 comprising a second group of staple cavities 284, and a cartridge deck 290. In various embodiments, the cartridge body 285 can further comprise a plurality of ridges, or bumps, 215 extending from the cartridge deck 290. In at least one such embodiment, each ridge 215 can extend transversely between a center, or middle, portion of the cartridge body 245 positioned adjacent to a knife slot 262 and a lateral portion of the cartridge body 245. More particularly, referring specifically to the first side 245 of the cartridge body 285, each ridge 215 can comprise a first end 213 positioned adjacent to the knife slot 262 and a second end 214 positioned adjacent to the first side 261 of the cartridge body 285. Similarly, referring now to the second side 247 of the cartridge body 285, each ridge 215 can comprise a first end 213 positioned adjacent to the knife slot 262 and a second end 214 positioned adjacent to the second side 263 of the cartridge body 285. In at least one embodiment, each ridge 215 can comprise a height measured from the deck 290 wherein, in at least one such embodiment, the height of each ridge 215 can vary along the length thereof. In certain embodiments, the second end 214 can be taller than the first end 213 and the height of each ridge 215 can taper between the second end 214 and the first end 213. In certain alternative embodiments, although not illustrated, the first end 213 of the ridge 215 can be taller than the second end 214. In at least one embodiment, the height of each ridge 215 can taper linearly, or at least substantially linearly, between the ends 213 and 214. In at least one such embodiment, the height of each ridge 215 can taper between a maximum height at the second end 214 down to no height at all at the first end 213. In certain embodiments, the height of each ridge 215 can vary geometrically between the ends 213 and 214. In certain alternative embodiments, referring now to FIG. 11, each ridge 215' can comprise a uniform height across the length thereof.

As described above, the inner ends 213 of the ridges 215 can be shorter than the outer ends 214 of the ridges 215. In various circumstances, as a result, the inner ends 213 can apply less pressure to the tissue clamped between an anvil and the staple cartridge 242 as compared to the outer ends 214. In various embodiments, as described above, each ridge 215 can extend transversely across the cartridge deck 290. In certain embodiments, each ridge 215 can extend along a ridge axis which transects a longitudinal axis 299 of the cartridge body 285. In at least one such embodiment, the ridge axes can be perpendicular, or at least substantially perpendicular, to the longitudinal axis 299. In various embodiments, the staple cavities 284 can be arranged in a plurality of rows, wherein each row of staple cavities 284 can be defined along a longitudinal axis which can be parallel to, or at least substantially parallel to, the longitudinal axis 299. In at least one embodiment, the ridge axes of the ridges 215 can extend in a direction which transect the longitudinal axes of the staple cavities 284. In at least one such embodiment, the ridge axes of the ridges 215 can extend in a direction which is perpendicular, or at least substantially perpendicular, to the longitudinal axes of the staple cavities 284. In various embodiments, referring again to FIG. 10, each ridge 215 can comprise a crest 209 and, in addition, sloped surfaces 208 extending between the crest 209 and the cartridge deck 290. In certain embodiments, each sloped surface 208 can comprise one or more flat surfaces, curved surfaces, concave surfaces, and/or convex surfaces, for example. In various embodiments, each ridge 215 can extend along a path which extends across one or more openings 210 of the staple cavities 284. In at least one such embodiment, such openings 210 can extend upwardly through the ridges 215. As the ridges 215 extend transversely across the cartridge deck 290, the ridges 215, similar to the ridges 115, can increase the strength and/or stiffness of the cartridge body 285.

Figure 17:
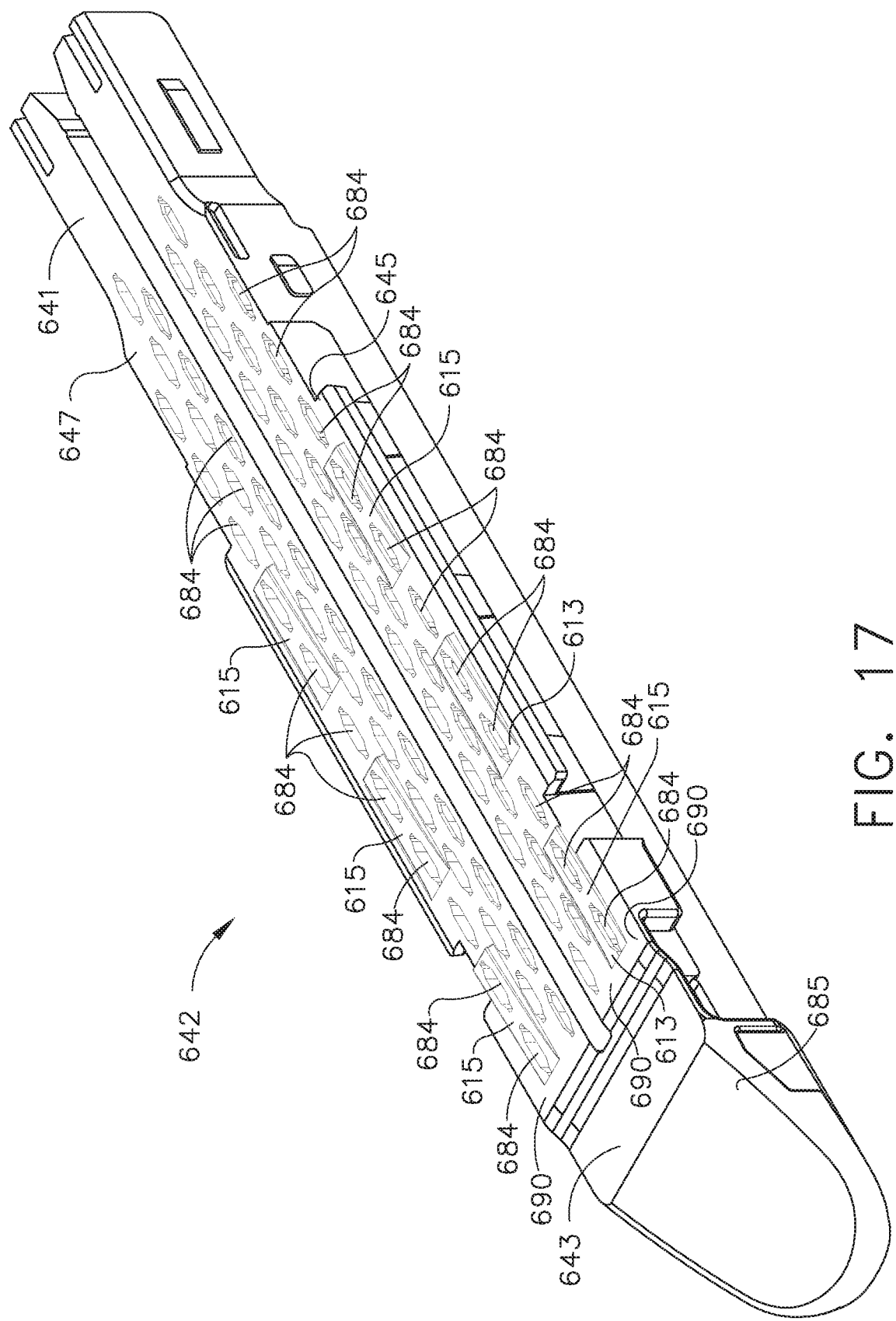
FIG. 17 is a perspective view of a staple cartridge in accordance with at least one alternative embodiment comprising a plurality of longitudinal ridges extending from a cartridge body.
Figure 18:
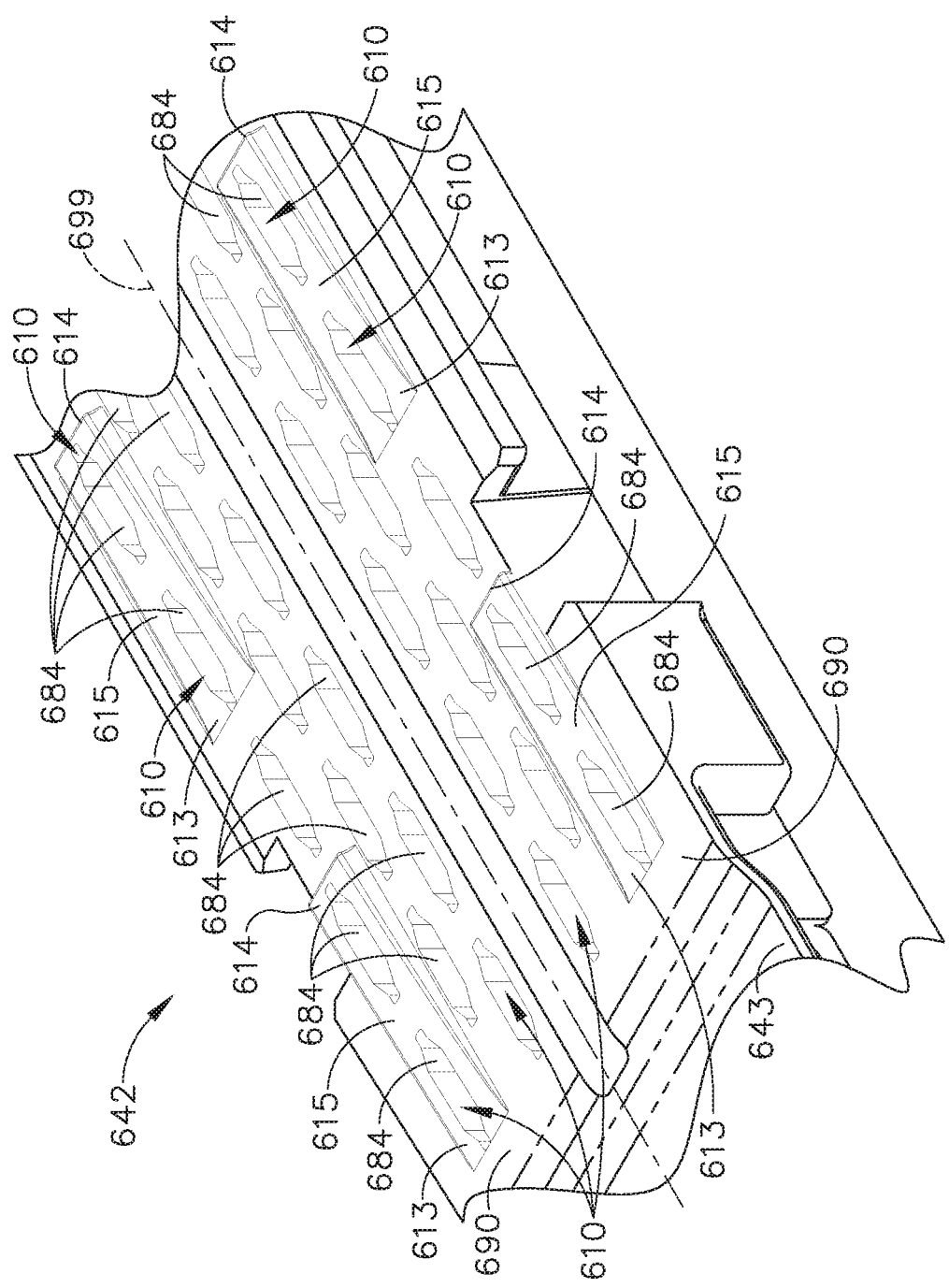
FIG. 18 is a detail view of the staple cartridge of FIG. 17.

In various embodiments, referring now to FIGS. 17 and 18, a staple cartridge, such as staple cartridge 642, for example, can comprise a cartridge body 685, a plurality of staple cavities 684 defined in the cartridge body 685, and a staple positioned in each of the staple cavities 684. In certain embodiments, the cartridge body 685 can further comprise a first side 645 comprising a first group of staple cavities 684, a second side 647 comprising a second group of staple cavities 684, and a cartridge deck 690. In various embodiments, the cartridge body 685 can further comprise a plurality of ridges, or bumps, 615 extending from the cartridge deck 690. In at least one such embodiment, each ridge 615 can extend in a longitudinal direction, wherein each ridge 615 can comprise a distal end 613 and a proximal end 614, wherein the distal end 613 of the ridge 615 can positioned closer to the distal end 643 of the cartridge body 685, and wherein the proximal end 614 of the ridge 615 can be positioned closer to the proximal end 641. In at least one embodiment, each ridge 615 can comprise a height measured from the deck 690 wherein, in at least one such embodiment, the height of each ridge 615 can vary along the length thereof. In certain embodiments, the proximal end 614 can be taller than the distal end 613 and the height of each ridge 615 can taper between the proximal end 614 and the distal end 613. In certain alternative embodiments, although not illustrated, the distal end 613 of the ridge 615 can be taller than the proximal end 614. In at least one embodiment, the height of each ridge 615 can taper linearly, or at least substantially linearly, between the ends 613 and 614. In at least one such embodiment, the height of each ridge 615 can taper between a maximum height at the proximal end 614 down to no height at all at the distal end 613. In certain embodiments, the height of each ridge 615 can vary geometrically between the ends 613 and 614. In certain alternative embodiments, each ridge 615 can comprise a uniform height across the length thereof.

As described above, the distal ends 613 of the ridges 615 can be shorter than the proximal ends 614 of the ridges 615. In various circumstances, as a result, the distal ends 613 can apply less pressure to the tissue clamped between an anvil and the staple cartridge 642 as compared to the proximal ends 614. In various embodiments, as described above, each ridge 615 can extend longitudinally across the cartridge deck 690. In certain embodiments, each ridge 615 can extend along a ridge axis which is parallel to, or at least substantially parallel to, a longitudinal axis 699 of the cartridge body 685. In various embodiments, the staple cavities 684 can be arranged in a plurality of rows, wherein each row of staple cavities 684 can be defined along a longitudinal axis which can be parallel to, or at least substantially parallel to, the ridge axes of ridges 615. In at least one embodiment, referring again to FIG. 18, each ridge 615 can comprise a ramped surface which can comprise one or more flat surfaces, curved surfaces, concave surfaces, and/or convex surfaces, for example. In at least one such embodiment, the bottom of the ramped surface can face distally which can facilitate the sliding of tissue across the staple cartridge 642 when the tissue is positioned in the end effector. In various embodiments, each ridge 615 can extend along a path which extends across one or more openings 610 of the staple cavities 684. In at least one such embodiment, such openings 610 can extend upwardly through the ridges 615. As the ridges 615 extend transversely across the cartridge deck 690, the ridges 615 can increase the strength and/or stiffness of the cartridge body 685.

In various embodiments, further to the above, a surgical staple can be comprised of titanium, such as titanium wire, for example. In certain embodiments, a surgical staple can be comprised of an alloy comprising titanium, aluminum, and/or vanadium, for example. In at least one embodiment, the surgical staple can be comprised of surgical stainless steel and/or an alloy comprised of cobalt and chromium, for example. In any event, the surgical staple can be comprised of metal, such as titanium, and a metal oxide outer surface, such as titanium oxide, for example. In various embodiments, the metal oxide outer surface can be coated with a material. In certain embodiments, the coating material can be comprised of polytetrafluoroethylene (PTFE), such as TEFLON®, and/or a tetrafluoroethylene (TFE) such as ethylene-tetrafluoroethylene (ETFE), perfluoralkoxyethylene-tetrafluoroethylene (PFA), and/or Fluorinated Ethylene Propylene (FEP), for example. Certain coatings can comprise silicon. In various embodiments, such coating materials can prevent, or at least inhibit, further oxidation of the metal. In certain embodiments, the coating materials can provide one or more lubricious surfaces against which the anvil, or staple pockets, can contact the staples in order to reduce the friction force therebetween. In various circumstances, lower friction forces between the staples and the staple pockets can reduce the force required to deform the staples.

Although the various embodiments of the devices have been described herein in connection with certain disclosed embodiments, many modifications and variations to those embodiments may be implemented. Also, where materials are disclosed for certain components, other materials may be used. Furthermore, according to various embodiments, a single component may be replaced by multiple components, and multiple components may be replaced by a single component, to perform a given function or functions. The foregoing description and following claims are intended to cover all such modification and variations.

The devices disclosed herein can be designed to be disposed of after a single use, or they can be designed to be used multiple times. In either case, however, the device can be reconditioned for reuse after at least one use. Reconditioning can include any combination of the steps of disassembly of the device, followed by cleaning or replacement of particular pieces, and subsequent reassembly. In particular, the device can be disassembled, and any number of the particular pieces or parts of the device can be selectively replaced or removed in any combination. Upon cleaning and/or replacement of particular parts, the device can be reassembled for subsequent use either at a reconditioning facility, or by a surgical team immediately prior to a surgical procedure. Those skilled in the art will appreciate that reconditioning of a device can utilize a variety of techniques for disassembly, cleaning/replacement, and reassembly. Use of such techniques, and the resulting reconditioned device, are all within the scope of the present application.

Preferably, the invention described herein will be processed before surgery. First, a new or used instrument is obtained and if necessary cleaned. The instrument can then be sterilized. In one sterilization technique, the instrument is placed in a closed and sealed container, such as a plastic or TYVEK® bag. The container and instrument are then placed in a field of radiation that can penetrate the container, such as gamma radiation, x-rays, or high-energy electrons. The radiation kills bacteria on the instrument and in the container. The sterilized instrument can then be stored in the sterile container. The sealed container keeps the instrument sterile until it is opened in the medical facility.

While this invention has been described as having exemplary designs, the present invention may be further modified within the spirit and scope of the disclosure. This application is therefore intended to cover any variations, uses, or adaptations of the invention using its general principles. Further, this application is intended to cover such departures from the present disclosure as come within known or customary practice in the art to which this invention pertains.

Any patent, publication, or other disclosure material, in whole or in part, that is said to be incorporated by reference herein is incorporated herein only to the extent that the incorporated materials does not conflict with existing definitions, statements, or other disclosure material set forth in this disclosure. As such, and to the extent necessary, the disclosure as explicitly set forth herein supersedes any conflicting material incorporated herein by reference. Any material, or portion thereof, that is said to be incorporated by reference herein, but which conflicts with existing definitions, statements, or other disclosure material set forth herein will only be incorporated to the extent that no conflict arises between that incorporated material and the existing disclosure material.

What is claimed is:

1. A fastener cartridge, comprising:
a cartridge body, comprising:
a deck comprising a variable height tissue compression surface, wherein a longitudinal slot is defined through at least a portion of said variable height tissue compression surface; and
fastener cavities, comprising:
a first fastener cavity defined in said variable height tissue compression surface on a first side of said longitudinal slot; and
a second fastener cavity defined in said variable height tissue compression surface on the first side of said longitudinal slot, wherein said first fastener cavity is laterally offset from said second fastener cavity; and
unfired fasteners, comprising:
a first unfired fastener removably positioned in said first fastener cavity, wherein said first unfired fastener comprises a first height; and
a second unfired fastener removably positioned in said second fastener cavity,
wherein said second unfired fastener comprises a second height, and wherein said first height and said second height are different;
wherein said variable height tissue compression surface is configured to provide targeted tissue compression between said first unfired fastener and said second unfired fastener.

2. A fastener cartridge, comprising:
a cartridge body, comprising:
a deck comprising a variable height tissue compression surface, wherein a longitudinal slot is defined through at least a portion of said variable height tissue compression surface; and
fastener cavities, comprising:
a first fastener cavity defined in said variable height tissue compression surface on a first side of said longitudinal slot; and
a second fastener cavity defined in said variable height tissue compression surface on the first side of said longitudinal slot; and
unfired fasteners, comprising:
a first unfired fastener removably positioned in said first fastener cavity, wherein said first unfired fastener comprises a first height; and
a second unfired fastener removably positioned in said second fastener cavity,
wherein said second unfired fastener comprises a second height, and wherein said first height and said second height are different;
wherein said variable height tissue compression surface is configured to provide targeted tissue compression between said first unfired fastener and said second unfired fastener, and wherein said variable height tissue compression surface comprises a peak between said first unfired fastener and said second unfired fastener.

3. A fastener cartridge, comprising:
a cartridge body, comprising:
a deck comprising a variable height tissue compression surface, wherein a longitudinal slot is defined through at least a portion of said variable height tissue compression surface; and
fastener cavities, comprising:
a first fastener cavity defined in said variable height tissue compression surface on a first side of said longitudinal slot; and
a second fastener cavity defined in said variable height tissue compression surface on the first side of said longitudinal slot;
unfired fasteners, comprising:
a first unfired fastener removably positioned in said first fastener cavity, wherein said first unfired fastener comprises a first height; and
a second unfired fastener removably positioned in said second fastener cavity, wherein said second unfired fastener comprises a second height, and wherein said first height and said second height are different; and
a sled configured to fire said unfired fasteners from said fastener cavities during a firing stroke;
wherein said variable height tissue compression surface is configured to provide targeted tissue compression between said first unfired fastener and said second unfired fastener.

4. The fastener cartridge of claim 3, further comprising a cutting edge configured to move along said longitudinal slot during the firing stroke.

5. A fastener cartridge, comprising:
a cartridge body, comprising:
a deck comprising a variable height tissue compression surface, wherein a longitudinal slot is defined through at least a portion of said variable height tissue compression surface; and
    fastener cavities, comprising:
        a first fastener cavity defined in said variable height tissue compression surface on a first side of said longitudinal slot; and
        a second fastener cavity defined in said variable height tissue compression surface on the first side of said longitudinal slot; and
    unfired fasteners, comprising:
        a first unfired fastener removably positioned in said first fastener cavity, wherein said first unfired fastener comprises a first height; and
        a second unfired fastener removably positioned in said second fastener cavity, wherein said second unfired fastener comprises a second height, and wherein said first height and said second height are different;
    wherein said unfired fasteners comprise B-form staples; and
    wherein said variable height tissue compression surface is configured to provide targeted tissue compression between said first unfired fastener and said second unfired fastener.

6. A fastener cartridge, comprising:
    a cartridge body, comprising:
        a deck comprising an uneven tissue compression surface, wherein a longitudinal slot is defined through at least a portion of said uneven tissue compression surface; and
        fastener cavities, comprising:
            a first fastener cavity defined in said uneven tissue compression surface on a first side of said longitudinal slot; and
            a second fastener cavity defined in said uneven tissue compression surface on the first side of said longitudinal slot; and
        unfired fasteners, comprising:
            a first unfired fastener removably positioned in said first fastener cavity and comprising a first height; and
            a second unfired fastener removably positioned in said second fastener cavity and comprising a second height, wherein said first height and said second height are different;
    wherein said uneven tissue compression surface comprises at least one peak between said first fastener cavity and said second fastener cavity, wherein said uneven tissue compression surface is configured to provide variable compression longitudinally along a portion of said deck.

7. A fastener cartridge, comprising:
    a cartridge body, comprising:
        a deck comprising an uneven tissue compression surface, wherein a longitudinal slot is defined through at least a portion of said uneven tissue compression surface; and
        fastener cavities, comprising:
            a first fastener cavity defined in said uneven tissue compression surface on a first side of said longitudinal slot; and
            a second fastener cavity defined in said uneven tissue compression surface on the first side of said longitudinal slot; and
        unfired fasteners, comprising:
            a first unfired fastener removably positioned in said first fastener cavity and comprising a first height; and
            a second unfired fastener removably positioned in said second fastener cavity and comprising a second height, wherein said first height and said second height are different;
    wherein said uneven tissue compression surface comprises at least one peak between said first fastener cavity and said second fastener cavity, wherein said uneven tissue compression surface is configured to provide variable compression laterally along a portion of said deck.

8. A fastener cartridge, comprising:
    a cartridge body, comprising:
        a deck comprising an uneven tissue compression surface, wherein a longitudinal slot is defined through at least a portion of said uneven tissue compression surface; and
        fastener cavities, comprising:
            a first fastener cavity defined in said uneven tissue compression surface on a first side of said longitudinal slot; and
            a second fastener cavity defined in said uneven tissue compression surface on the first side of said longitudinal slot, wherein said first fastener cavity is laterally offset from said second fastener cavity; and
    unfired fasteners, comprising:
        a first unfired fastener removably positioned in said first fastener cavity and comprising a first height; and
        a second unfired fastener removably positioned in said second fastener cavity and comprising a second height, wherein said first height and said second height are different;
    wherein said uneven tissue compression surface comprises at least one peak between said first fastener cavity and said second fastener cavity.

9. A fastener cartridge, comprising:
    a cartridge body, comprising:
        a deck comprising an uneven tissue compression surface, wherein a longitudinal slot is defined through at least a portion of said uneven tissue compression surface; and
        fastener cavities, comprising:
            a first fastener cavity defined in said uneven tissue compression surface on a first side of said longitudinal slot; and
            a second fastener cavity defined in said uneven tissue compression surface on the first side of said longitudinal slot; and
    unfired fasteners, comprising:
        a first unfired fastener removably positioned in said first fastener cavity and comprising a first height; and
        a second unfired fastener removably positioned in said second fastener cavity and comprising a second height, wherein said first height and said second height are different;
    wherein said uneven tissue compression surface comprises a plurality of peaks between said first fastener cavity and said second fastener cavity.

10. A fastener cartridge, comprising:
    a cartridge body, comprising:
        a deck comprising an uneven tissue compression surface, wherein a longitudinal slot is defined through at least a portion of said uneven tissue compression surface; and
        fastener cavities, comprising:

a first fastener cavity defined in said uneven tissue compression surface on a first side of said longitudinal slot; and
a second fastener cavity defined in said uneven tissue compression surface on the first side of said longitudinal slot;
unfired fasteners, comprising:
a first unfired fastener removably positioned in said first fastener cavity and comprising a first height; and
a second unfired fastener removably positioned in said second fastener cavity and comprising a second height, wherein said first height and said second height are different; and
further comprising a sled configured to fire said unfired fasteners from said fastener cavities during a firing stroke;
wherein said uneven tissue compression surface comprises at least one peak between said first fastener cavity and said second fastener cavity.

11. The fastener cartridge of claim 10, further comprising a cutting edge configured to move along said longitudinal slot during the firing stroke.

12. A fastener cartridge, comprising:
a cartridge body comprising an uneven tissue compression surface, wherein a longitudinal slot is defined through at least a portion of said uneven tissue compression surface; and
unfired fasteners removably positioned in said cartridge body, wherein said unfired fasteners comprise:
a first unfired fastener on a first side of said longitudinal slot, wherein said first unfired fastener comprises a first height; and
a second unfired fastener on the first side of said longitudinal slot, wherein said second unfired fastener comprises a second height, and wherein said first height and said second height are different;
wherein said uneven tissue compression surface comprises a plurality of peaks on the first side of said longitudinal slot, and wherein said uneven tissue compression surface is configured to provide variable pre-compression laterally along a width of said cartridge body.

13. A fastener cartridge, comprising:
a cartridge body comprising an uneven tissue compression surface, wherein a longitudinal slot is defined through at least a portion of said uneven tissue compression surface; and
unfired fasteners removably positioned in said cartridge body, wherein said unfired fasteners comprise:
a first unfired fastener on a first side of said longitudinal slot, wherein said first unfired fastener comprises a first height; and
a second unfired fastener on the first side of said longitudinal slot, wherein said first unfired fastener is laterally offset from said second unfired fastener, wherein said second unfired fastener comprises a second height, and wherein said first height and said second height are different;
wherein said uneven tissue compression surface comprises a plurality of peaks on the first side of said longitudinal slot.

14. A fastener cartridge, comprising:
a cartridge body comprising an uneven tissue compression surface, wherein a longitudinal slot is defined through at least a portion of said uneven tissue compression surface; and
unfired fasteners removably positioned in said cartridge body, wherein said unfired fasteners comprise:
a first unfired fastener on a first side of said longitudinal slot, wherein said first unfired fastener comprises a first height; and
a second unfired fastener on the first side of said longitudinal slot, wherein said second unfired fastener comprises a second height, and wherein said first height and said second height are different;
wherein said uneven tissue compression surface comprises a plurality of peaks on the first side of said longitudinal slot, and wherein said peaks comprise the same peak height.

15. A fastener cartridge, comprising:
a cartridge body comprising an uneven tissue compression surface, wherein a longitudinal slot is defined through at least a portion of said uneven tissue compression surface;
unfired fasteners removably positioned in said cartridge body, wherein said unfired fasteners comprise:
a first unfired fastener on a first side of said longitudinal slot, wherein said first unfired fastener comprises a first height; and
a second unfired fastener on the first side of said longitudinal slot, wherein said second unfired fastener comprises a second height, and wherein said first height and said second height are different; and
a sled configured to fire said unfired fasteners from said cartridge body during a firing stroke;
wherein said uneven tissue compression surface comprises a plurality of peaks on the first side of said longitudinal slot.

* * * * *